(12) United States Patent
Strauch et al.

(10) Patent No.: US 12,702,514 B2
(45) Date of Patent: Aug. 11, 2026

(54) SURGICAL DRAPE WITH SEPARABLE ELEMENTS

(71) Applicant: Creative Surgical Solutions, LLC, Vail, CO (US)

(72) Inventors: Eric Strauch, Vail, CO (US); Donald Corenman, Edwards, CO (US); Dan Droy, Denver, CO (US); Andrew VanDeWeghe, Grayslake, IL (US); Shayna Massi, Palatine, IL (US); Phillip Brown, Cary, IL (US); Evelina Leece, Chicago, IL (US); Samba Toure, Grand Blanc, MI (US); Nicholas Sievers, Clarkston, MI (US); Charles Kline, Ontario, CA (US)

(73) Assignee: Creative Surgical Solutions, LLC, Edwards, CO (US)

( * ) Notice: Subject to any disclaimer, the term of this patent is extended or adjusted under 35 U.S.C. 154(b) by 1043 days.

(21) Appl. No.: 17/062,610

(22) Filed: Oct. 4, 2020

(65) Prior Publication Data

US 2021/0015576 A1 Jan. 21, 2021

Related U.S. Application Data

(63) Continuation-in-part of application No. 16/435,495, filed on Jun. 8, 2019, now Pat. No. 11,185,381, which (Continued)

(51) Int. Cl.

*A61B 46/10* (2016.01)
*A61B 46/00* (2016.01)
*A61B 17/00* (2006.01)

(52) U.S. Cl.

CPC .... *A61B 46/00* (2016.02); *A61B 2017/00902* (2013.01)

(58) Field of Classification Search

CPC ... A61B 46/20; A61B 46/27; A61B 2046/201; A61B 2046/205; A61B 2046/234; A61B 2046/236

See application file for complete search history.

(56) References Cited

U.S. PATENT DOCUMENTS

| | | | |
|---|---|---|---|
| 2,353,858 | A | 7/1944 | Tedesco |
| RE24,613 | E | 3/1959 | Hageltorn |

(Continued)

FOREIGN PATENT DOCUMENTS

| | | |
|---|---|---|
| CN | 1214625 | 4/1999 |
| CN | 101721255 | 6/2010 |

(Continued)

OTHER PUBLICATIONS

Official Action for U.S. Appl. No. 17/535,347, dated Jan. 6, 2023 12 pages.

(Continued)

*Primary Examiner* — Camtu T Nguyen
(74) *Attorney, Agent, or Firm* — Sheridan Ross P.C.

(57) ABSTRACT

The present disclosure relates to a surgical drape to be used in conjunction with a surgical procedure, and more specifically to a surgical drape that includes one or more of the following: (1) a patient drape for use with a standalone non-draped image acquisition device (requiring circumferential access to the patient); (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; (5) the means to provide covering of the undersurface of the operating surface and enclosing any suspended medical devices, wires, cables, tubes, etc; and (6) a single-use disposable outer surgical drape that ensures sterility of a covered (Continued)

surgical apparatus, device, or machine, or an inner drape associated therewith.

20 Claims, 61 Drawing Sheets

Related U.S. Application Data is a continuation of application No. 14/846,388, filed on Sep. 4, 2015, now Pat. No. 10,363,108, which is a continuation-in-part of application No. 14/280,416, filed on May 16, 2014, now Pat. No. 10,363,110, which is a continuation of application No. 13/155,219, filed on Jun. 7, 2011, now Pat. No. 8,726,907, said application No. 16/435,495 is a continuation-in-part of application No. 14/280,416, filed on May 16, 2014, now Pat. No. 10,363,110.

(60) Provisional application No. 62/046,029, filed on Sep. 4, 2014, provisional application No. 61/352,045, filed on Jun. 7, 2010, provisional application No. 61/357,637, filed on Jun. 23, 2010, provisional application No. 61/490,432, filed on May 26, 2011.

(56) References Cited

U.S. PATENT DOCUMENTS

| | | | | |
|---|---|---|---|---|
| 2,960,561 | A | 11/1960 | Plummer | |
| 3,060,932 | A | 10/1962 | Pereny et al. | |
| 3,255,809 | A | 6/1966 | Kawczynski | |
| 3,682,163 | A | 8/1972 | Plummer | |
| 3,698,395 | A | 10/1972 | Hansson | |
| 3,738,405 | A * | 6/1973 | Ericson | A61B 50/13 248/176.1 |
| 3,741,203 | A | 6/1973 | Liman | |
| 3,835,851 | A | 9/1974 | Villari | |
| 3,882,859 | A | 5/1975 | Ericson | |
| 4,045,118 | A * | 8/1977 | Geraci | G02B 23/18 359/510 |
| 4,090,508 | A | 5/1978 | Gaylord, Jr. | |
| 4,153,054 | A | 5/1979 | Boone | |
| 4,369,356 | A | 1/1983 | Tsurutani et al. | |
| 4,627,426 | A | 12/1986 | Wegener et al. | |
| 4,782,502 | A | 11/1988 | Schulz | |
| 4,873,997 | A | 10/1989 | Marshall | |
| 4,887,339 | A | 12/1989 | Bellanger | |
| 4,905,710 | A | 3/1990 | Jones | |
| 4,939,819 | A | 7/1990 | Moyer | |
| 5,127,423 | A | 7/1992 | Draeger | |
| 5,170,804 | A * | 12/1992 | Glassman | A61B 50/10 128/849 |
| 5,187,813 | A | 2/1993 | Klein | |
| 5,263,970 | A | 11/1993 | Preller | |
| 5,379,703 | A * | 1/1995 | Marshall | A61B 50/13 108/90 |
| 5,503,163 | A | 4/1996 | Boyd | |
| 5,515,868 | A | 5/1996 | Mills | |
| 5,527,312 | A | 6/1996 | Ray | |
| 5,569,246 | A | 10/1996 | Ojima et al. | |
| 5,605,534 | A | 2/1997 | Hutchison | |
| 5,651,375 | A | 7/1997 | Cunningham | |
| 5,674,189 | A | 10/1997 | McDowell et al. | |
| 5,810,750 | A | 9/1998 | Buser | |
| 5,817,038 | A | 10/1998 | Orange et al. | |
| 5,865,846 | A | 2/1999 | Bryan et al. | |
| 5,871,015 | A * | 2/1999 | Lofgren | A61B 46/10 128/849 |
| 6,030,401 | A | 2/2000 | Marino | |
| 6,113,602 | A | 9/2000 | Sand | |
| 6,142,998 | A | 11/2000 | Smith et al. | |
| 6,286,511 | B1 | 9/2001 | Levitt et al. | |
| 6,290,724 | B1 | 9/2001 | Marino | |
| 6,309,395 | B1 | 10/2001 | Smith et al. | |
| 6,314,959 | B1 | 11/2001 | Griesbach et al. | |
| 6,328,738 | B1 | 12/2001 | Suddaby | |
| 6,364,880 | B1 | 4/2002 | Michelson | |
| 6,719,795 | B1 | 4/2004 | Cornwall et al. | |
| 7,014,640 | B2 | 3/2006 | Kemppanien et al. | |
| 7,025,769 | B1 | 4/2006 | Ferree | |
| 7,044,133 | B2 * | 5/2006 | Lohrengel | A61B 46/10 128/849 |
| 7,077,864 | B2 | 7/2006 | Byrd, III et al. | |
| 7,104,201 | B2 * | 9/2006 | Comeaux | A61B 50/13 108/90 |
| 7,182,088 | B2 | 2/2007 | Jenkins | |
| 7,207,992 | B2 | 4/2007 | Ritland | |
| 7,288,093 | B2 | 10/2007 | Michelson | |
| 7,341,590 | B2 | 3/2008 | Ferree | |
| 7,387,643 | B2 | 6/2008 | Michelson | |
| 7,406,775 | B2 | 8/2008 | Funk et al. | |
| 7,665,606 | B2 * | 2/2010 | Gaillard | A61B 46/10 206/363 |
| 8,707,961 | B1 * | 4/2014 | Kazravan | A61B 50/10 128/849 |
| 8,726,907 | B2 | 5/2014 | Strauch et al. | |
| 10,363,108 | B2 * | 7/2019 | Strauch | A61B 46/10 |
| 10,363,110 | B2 * | 7/2019 | Strauch | A61B 46/40 |
| 10,610,321 | B2 * | 4/2020 | Ueda | A61B 46/10 |
| 11,185,381 | B2 * | 11/2021 | Strauch | A61B 46/20 |
| 11,185,382 | B2 | 11/2021 | Toure | |
| 11,883,212 | B2 * | 1/2024 | Young | A61B 46/10 |
| 2004/0194673 | A1 * | 10/2004 | Comeaux | A47G 11/004 108/90 |
| 2006/0064797 | A1 | 3/2006 | Rowe et al. | |
| 2006/0137693 | A1 | 6/2006 | Lewis et al. | |
| 2007/0102005 | A1 | 5/2007 | Bonutti | |
| 2007/0162096 | A1 | 7/2007 | Zakuto et al. | |
| 2008/0000006 | A1 | 1/2008 | Ochoa et al. | |
| 2008/0168995 | A1 | 7/2008 | Yardan et al. | |
| 2008/0255564 | A1 | 10/2008 | Michelson | |
| 2009/0277460 | A1 | 11/2009 | Carrez et al. | |
| 2010/0031966 | A1 | 2/2010 | Allen | |
| 2010/0186754 | A1 | 7/2010 | Carrez et al. | |
| 2010/0192960 | A1 | 8/2010 | Rotolo | |
| 2012/0312308 | A1 | 12/2012 | Allen | |
| 2013/0072839 | A1 | 3/2013 | Cuypers et al. | |
| 2013/0312769 | A1 | 11/2013 | Letoquoy | |
| 2014/0081291 | A1 | 3/2014 | Groke et al. | |
| 2015/0114404 | A1 | 4/2015 | Czop et al. | |
| 2022/0079698 | A1 | 3/2022 | Strauch et al. | |
| 2022/0079699 | A1 | 3/2022 | Toure | |
| 2025/0064543 | A1 * | 2/2025 | Abbott | A61B 46/10 |

FOREIGN PATENT DOCUMENTS

| | | |
|---|---|---|
| CN | 102112068 | 6/2011 |
| CN | 102596089 | 7/2012 |
| CN | 104768493 | 7/2015 |
| FR | 2896146 | 7/2007 |
| WO | WO 2017/040454 | 3/2017 |

OTHER PUBLICATIONS

Notice of Allowance for U.S. Appl. No. 17/535,347, dated Jun. 30, 2023 10 pages.

Notice of Allowance for U.S. Appl. No. 17/535,384, dated Feb. 3, 2023 10 pages.

File History of U.S. Appl. No. 61/352,045, filed Jun. 7, 2010.

File History of U.S. Appl. No. 61/357,637, filed Jun. 23, 2010.

International Search Report for International Patent Application No. PCT/US2012/039555, mailed Sep. 14, 2012, 3 pages.

Written Opinion for International Patent Application No. PCT/US2012/039555, mailed Sep. 14, 2012, 4 pages.

International Preliminary Report on Patentability for International (PCT) Patent Application No. PCT/US2012/039555, mailed Apr. 10, 2014 6 pages.

Official Action (with English Translation) for China Patent Application No. 2012800255508, dated Nov. 30, 2015 19 pages.

(56) References Cited

OTHER PUBLICATIONS

Notice of Allowance (with English translation) for China Patent Application No. 201280025550.8, dated Nov. 18, 2016 9, 5 pages.
Extended Search Report for European Patent Application No. 12789811.2, dated May 11, 2015 6 pages.
Article 94(3) Communication for European Patent Application No. 12789811.2, dated Oct. 8, 2019, 6 pages.
Official Action (no English translation available) for Mexican Patent Application No. MX/a/2019/011486, dated Jul. 23, 2020, 3 pages.
International Search Report and Written Opinion for International (PCT) Patent Application No. PCT/US16/49358, dated Nov. 10, 2016, 8 pages.
International Preliminary Report on Patentability for International (PCT) Patent Application No. PCT/US2016/049358, dated Mar. 15, 2018, 7 pages.
Extended European Search Report for European Patent Application No. 18191933.3, dated Jan. 17, 2019, 8 pages.
Official Action for U.S. Appl. No. 13/155,219 mailed Nov. 21, 2012, 9 pages.
Official Action for U.S. Appl. No. 13/155,219, mailed May 17, 2013 9 pages.
Official Action for U.S. Appl. No. 13/155,219, mailed Sep. 13, 2013 12 pages.
Notice of Allowance for U.S. Appl. No. 13/155,219, mailed Mar. 28, 2014 9 pages.
Official Action for U.S. Appl. No. 14/280,416, dated Oct. 26, 2016, 20 pages.
Official Action for U.S. Appl. No. 14/280,416, dated Mar. 14, 2017, 20 pages.
Official Action for U.S. Appl. No. 14/280,416, dated Jul. 12, 2017, 16 pages.
Official Action for U.S. Appl. No. 14/280,416, dated Mar. 22, 2018, 17 pages.
Official Action for U.S. Appl. No. 14/280,416, dated Dec. 13, 2018, 18 pages.
Notice of Allowance for U.S. Appl. No. 14/280,416, dated Mar. 6, 2019, 10 pages.
Official Action for U.S. Appl. No. 14/846,388, dated Oct. 4, 2016, 20 pages.
Official Action for U.S. Appl. No. 14/846,388 dated Feb. 8, 2018, 14 pages.
Official Action for U.S. Appl. No. 14/846,388 dated Mar. 30, 2018, 15 pages.
Official Action for U.S. Appl. No. 14/846,388 dated Sep. 24, 2018, 16 pages.
Notice of Allowance for U.S. Appl. No. 14/846,388 dated Mar. 15, 2019, 9 pages.
Official Action for U.S. Appl. No. 16/435,495, dated Aug. 28, 2020, 8 pages. Restriction Requirement.
Official Action for U.S. Appl. No. 16/435,495, dated Feb. 3, 2021, 12 pages.
Notice of Allowance for U.S. Appl. No. 16/435,495, dated Jun. 30, 2021, 8 pages.
Official Action for U.S. Appl. No. 16/119,205, dated Dec. 2, 2020, 11 pages.
Article 94(3) Communication for European Patent Application No. 12789811.2, dated Apr. 9, 2021, 6 pages.
Intention to Grant for European Patent Application No. 12789811.2, dated Nov. 3, 2021 42 pages.
International Search Report and Written Opinion for International (PCT) Patent Application No. PCT/US2021/053345, dated Jan. 27, 2022 13 pages.
Notice of Allowance for U.S. Appl. No. 16/119,205, dated Jun. 10, 2021, 10 pages.
Corrected Notice of Allowance for U.S. Appl. No. 18/247,679, dated Oct. 15, 2024 5 pages.
Notice of Allowance for U.S. Appl. No. 18/247,679, dated Jul. 3, 2024 9 pages.

* cited by examiner

2

6
4
4
2

4
8
6
10
2
4
6
8
20
10

14
12

FIG. 15C
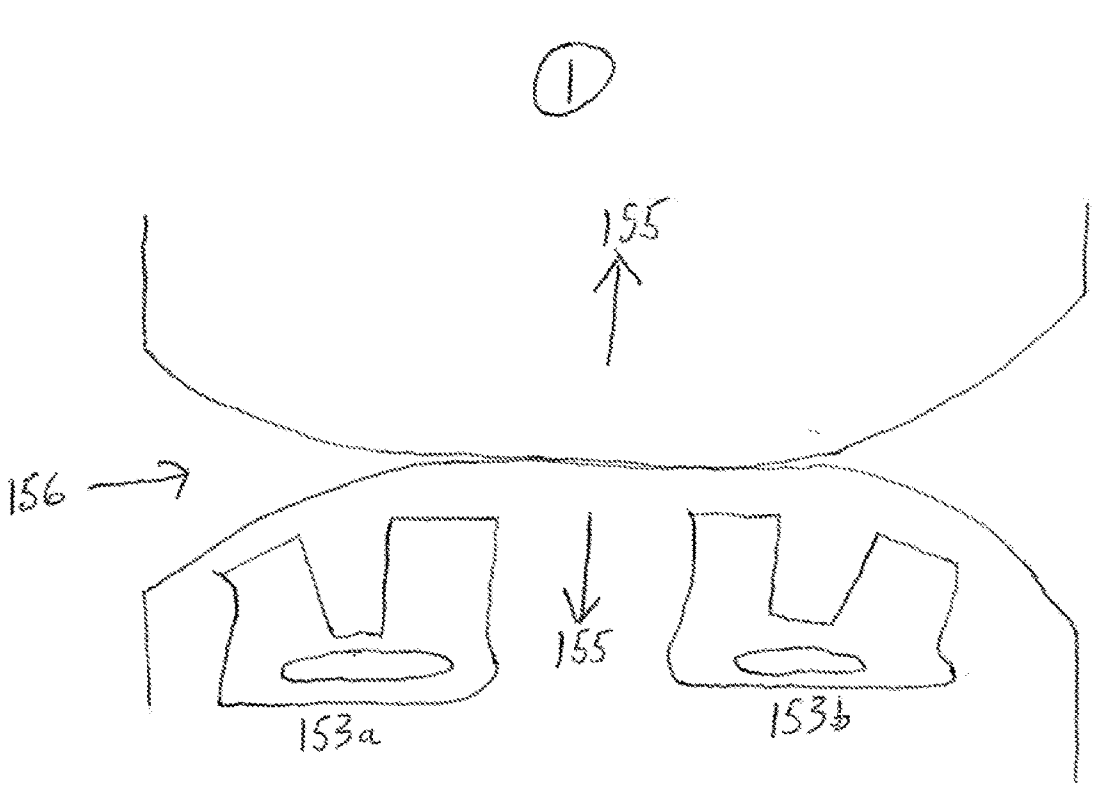
1
155
156
155
153a
153b
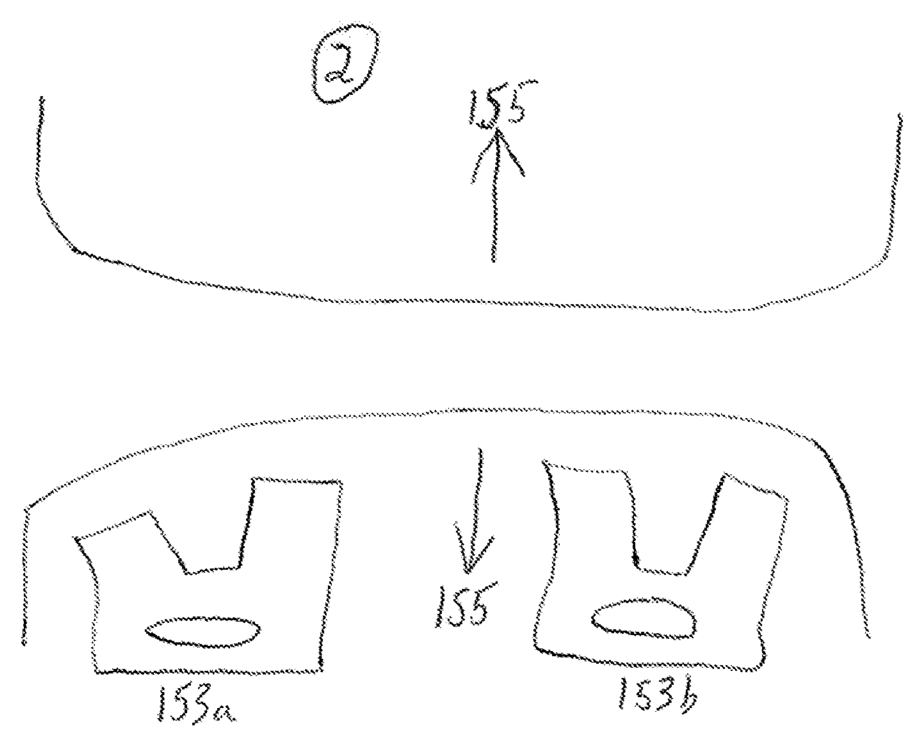
2
155
155
153a
153b 214
215b
215a
212

222
225
223

222
225
226a
226b 232
235
236a
236b 300
301
3011
306

300
3011
306

300
3011
306

300
3011
306

361
36
36

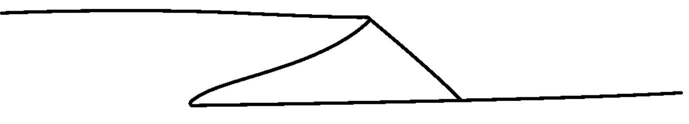
FIG.45A
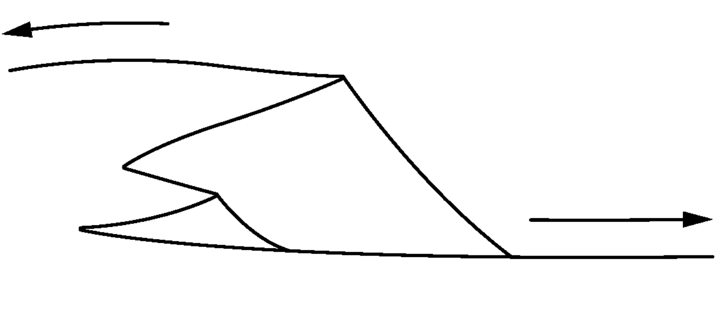
FIG.45B
FIG.45C

SURGICAL DRAPE WITH SEPARABLE ELEMENTS

CROSS-REFERENCE TO RELATED APPLICATIONS

The present application is a continuation-in-part of U.S. patent application Ser. No. 16/435,495, filed Jun. 8, 2019, which is a continuation of U.S. patent application Ser. No. 14/846,388, filed Sep. 4, 2015, which (1) claims priority from U.S. Provisional Application No. 62/046,029, filed Sep. 4, 2014, and (2) is a continuation-in-part of U.S. patent application Ser. No. 14/280,416, filed May 16, 2014, which is a continuation of U.S. patent application Ser. No. 13/155,219, filed Jun. 7, 2011, which claims priority from U.S. Provisional Application Nos. 61/352,045, filed Jun. 7, 2010, 61/357,637 filed Jun. 23, 2010, and 61/490,432 filed May 26, 2011. The disclosures of all of the above-referenced applications are hereby incorporated by reference in their entireties.

FIELD OF THE INVENTION

This disclosure relates to orthopedic surgery, and more specifically to a surgical drape that includes one or more of the following: (1) a patient drape for use with a standalone non-draped image acquisition device (requiring circumferential access to the patient); (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; (5) the means to provide covering of the undersurface of the operating surface and enclosing any suspended medical devices, wires, cables, tubes, etc; and (6) a single-use disposable outer surgical drape that ensures sterility of a covered surgical apparatus, device, or machine, or an inner drape associated therewith.

BACKGROUND OF THE INVENTION

Individuals may suffer a variety of spinal disorders involving degenerative disc disease, spine deformity, herniated discs, traumatic injuries and congenital anomalies. Some of these pathologies may require surgery on the affected region to relieve the individual from pain and/or prevent further injury to the spine and neural structures. Spinal surgery may involve decompression of the spinal cord and nerves, stabilization of painful or unstable motion segments and correction of deformity. The surgical procedure will vary depending on the nature and extent of the pathology. In all instances, it is critical that a sterile field be maintained throughout the procedure, regardless of its duration. Published standards and recommended practices exist, including those developed by the Association of periOperative Registered Nurses (AORN), which provide guidelines to be used by a surgical team when caring for their patients in an operative setting.

It is the goal of the surgical team to prevent the contamination of an open surgical wound by isolating the operative site from the surrounding nonsterile environment. The surgical team accomplishes this by creating and maintaining the sterile field and by following aseptic principles aimed at preventing microorganisms from contaminating the surgical wound. Sterile surgical drapes establish an aseptic barrier minimizing the passage of microorganisms from nonsterile to sterile areas. Sterile drapes should be placed on the patient, furniture, and equipment to be included in the sterile field, leaving only the incisional site exposed. During the draping process, only scrubbed personnel should handle sterile drapes. The drapes should be held higher than the operating room bed with the patient draped from the prepped incisional site out to the periphery. According to the standards published by AORN, once the sterile drape is positioned, it should not be moved or rearranged.

Several disadvantages exist regarding current methods for maintaining sterility throughout a spinal surgery. First, current makeshift draping procedures (fitting a multitude of drapes around the patient) are time consuming and thus prolong the length of the procedure. Second, current methods of draping the various equipment and surgical implements are complicated and challenging to accomplish efficiently. Third, maintaining a sterile field throughout the procedure is more challenging, especially when using radiological equipment. Finally, current draping systems do not provide a well-accepted means to provide temporary sterile coverage of underlying sterile equipment tables and trays.

Currently, navigation technology in conjunction with three dimensional ("3D") radiographic technology is being utilized to make surgical techniques more time-efficient, accurate, and safer. Using 3D imaging by utilizing an "O-arm" device (with or without navigation technology) presents challenges both in regard to appropriate draping and maintenance of a sterile field as well as maneuverability of the 3D imaging device in and out of the sterile field. "C-arm" surgical cases can present similar challenges.

In regards to the above-referenced radiological equipment, to create a sterile "tunnel" with drapes through which the arm can pass (as it rises from the unsterile 'below table' region to the sterile 'above table region') is not only cumbersome and time-consuming, but also a potential risk to the sterile field if such a method were to fail (e.g., an unsterile drape falls into the sterile field as the radiological device arm propels it superiorly).

Sleeve type drapes for covering an 'O-arm' have been utilized. Aside from the fact that they are time-intensive and cumbersome, these drapes can contaminate the field if they become displaced as the O-arm is enclosing around the OR table. Also, the sag of the drape off the underside of the most superior aspect of the O-arm can block the reference frame from being properly read and displayed by the monitor. Finally, given the effort necessary in draping the 3D radiological device itself, the surgeon may decide to leave the device in the field and operate around it, thereby avoiding having to re-drape again for later imaging. Thus, the surgeon is compromised as he/she attempts to perform the surgery with the 3D device left in place.

Currently, many surgeons utilizing a 3D acquisition device in conjunction with navigation technology have devised makeshift draping systems that, while draping the patient rather than the radiographic device for reasons stated above, attempt to maintain complete protection to the underlying sterile field. The reference frame attached to the patient's anatomy (often the spinous process) must protrude through the disposable, makeshift draping system (formed by two approximated half sheets secured by steri-strips) in order to be readable by the navigation monitor. However, the reference frame cannot be exposed to the underside of the undraped (and thus non-sterile) 3D radiographic device above. Therefore, the reference frame is often covered by a piece of clear plastic to maintain the sterility of the reference frame attached to the patient's anatomy, but at the same time, allow for the reference frame to be readable by the navigation monitor. This piece of clear plastic also serves another purpose—it covers the medial borders of both approximated half-sheets that run longitudinally along the sagittal midline of the patient through which the reference frame neck protrudes. When removing this makeshift draping system, the plastic cover is removed, followed by the fall of both half sheets laterally off the table.

Numerous problems exist in regard to draping when attempting to use 3D devices and concomitantly maintain a sterile field. In regard to the makeshift draping system described above, several concerns are raised. First, any breach in the makeshift drape system (e.g. gap, tear or opening) can potentially cause the drape to fail in its intended purpose—protecting the patient from infection by preventing microorganisms from making their way into the skin opening of the surgical site. For instance, the plastic covering of the reference frame and medial borders of the two approximated half sheets often does not extend the entire length of the half-sheets. Thus, if the 3D radiographic device swings into position over any portion of the approximated half-sheets uncovered by the plastic cover, the medial borders are potentially exposed. When the half-sheets fall laterally to the floor during the removal process, it is possible that contamination of the underlying sterile field could occur as the medial edges of the half-sheets make contact. Second, the time in gathering the components of such a makeshift draping system (2 half-sheets, two non-piercing hemostats/clamps, steri-strips, and a cut out plastic covering) and placing into position is labor and time-intensive. Certainly, it can be expected that any relatively new scrub technician will not have such components ready in an efficient manner.

The accuracy of integration of the anatomical information provided by the 3D data acquisition device and the navigation system depends on the technology utilized, the readability of the reference frame, and the stability of the reference frame. Under the assumption that medical providers are content with the technological capabilities of the system, the two remaining variables regarding accuracy of integration of anatomical data and monitored (navigated) surgical instruments are the readability and stability of the reference frame. Under the assumption that medical providers remain meticulous in avoidance of reference frame displacement, then the remaining factor affecting the accuracy of the system is based on the readability of the reference frame. A thin, clear plastic is therefore desirable to minimize refraction of the infrared light thereby minimizing any inaccuracy that may inherently exist with indirect communication of the navigation monitor and the reference frame.

In addition, a variety of apparatuses, devices, and machines utilized in surgery cannot be brought into and/or placed over a sterile field without being properly covered or draped to prevent contaminants from falling or otherwise being transported into or onto the sterile field. To accomplish this, a wide variety of surgical drapes, each of which is specifically adapted or configured to cover or drape one specific type of apparatus, device, or machine, must be manufactured; for example, one type of currently manufactured surgical drape is specifically designed to cover or drape microscopes, another type of drape is specifically designed to cover or drape robots used da Vinci® surgical system robots, another type of drape is specifically designed to cover or drape Medtronic's Mazor™ line of surgical system robots, and so on. Any large surgical apparatus, device, or machine, including (by way of non-limiting example) radiographic equipment, surgical robotic systems, and surgical microscopes, that is developed and/or used in the future will likewise require its own type of surgical drape. Covering or draping surgical apparatuses, devices, and machines is necessarily a meticulous, painstaking, and therefore time-consuming process, requiring careful attention to preservation of sterility; by way of non-limiting example, draping a surgical microscope generally takes five to ten minutes, and draping a da Vinci® surgical system robot generally takes seven to fifteen minutes.

Current solutions allow surgical technicians and/or nurses to cover or drape these and other apparatuses, devices, and machines, including but not limited to surgical back tables, when setting up an operating room prior to the start of a surgical procedure. However, if surgical equipment is covered or draped prior to the start of the procedure, it is likely that the drapes themselves will be contaminated before the draped device is used, thereby defeating the intended purpose of the drape, i.e. to protect the sterile field from contamination being introduced via the device. A significant body of evidence-based literature has recently indicated that this mode of contamination presents a significant challenge to operating room personnel; indeed, AORN has recently revised its recommendations to indicate that back tables should, rather than may, be covered during times of increased activity or delay.

Many surgical apparatuses, devices, and machines, including but not limited to surgical microscopes and da Vinci® surgical robots, are large and cumbersome, and therefore not easily moved or repositioned after a surgical procedure has begun. Thus, another contamination risk of pre-draped surgical equipment presents itself: operating room personnel may contaminate a drape that covers or drapes an apparatus, device, or machine as they move around the operating room during the procedure but prior to use of the apparatus, device, or machine. If the surgical drape is contaminated by coming in contact with non-sterile operating room personnel during the surgical procedure, the drape must be removed and replaced during the procedure and before the apparatus, device, or machine intended to be covered or draped is use; this removes the attention of the operating room personnel from the surgical procedure itself, and increases the time, cost, and risk of the surgical procedure.

Thus, multiple problems exist in prior art draping apparatus and methods, and in particular providing a sterile field where a separation is necessary to accommodate one or more pieces of equipment used during the surgery. Because the use of makeshift draping is both time and labor intensive, does not adequately address the helpful 'under the table' enclosure, and fails to preserve sterile technique, many surgeons have opted to simply not drape the sterile fields as well as the 3D radiographic device. The present disclosure addresses all of these challenges and other shortcomings in the prior art.

SUMMARY OF THE INVENTION

This disclosure relates to orthopedic surgery, and more specifically to a one piece customized disposable surgical drape that includes one or more of the following: (1) a patient drape for use with a standalone non-draped image acquisition device (requiring circumferential access to the patient); (2) a patient drape for use with a standalone non-draped image acquisition device with image guidance navigation technology; (3) the means to provide temporary sterile coverage of an underlying sterile field; (4) the means to provide sterile separation of at least a portion, if not the entire temporary sterile coverage; and (5) the means to provide covering of the undersurface of the operating surface and enclosing any suspended medical devices, wires, cables, tubes, etc.

This disclosure further relates to single-use, disposable, general-purpose outer surgical drapes, provided in a bag- or tube-like configuration or shape, that are adapted to be placed over an inner surgical drape adapted or designed to cover a specific item of surgical equipment (e.g. a surgical microscope or da Vinci® surgical robot). In this aspect, the general-purpose outer surgical drape may be removed in such a way that a non-sterile surface never contacts or moves over the underlying inner surgical drape, thereby preserving the sterility of the underlying inner surgical drape.

According to one embodiment, an apparatus is disclosed wherein a draping device is utilized for concomitant use of navigation technology and 3D imaging, featuring 'through plastic (or lens) readability, sterile longitudinal separation, and under-table wrapping capability, as described in greater detail below.

According to one embodiment, an apparatus is disclosed wherein a draping device further allows for navigation readability of one or more reference frames both indirectly (through plastic or lens) and directly (without plastic or lens). The level of sterility depends on the option chosen. Sterile longitudinal separation of the draping device in one or more locations and under-table wrapping capabilities are similarly provided with this embodiment.

According to one embodiment, an apparatus is disclosed wherein a draping device is provided to offer temporary coverage for an underlying sterile field (without navigation technology). This may involve 2D or 3D imaging without navigation (e.g. no reference frame) or temporary sterile coverage of a sterile or equipment table. The drape of this embodiment has a longitudinal sterile separation element, and the under-table wrapping capability may also be provided. The plastic component may be provided, or alternatively the draping device may be manufactured as a plastic or transparent paper drape, or similar transparent material.

Navigation and 3D Imaging Use

When performing a 3D imaging or a radiological procedure, the equipment and imaging technology often requires that a patient has a sterile reference frame attached to and protruding from his/her anatomy that needs to be readable by a navigation monitor while 3D imaging is obtained. The surgical drape device according to one embodiment is designed to drape the sterile field rather than the radiological device. It accommodates a surgeon's preference, as it allows for navigation readability of the attached reference frame through a clear plastic material or optical lens while the 3D acquisition is taking place.

Incorporation of a clear plastic region or lens into the drape device preserves sterility of the underlying reference frame and surgical field, while simultaneously allowing for readability of the reference frame by the navigation device. In spine surgery, the surgical drape permits reference frame placement in the posterior cervical, thoracic and lumbar spine axial positions, as well as the posterior superior iliac crest position (on either side). The drape device therefore accommodates different anatomical placements of the reference frame (such as when utilized in maxillofacial/ENT surgery and pelvic trauma) and/or various positions of the monitor, such as for cranial positioning.

Sterile Separation of Two Opposing Edges

The draping device according to varying embodiments provides at least one location for achieving a longitudinal separation of the drape, while still maintaining the sterility of the separating edges, and allows for easy removal of the drape. The two separating halves of the drape can fall to their respective side of the OR table in a sterile manner, thus exposing the underlying sterile field for continuance of surgery. Several unique arrangements and mechanisms for sterile separation are described below.

This particular embodiment is critical where a surgical patient is draped, rather than a radiological device. However, the sterile separation of two opposing edges may also be applied to a drape utilized in a variety of non-radiographic imaging situations where temporary coverage of a sterile field is necessary. Examples of such uses are also described below.

Under-Table Wrap Up Component

According to another embodiment, the drape device allows for complete enclosure of the patient not only above the table but also underneath the table (in the unsterile region). The portion of the drape underneath the table will clasp in one or more locations to enclose the various wires, cords, and tubes (e.g. neuromonitoring wires, catheter, etc.) and allow for easy and efficient positioning (entrance and exit) of any required non-sterile 2D or 3D image data acquisition device around the table and patient.

When 2D or 3D imaging is used as a standalone device (and thus without concomitant use of navigation technology), the drape still offers desirable improvements over the prior art in the sterile separation of two longitudinal opposing edges (e.g. 'double underbite' separation) as well as the 'under-the-table' wrapping component, both making surgery safer and more efficient.

In one embodiment, a drape is provided with a selectively separable portion intersecting a lateral point proximal to a midpoint of a predetermined width of the drape. In a further embodiment, a drape comprises a selectively separable portion intersecting a lateral point that is proximal to a midpoint of a predetermined width of the drape and within a middle third of the predetermined width. In a further embodiment, a drape comprises a selectively separable portion intersecting a lateral point that is proximal to a midpoint of a predetermined width of the drape and wherein the midpoint is equidistant from the first peripheral edge and the second peripheral edge of the drape.

Surgical Back Table Use

According to one embodiment, the drape allows for the maintenance of sterility of a table where surgical instruments are kept while not in use, commonly referred to as a "back table," and the instruments and equipment thereon. The two halves of the drape may be separated and drawn away from the back table on opposing sides, such that no dust, debris or foreign items fall from the drape onto the back table and thus contaminate it. After the two halves of the drape have been separated and the drape has been removed, the instruments and equipment on the operating table may be accessed by a surgeon or his or her assistants when needed to continue the surgery.

Mayo Stand Cover

According to one embodiment, the drape allows for the maintenance of sterility of a movable or repositionable instrument stand, commonly referred to as a "Mayo stand," and the instruments and equipment thereon. The drape may have multiple separable sections, which may be pulled apart along a perforation or other separating line and drawn away from or off of the mayo stand, such that no dust, debris, or foreign items fall from the drape onto the stand and thus contaminate it. After the drape has been removed, the instruments on the mayo stand may be accessed by a surgeon or his or her assistants when needed to continue the surgery.

Single-Use Disposable Outer Drape

In embodiments, a single-use disposable outer surgical drape, adapted or configured to cover or drape an underlying inner drape for an item of surgical equipment, is provided. The outer surgical drape is generally bag-shaped (i.e. having one open end or mouth) or tube-shaped (i.e. having two open ends or mouths) and comprises a "Z-fold"-type pleat, allowing the drape to be separated along a perforation or other separating line in a manner that maintains the sterility of the two separating edges. Given the outer surgical drape's bag- or tube-like shape, the Z-fold is circumferential, i.e. is disposed about the entirety of a circumference of the drape. In this way, the outer surgical drape can be opened or separated along the Z-fold in such a way that a non-sterile edge of the open mouth may remain in place while two sterile edges—which had previously been covered and maintained as sterile by the overlying circumferential Z-fold pleat—are separated; one of the two sterile edges is dragged over the underlying inner drape as the outer drape is removed, while the other sterile edge remains in place and at a constant distance from the non-sterile edge of the open mouth. The outer drape of the present invention thus allows a protected, sterile item of surgical equipment to remain sterile and then immediately used on, in, or over a sterile field.

Items of surgical equipment that may be suitable for use with the single-use disposable outer surgical drapes of these embodiments may be, by way of non-limiting example, large and cumbersome surgical apparatuses, devices, or machines (e.g. surgical microscopes and da Vinci® surgical robots), or any other apparatus, device, machine, or item of equipment used in surgery that may need to be kept sterile for a significant length of time (e.g. a Mayo stand having sterile surgical instruments thereon). In some applications, especially those in which the outer drape having a bag- or tube-like shape and a circumferential Z-fold is used to cover a small and/or portable item of surgical equipment, e.g. a Mayo stand, it will not always be necessary to utilize an inner drape; in other words, the single-use disposable outer drapes as disclosed herein may be used on their own to maintain the sterility of the item of surgical equipment.

In one aspect of the present invention, a surgical draping system comprises a surgical drape; an area defined by a predetermined length and a predetermined width of the surgical drape; at least one tear line in the surgical drape; and a sterility maintenance element extending an entirety of the predetermined length of the drape above the at least one tear line; wherein the sterility maintenance element is selectively reconfigurable between a covering position wherein the sterility maintenance element covers the at least one tear line; and a non-covering position wherein the sterility maintenance element is separated along the at least one tear line and longitudinally effaced lateral sides of the surgical drape separate and fall away from a sterile field in a sterile fashion.

In embodiments, the surgical draping system may further comprise an outer drape forming the sterility maintenance element that is not integrally affixed to the surgical drape.

In embodiments, the surgical draping system may further comprise a dust cover in communication the surgical drape; a Z-shaped fold located beneath the dust cover; an intersection point where the dust cover is releasably connected to the Z-shaped fold; a first tear line where the dust cover connects to the Z-shaped fold at the intersection point; and a second tear line located at an edge of the Z-shaped fold.

In embodiments, the surgical draping system may further comprise an inferior drape comprising a first inferior drape sheet having a first edge; a second inferior drape sheet having a second edge located adjacent the first inferior drape sheet; and a separable attachment releasably connecting the first inferior drape section to the second inferior drape section; and a dust cover located above the inferior drape. The first edge of the first inferior drape sheet may, but need not, be laterally spaced from the second edge of the second inferior drape sheet in the covering position. The first edge of the first inferior drape sheet may, but need not, overlap the second edge of the second inferior drape sheet in the covering position.

In embodiments, the sterility maintenance element may further comprise at least one sheet having a first end, a second end, and a middle section between the first end and the second end; the at least one tear line may be formed in the middle section; the at least one sheet may be rolled concentrically about the at least one tear line in the covering position; and the at least one sheet may be unrolled about the at least one tear line to the non-covering position.

In embodiments, the surgical draping system may further comprise a peel-away flap cover extending along at least a portion of the predetermined length located above the tear line.

In another aspect of the present invention, a surgical draping system comprises a surgical drape comprising at least two drape sheets; an area defined by a predetermined length and a predetermined width of the surgical drape; and a sterility maintenance element extending an entirety of the predetermined length; wherein the sterility maintenance element is selectively reconfigurable between a covering position wherein the sterility maintenance element covers lateral sides of the at least two drape sheets; and a non-covering position wherein the sterility maintenance element is separated at lateral sides of the surgical drape, which separate and fall away from a sterile field in a sterile fashion.

In embodiments, the surgical draping system may further comprise a first drape sheet having a first lateral side; and a second drape sheet having a second lateral side positioned adjacent to the first lateral side; wherein the first drape sheet and the second drape sheet are rolled concentrically together where the first lateral side meets the second lateral side in the covering position; and wherein the first drape sheet and second drape sheet are unrolled about the first lateral side and the second lateral side to the non-covering position.

In embodiments, the surgical draping system may further comprise a first drape sheet having a first lateral side; and a second drape sheet having a bottom section, a top section, and a leading edge located between the bottom section and the top section; wherein the bottom section overlaps a portion of the first drape in the covering position; and wherein the top section is pulled away from the first drape to the non-covering position.

In embodiments, the surgical draping system may further comprise at least one perforated strip extending along at least a portion of the at least two drape sheets along the predetermined width.

In embodiments, the surgical draping system may further comprise a peel-away flap cover extending along at least a portion of the predetermined length.

In another aspect of the present invention, a method for maintaining sterility of a sterile surface comprises covering the sterile surface with a draping system, the draping system comprising a surgical drape, having an area defined by a predetermined length and a predetermined width; and a sterility maintenance element, extending an entirety of the predetermined length of the drape; wherein the sterility maintenance element is adapted to be positioned to maintain a sterile field; wherein the sterility maintenance element is selectively reconfigurable between a covering position and a non-covering position; and wherein the sterility maintenance element is adapted to be reconfigurable to the non-covering position to allow the surgical drape to be separated from the sterile field in a sterile fashion.

In embodiments, the method may further comprise separating a first tear line at an intersection point releasably connecting a dust cover and a Z-shaped fold; and separating a second tear line located at an edge of the Z-shaped fold.

In embodiments, the method may further comprise moving a dust cover away from a separable attachment releasably attaching a first inferior drape to a second inferior drape; and separating the separable attachment to disengage the first inferior drape from the second inferior drape.

In embodiments, the method may further comprise wrapping a portion of the surgical drape into a roll section; and unrolling the portion of the surgical drape about at least one tear line to the non-covering position.

In embodiments, the method may further comprise removing a peel-away flap cover extending along at least a portion of the predetermined length located above a perforation.

In embodiments, the method may further comprise disengaging at least one perforated strip that extends along at least a portion of the surgical drape along the predetermined width.

In embodiments, the method may further comprise removing a peel-away flap cover that extends along at least a portion of the predetermined length.

In another aspect of the present invention, a surgical drape for maintaining the sterility of a sterile surface comprises a surface area defined by a predetermined length and a predetermined circumference; an outer portion, comprising an open end or mouth at an end of the predetermined length; an inner portion; a perforation, disposed about the entire circumference of the surgical drape at effacing edges of the outer and inner portions, circumferentially surrounding at least a portion of the sterile surface; and a Z-fold pleat, disposed about the entire circumference of the surgical drape, overlying and maintaining sterility of the perforation, wherein the drape is configured to separate along the perforation, thereby separating the outer and inner portions, when a pulling force is applied to an end of the inner portion opposite the perforation, such that the effacing edge of the outer portion moves generally toward the open end or mouth and the effacing edge of the inner portion moves generally away from the open end or mouth.

In embodiments, the surgical drape may further comprise a selectively breakable tab securing the outer and inner portions to each other.

In embodiments, the surgical drape may further comprise a handle to aid a user in applying the pulling force.

In embodiments, the end of the inner portion opposite the perforation may be substantially closed and the drape may thus take the general shape of a bag.

In embodiments, the end of the inner portion opposite the perforation may be substantially open and the drape may thus take the general shape of a tube.

In embodiments, the surgical drape may further comprise a cuff or pocket disposed at the open end or mouth.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE DRAWINGS

The accompanying drawings, which are incorporated in and constitute a part of the specification, illustrate embodiments of the disclosure and together with the general description of the disclosure given above and the detailed description of the drawings given below, serve to explain the principles of the disclosures.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

FIG. 15C is yet another end view depicting a feature of a draping device;

FIGS. 45A through 45C are illustrations of possible modifications of the Z folds illustrated in, e.g., FIGS. 14A through 16, according to embodiments of the present disclosure.

DETAILED DESCRIPTION OF THE INVENTION

Figures 1A, 1B, 1C, 1D:
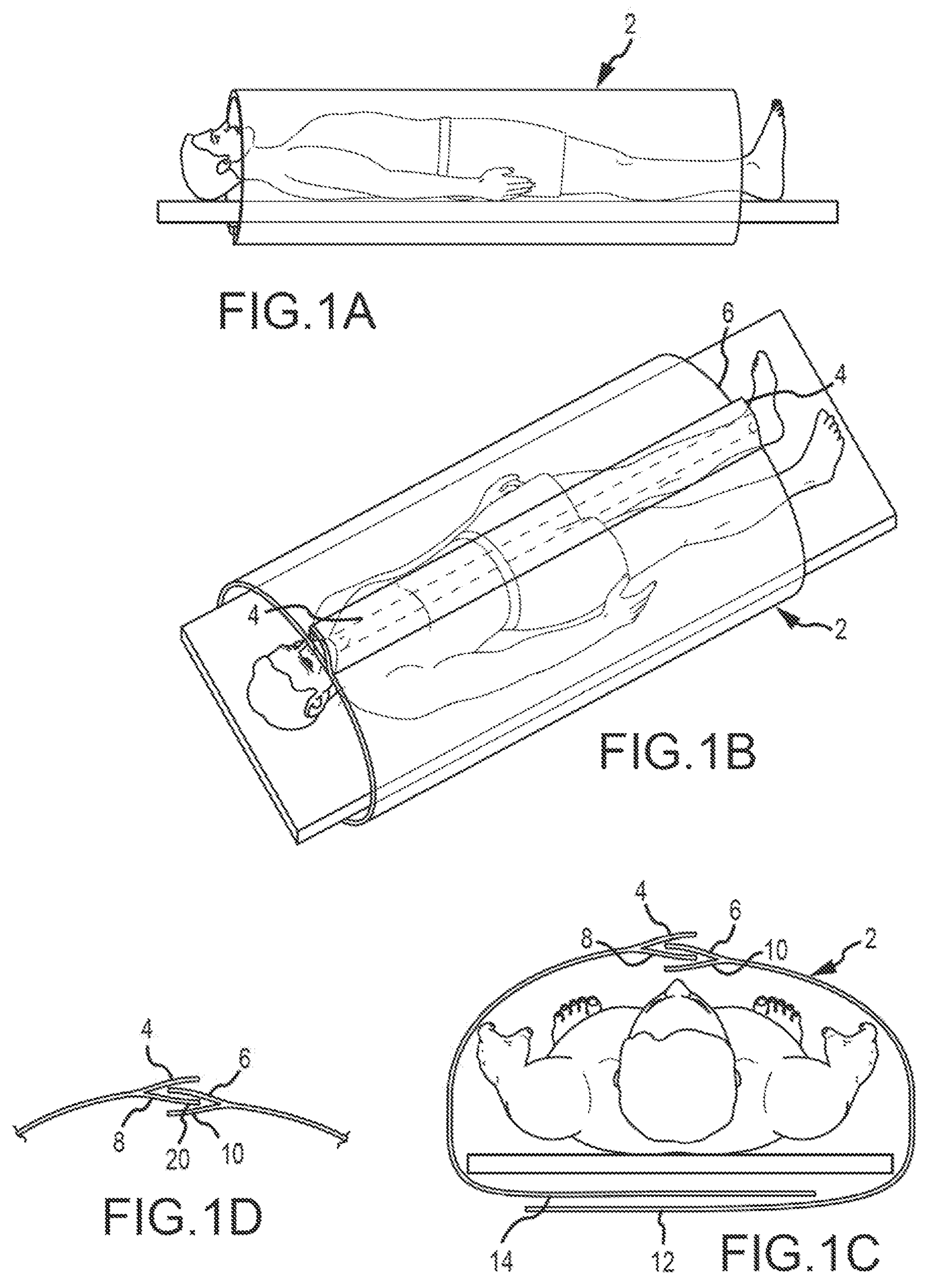
FIG. 1A is a side elevation view of a patient with a draping device according to one embodiment of the present disclosure.
FIG. 1B is a top perspective view of the draping device shown in FIG. 1A.
FIG. 1C is an end view of the draping device shown in FIG. 1A.
FIG. 1D is a partial sectional view of the draping device shown in FIG. 1A.

By way of providing additional background, context, and to further satisfy the written description requirements of 35 U.S.C. § 112, the following references are incorporated by reference in their entireties for the express purpose of explaining the nature of the surgical procedures referred to herein and to further describe the various tools and other apparatus commonly associated therewith: U.S. Pat. No. 6,309,395 to Smith et al.; U.S. Pat. No. 6,142,998 to Smith et al.; U.S. Pat. No. 7,014,640 to Kemppanien et al.; U.S. Pat. No. 7,406,775 to Funk, et al.; U.S. Pat. No. 7,387,643 to Michelson; U.S. Pat. No. 7,341,590 to Ferree; U.S. Pat. No. 7,288,093 to Michelson; U.S. Pat. No. 7,207,992 to Ritland; U.S. Pat. No. 7,077,864 Byrd III, et al.; U.S. Pat. No. 7,025,769 to Ferree; U.S. Pat. No. 6,719,795 to Cornwall, et al.; U.S. Pat. No. 6,364,880 to Michelson; U.S. Pat. No. 6,328,738 to Suddaby; U.S. Pat. No. 6,290,724 to Marino; U.S. Pat. No. 6,113,602 to Sand; U.S. Pat. No. 6,030,401 to Marino; U.S. Pat. No. 5,865,846 to Bryan, et al.; U.S. Pat. No. 5,569,246 to Ojima, et al.; U.S. Pat. No. 5,527,312 to Ray; U.S. Pat. No. 6,314,959 to Griesbach et al.; and U.S. Pat. Appl. No. 2008/0255564 to Michelson.

U.S. Patent Publication Nos. 2010/0186754 to Carrez et al., 2010/0192960 to Rotolo, and 2019/0060020 to Toure, and PCT Application Publication 2018/183794 to Bemman et al., are hereby incorporated by reference in their entireties herein for the express purpose of providing description of various materials and methods of production for surgical drapes.

According to varying embodiments disclosed herein, a draping device and method for using the same is described. As one of or ordinary skill in the art will appreciate, embodiments of the present disclosure may be constructed of materials known to provide, or predictably manufactured to provide the various aspects of the present disclosure. These materials may include, for example, cotton, paper, silk, polyethylene, and polyester. These materials may also include, for example, carbon fiber, ABS plastic, polyurethane, rubber, latex, synthetic rubber, and other fiber-encased resinous materials, synthetic materials, polymers, and natural materials. In another embodiment, some or all elements of the device, or portions of some or all of the elements, are substantially transparent.

Embodiments of the present disclosure present several advantages over the prior art including, for example, the efficacy of the procedure, the sterility of the procedure, the lower risk of infection, etc. Further, the advantages of the device according to various embodiments disclosed herein allows improved viewing of the area intended for surgery. Thus, the presence of one or more transparent areas is one aspect of this disclosure Referring now to FIGS. 1A-14, several embodiments of the present invention are shown.

Referring in particular to FIGS. 1A-9C, the drape according to one embodiment (RWD1) has been designed to meet all basic design requirements considered to be mandatory for operating room use. Multiple alternatives are shown for RWD1.

The drape shown in FIGS. 1A-9C, according to varying embodiments, includes a surgical drape, which may be made of a variety of different materials described herein. The surgical drape is of sufficient length and width to encompass a human patient and/or an operating table and associated wires, cables, trays, tools, and instruments, including but not limited to 3D radiographic equipment, which is used during the course of a sterile surgical procedure. The drape according to one embodiment comprises at least one location where the drape is temporarily secured and also provides a sterile field about the at least one longitudinal access, yet may be sterilely separated about this longitudinal access by one of a variety of mechanisms and configurations of the surgical drape. As shown in FIGS. 2A-D this longitudinal sterile separation may be accomplished by a series of overlapping and temporarily attached draping segments (see 4, 6, 8, 10 in FIG. 1C), which is referred to hereinafter as the 'double-underbite' configuration. This double-underbite may further comprise at least one serrated portion of the surgical drape which may become detached by pulling or tearing the surgical drape material at the serrated location. Preferably, as shown in FIG. 1D, this serrated location is not exposed to non-sterile equipment.

FIGS. 1A-1D depict a drape 2 according to one embodiment wherein portions of the drape 2 comprise overlapping features 4, 6, 8, 10 comprising a selectively detachable portion. Overlapping features 4, 6, 8, 10 generally define a sterile area 20 that may be detached in order to remove the drape 2 from a patient and/or workspace.

Figure 2A:
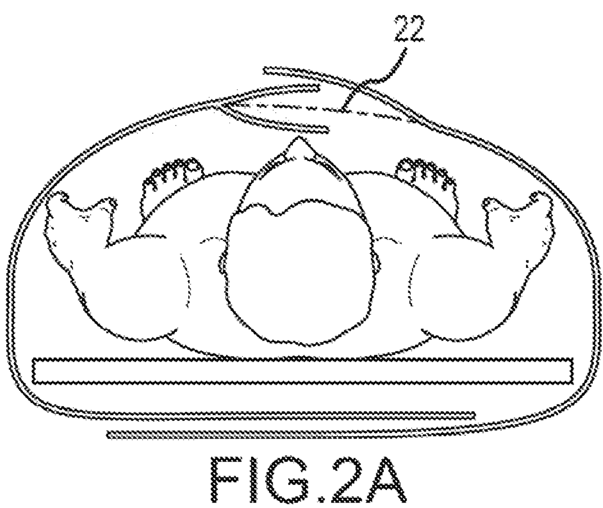
FIG. 2A is an end view of a patient with a draping device according to one embodiment of the present disclosure.
Figure 2B:
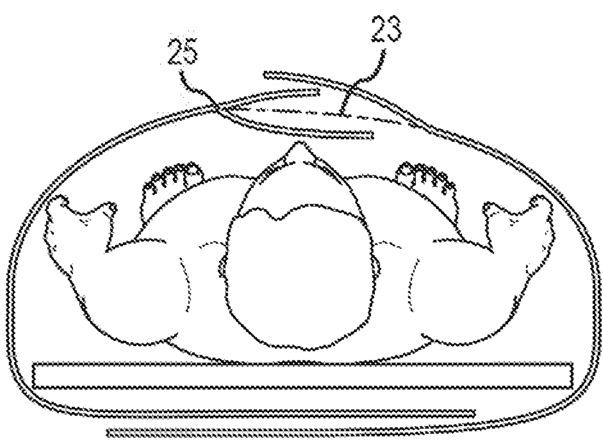
FIG. 2B is another end view of the patient with a draping device according to one embodiment of the present disclosure.
Figure 2C:
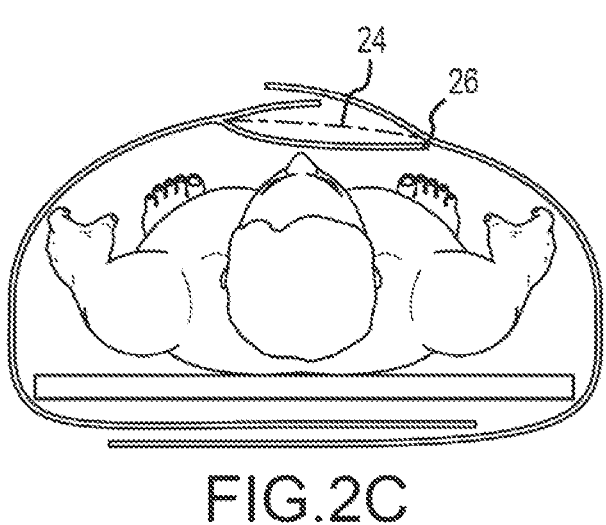
FIG. 2C is another end view of the patient with a draping device according to one embodiment of the present disclosure.

According to alternate embodiments, this serrated portion of the surgical drape may include serrated portions in multiple locations (see FIG. 2A, 22). In other embodiments, the surgical drape may include at least one zip strip (FIG. 2B, 25) in addition to a serrated portion of the drape (FIG. 2B, 23, FIG. 2C, 24), which may also become separated from the adjoining portion of the surgical drape. According to the embodiment shown in FIG. 2C, the zip strip may be located on an alternative or additional location of the drape relative to the patient (see FIG. 2C, 26).

Other aspects of the invention are shown in FIG. 1C, which includes an under-table wrapping element 12, 14, which is achieved by including fastening devices with each of the overlapping lower portions of the surgical drape 2 where those lower portions overlap 12, 14. A variety of different fastening devices are contemplated for use with the present disclosure, including but not limited to adhesive devices, pins, clips, snaps, hook and loop devices, velcro, magnetic strips, etc.

This design offers navigation readability of a reference frame through sterile overlying plastic cover (or lens), contains an under table wrapping component for easy positioning of 3D radiographic device (or C-arm, O-arm) to and from field, and allows for a simple two step sterile separation of approximated longitudinal sides (e.g. 'underflap' and 'double underbite'). The RWD1 preferably includes a plastic drape and/or has a plastic component (or lens) for navigation readability.

RWD1 variants may comprise transparency to light and/or transmissivity to various known radiographic devices (see FIGS. 1A-4B). For example, the entire drape may be made of transparent and/or translucent plastic. Alternatively, a built-in clear plastic (or other transparent material) section of drape may be provided to allow for readability of the reference frame by navigation technology (see FIGS. 3A-B, ref. no. 30). This plastic section is situated to accommodate for various positions of the reference frame on the patient to include cervical, thoracic, lumbar, as well as bilateral sacroiliac. The plastic region may further accommodate a variety of anatomic placement of the reference frame by one of several mechanisms, by way of example but not limitation: longitudinal sterile separation extending most if not the entire length of the drape.

Figure 3A:
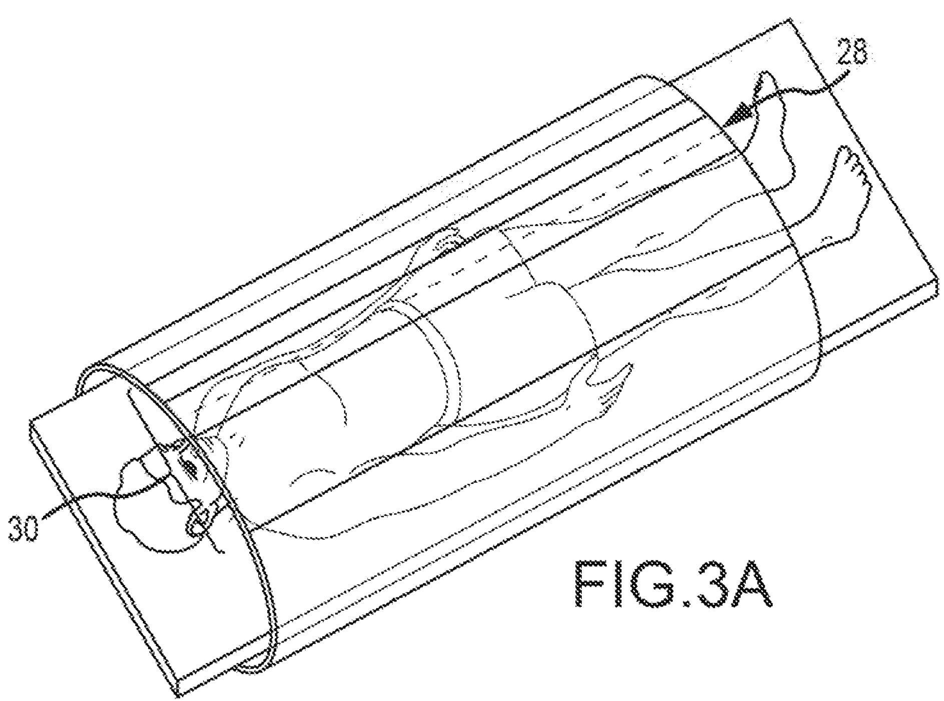
FIG. 3A is a top perspective view of the draping device according to one embodiment of the present disclosure.
Figure 3B:
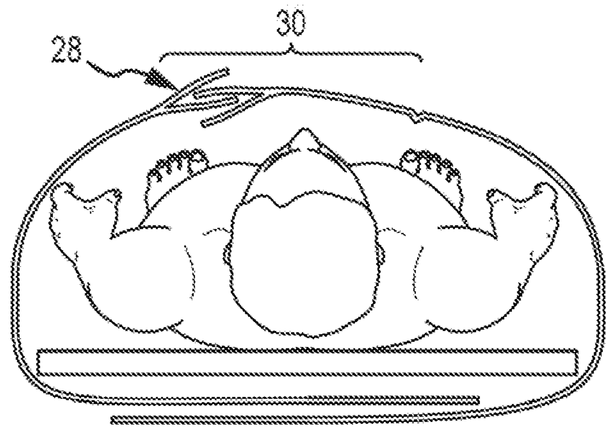
FIG. 3B is an end view of the draping device shown in FIG. 3A.
Figure 4A:
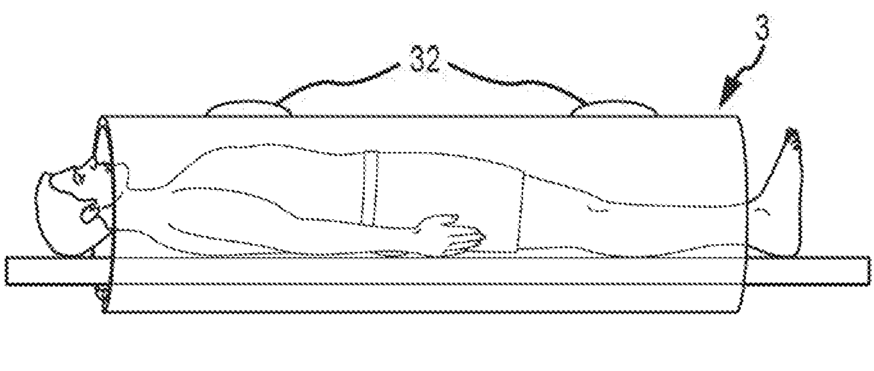
FIG. 4A is a side elevation view of a patient with a draping device according to one embodiment of the present disclosure.
Figure 4B:
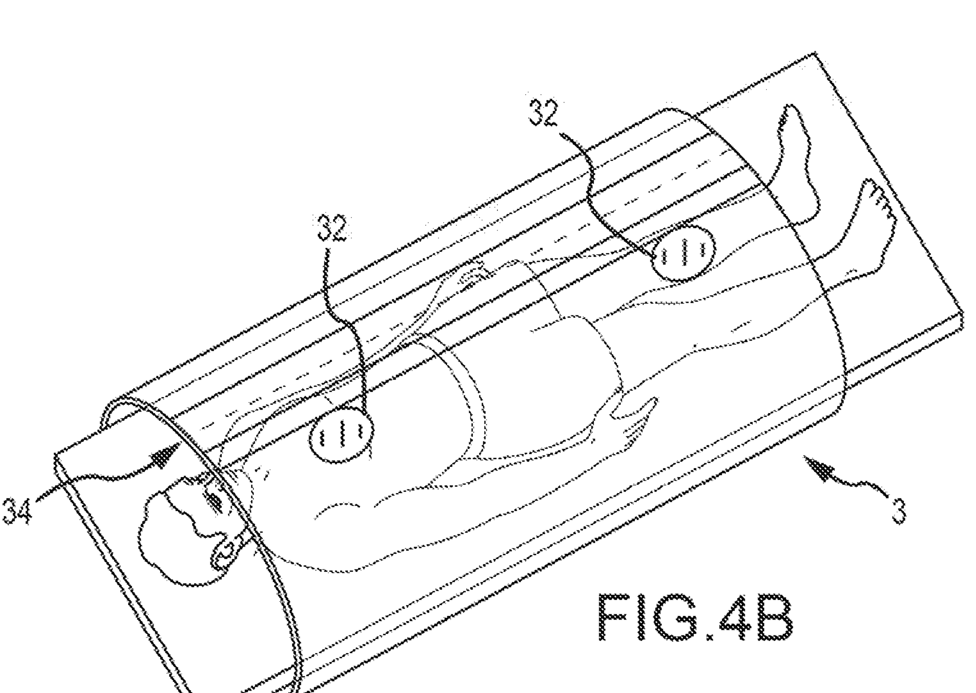
FIG. 4B is a top perspective view of the draping device shown in FIG. 4A.

FIGS. 3A-B depict one embodiment of the drape wherein a separable portion 28 adapted to maintain a sterile field generally extends along a longitudinal length of the drape. A transmissive or translucent portion 30 comprising at least a portion of the width of the drape and extending along the length of the drape is provided. It will be expressly understood that this portion 30 may be of various dimensions and, in alternative embodiments, does not extend along the entire width or length of the drape.

In various embodiments, one or more transparent portions or lenses may be placed at various locations (FIGS. 4A-B, 32) on the drape 3 to accommodate for different anatomic positions. Plastic may be incorporated into just a portion of the drape (either inferior or superior) as shown in FIG. 3B, yet with the ability to reverse the orientation of the drape when placing it thus again accommodating for different anatomic positions. Such concepts also apply when accommodating for use of the reference frame in ENT procedures, brain surgery, and pelvic surgery among other types of surgeries utilizing navigation technology. Although FIGS. 1A-4B are depicted with a 'double underbite' separation, it is expressly understood that any of the other separation designs including but not limited to the 'single-underbite' and 'Z-Shaped' separation designs described herein may be substituted.

Referring to FIGS. 1A-3B, the draping device preferably comprises at least one sterile separation element, which may extend longitudinally the entire or less than the entire length of the draping device. As shown in the Figures, the superior aspect of the separation element falls on the inferior aspect of the separation element, thereby overlapping and protecting the separation seam and the unsterile edge of the draping device from contacting the underlying sterile field.

Sterile separation of longitudinal effaced sides (see FIGS. 1A-8D) provides several advantages: it has the unique ability for the two longitudinally effaced lateral sides to separate and fall away to their ipsilateral side in a simple (one or two step) sterile fashion. Thus, as shown in the appended drawing figures, multiple unique designs for a surgical drape are disclosed that allow preservation of sterile edges of both separating sides, including the 'double underbite' (depicted in FIGS. 1A-4B), 'peel away flap cover' (FIGS. 5A-C, 36), 'single underbite' (FIGS. 6A-C, 38), 'curled lip' (FIGS. 7A-D, 40*a*, 40*b*), and 'underflap' (FIGS. 8A-D, 50). Various means of initial connection are utilized, including but not limited to the following: serration, static, tacking, seam weld, zip strip, adhesive, tape/steristrip, among others listed herein.

Figures 8A, 8B, 8C, 8D:
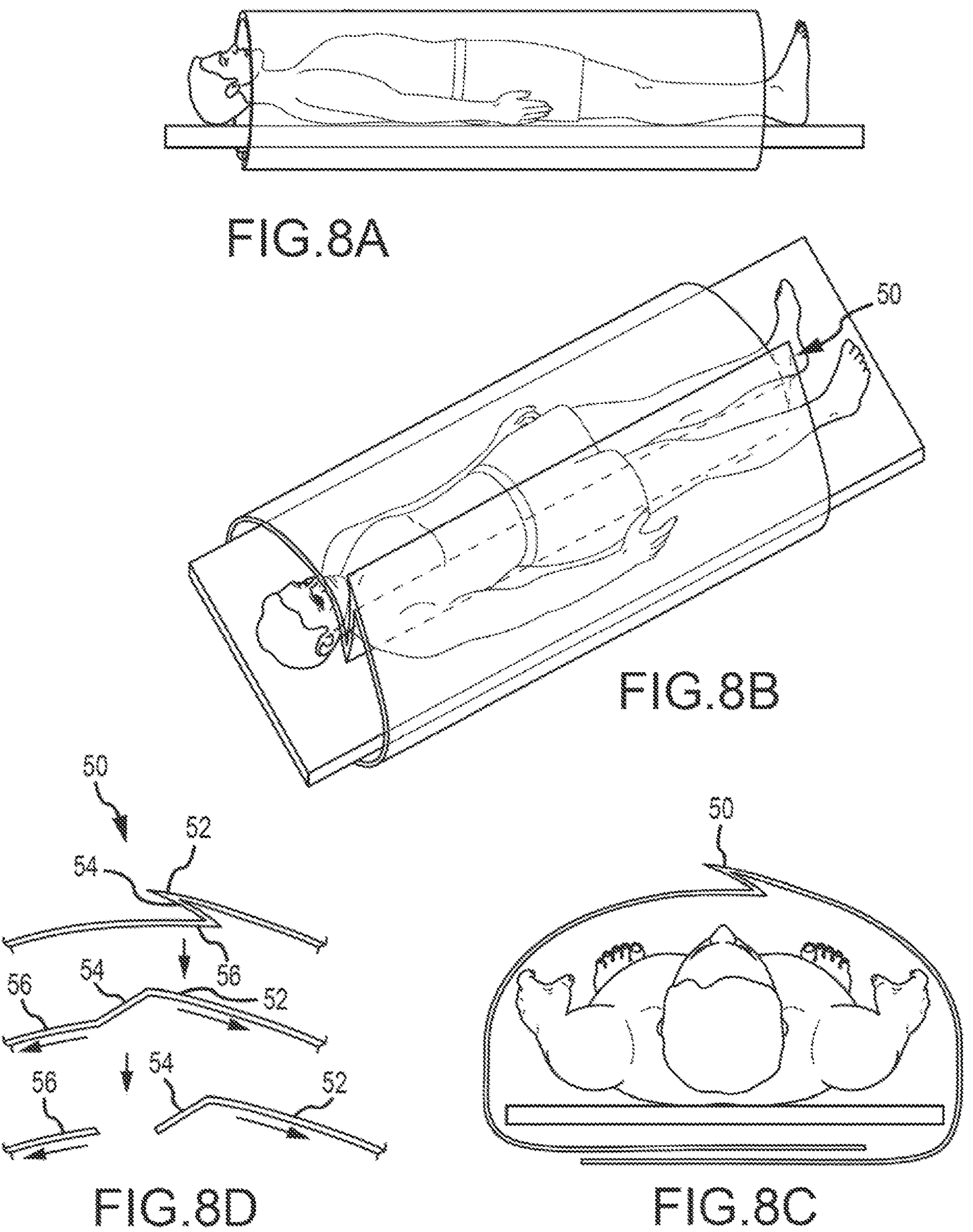
FIG. 8A is a side elevation view of a draping device according to one embodiment of the present disclosure.
FIG. 8B is a top perspective view of the draping device shown in FIG. 8A.
FIG. 8C is an end view of the draping device shown in FIG. 8A.
FIG. 8D is a sectional view of the draping device shown in FIG. 8A.
Figure 9A:
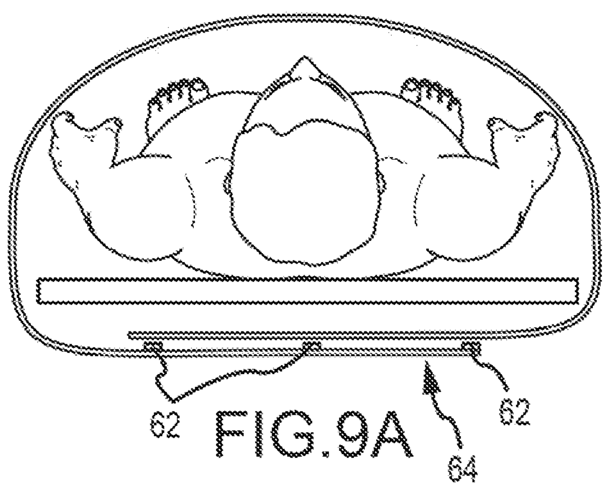
FIG. 9A is an end view of a draping device according to one embodiment of the present disclosure.
Figure 9B:
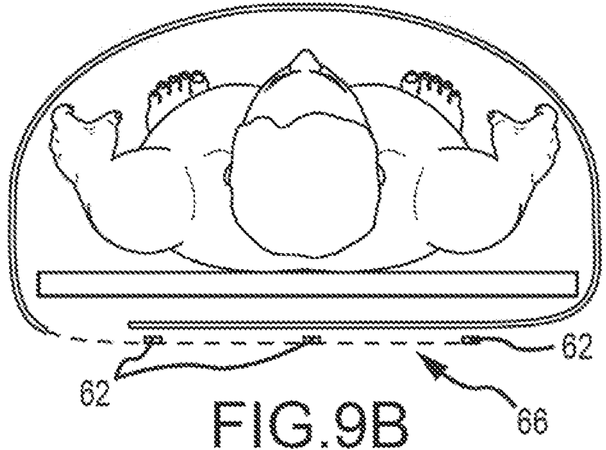
FIG. 9B is another end view of a draping device according to one embodiment of the present disclosure.
Figure 9C:
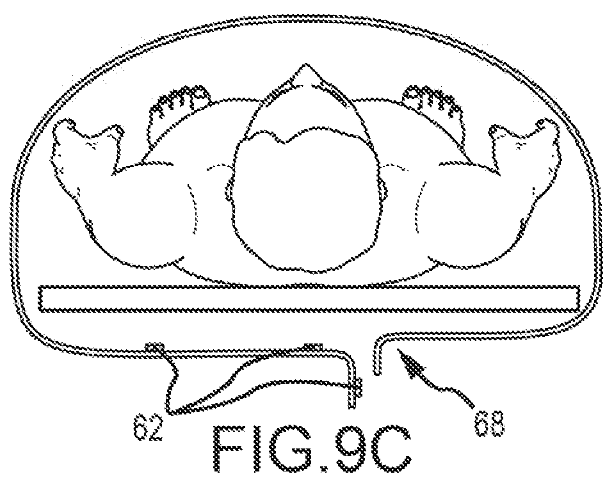
FIG. 9C is another end view of a draping device according to one embodiment of the present disclosure.
Figure 10A:
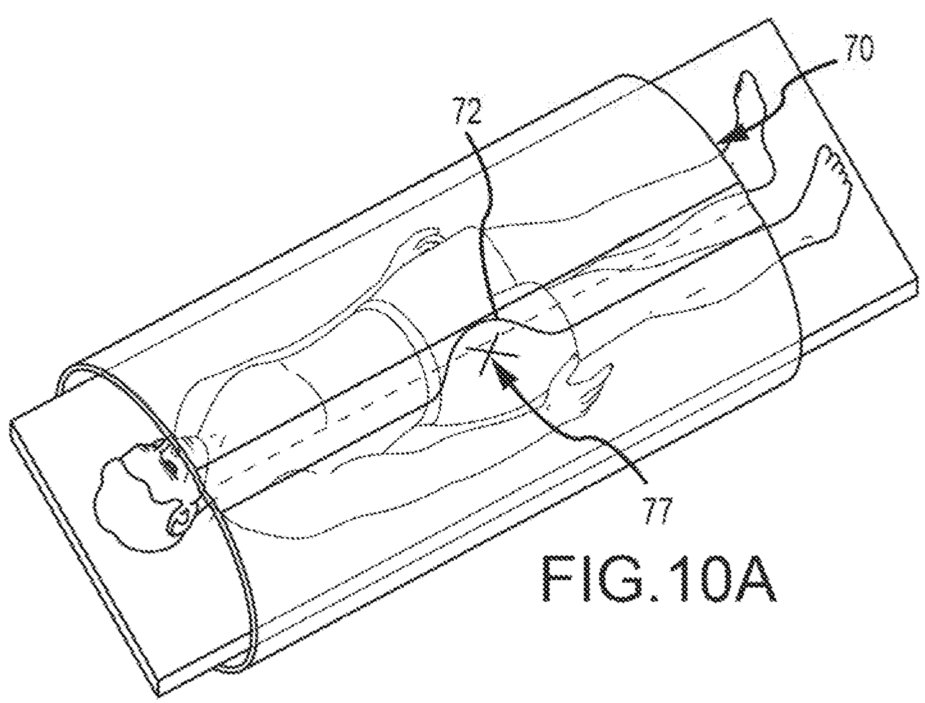
FIG. 10A is a top perspective view of a draping device according to one embodiment of the present disclosure.
Figure 10B:
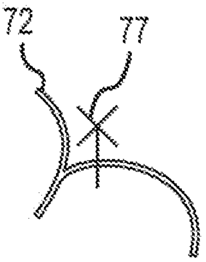
FIG. 10B is an end view of the draping device shown in FIG. 10A.

FIGS. 8A-D depict an embodiment wherein the underflap design 50 is provided. As shown, a separation area may be covered by a pleat 52 which covers and/or protects additional areas of the drape 54, 56 in a first position. The underflap may be opened and separated along a predetermined tear line or separation point as described herein. In at least one embodiment, a longitudinal score line or separation point is disposed below the pleat 52 as shown in FIG. 8D.

The under-table wrapping component (see FIGS. 9A-C) has the following features: each lateral side hanging over the table may be capable of being connected underneath the table by any of a variety of means 62, thereby enclosing hanging wires, catheters, and other medical equipment commonly located under the OR table and at risk of getting 'snagged' by the entering and exiting 3D radiographic device (or C-arm). The two hanging sides 66, 68 of the drape may connect under the table by any of various means 62, including but not limited to the following: velcro, adhesive, static, buttons, cloth (or other material) ties among others. Straps with such connections may further or alternatively be utilized. These various connective possibilities are adjustable and configurable in quantity and location, and thus accommodate for different overall circumferences as table frame size, patient size, and arm positioning all can possibly alter this measurement. It is to be expressly understood that the terms "under-table wrapping component" and/or "under-table wrapping element" may simply refer to sides 66, 68 of the surgical drape themselves, without a separate connecting means 62.

Referring now to FIGS. 10A-13B, another embodiment of the surgical drape (RWD2) has been designed to meet all basic design requirements considered to be mandatory for operating room use. RDW2 variants contain the same essential design characteristics as RWD1 yet adds the ability to provide the surgeon the option of direct exposure of a reference frame 77 (with minimal potential sterility compromise). This specific design provides all three major aspects of RWD1 described above, but provides the option of leaving the frame exposed directly to the navigation device if desired by the surgeon. As shown, a portion 72 of the drape may be gusseted or extended in a manner that allows for selective displacement of the portion 72 without disrupting or contaminating a remainder of the drape. Accordingly, a portion of an underlying patient may be exposed when access is required or desired for various procedures without complete removal of the drape.

As is the case with RWD1, more than one design variant is disclosed below. (See FIGS. 10A-13B). The surgeon may allow for direct exposure after the drape has been placed with complete coverage of the underlying sterile field (as the initial design provides in RWD1). The direct exposure option keeps the underlying field sterile with the only exception being that of the protruding neck and reference frame itself. If the surgeon believes the accuracy of information is comprised by the overlying plastic cover or lens, he/she may decide to utilize this 'direct' option at the slight potential compromise of sterility. The surgeon, if executing this option, still benefits from the temporary sterile coverage of the rest of the field. The under-the-table wrapping feature (to make positioning of the radiographic device safer, quicker, and easier), and the efficiency of the removal process as both sides of the drape seamlessly fall away to their respective sides is further incorporated with the surgical drape in this embodiment.

In the embodiment referred to as RWD2 (as depicted in FIGS. 10A-13B), the reference frame 77 is placed through the drape 70 by separating a small portion 72 of the serrated connection of the two opposing sides. In the 'direct' version (meaning direct visualization of the reference frame by the navigation monitor), the overlying plastic slip 72 is partially pulled back (depicted in FIGS. 10A-11C and 13A-B) or a component of the cover slip is reflected back (depicted in FIG. 12). Given the undraped radiographic device above, there exists a potential breach in sterility and thus this option must be considered in a risk-benefit analysis by the surgeon prior to execution. Under-table or below-patient wrapping features as shown and described herein are also incorporated into various embodiments of the RWD2. As shown and described in FIGS. 9A-C, fasteners 62, 66 may be provided at or near opposing ends of the drape to secure the opposing ends to one another or additional objects. As an upper or patient-side portion of the drape comprises features for separating and/or detaching the drape from a patient, fasteners 62, 66 may be selectively reversible/detachable fasteners, or may permanently affix to one another.

Figure 11A:
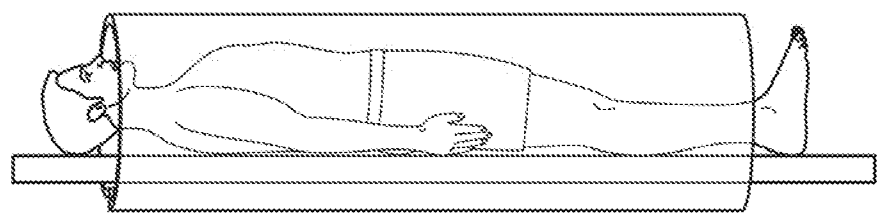
FIG. 11A is a side elevation view of a draping device according to one embodiment of the present disclosure.
Figure 11B:
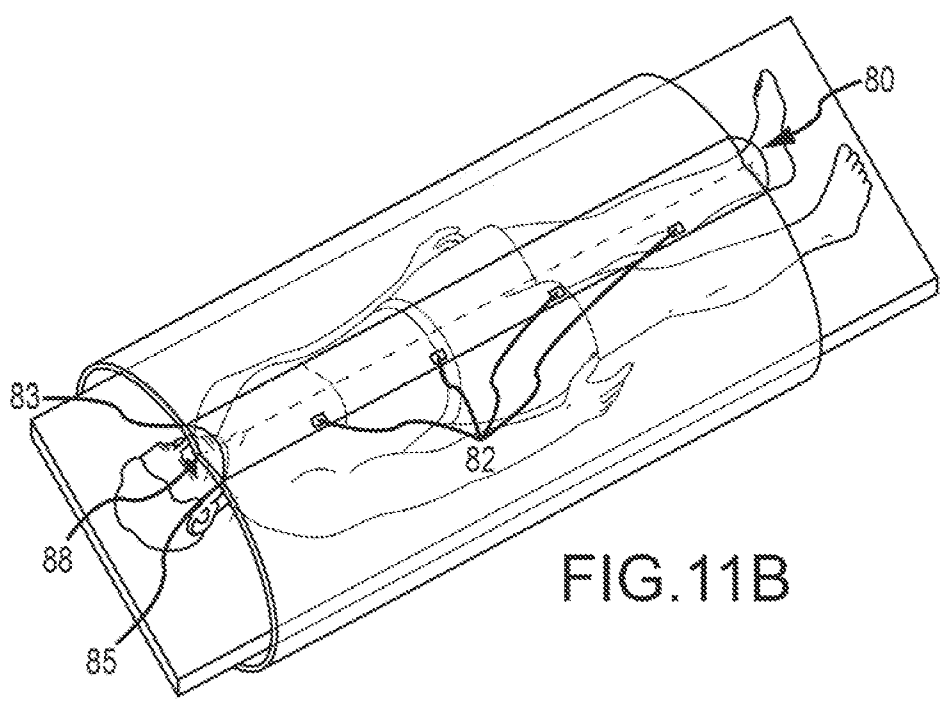
FIG. 11B is a top perspective view of the draping device shown in FIG. 11A.
Figure 11C:
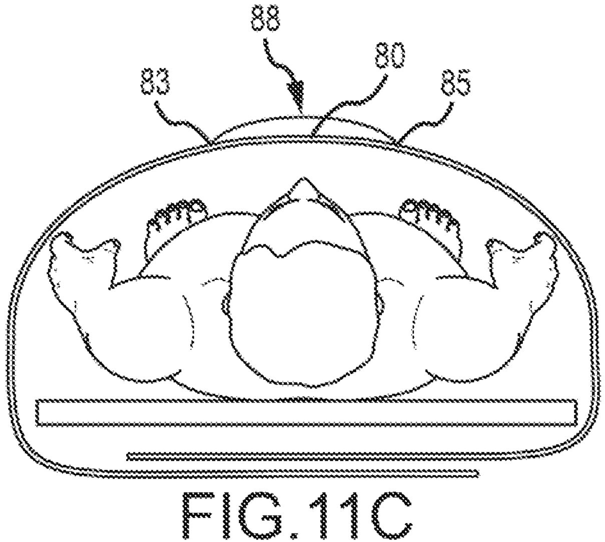
FIG. 11C is an end view of the draping device shown in FIG. 11A.

FIGS. 11A-C depict yet another embodiment of the present invention where one or more fasteners 82 are provided along a longitudinal length of an upper portion of the drape 80. Selectively detachable portions and translucent or transmissive materials 88 may be provided in addition to various fasteners 82.

Figure 12:
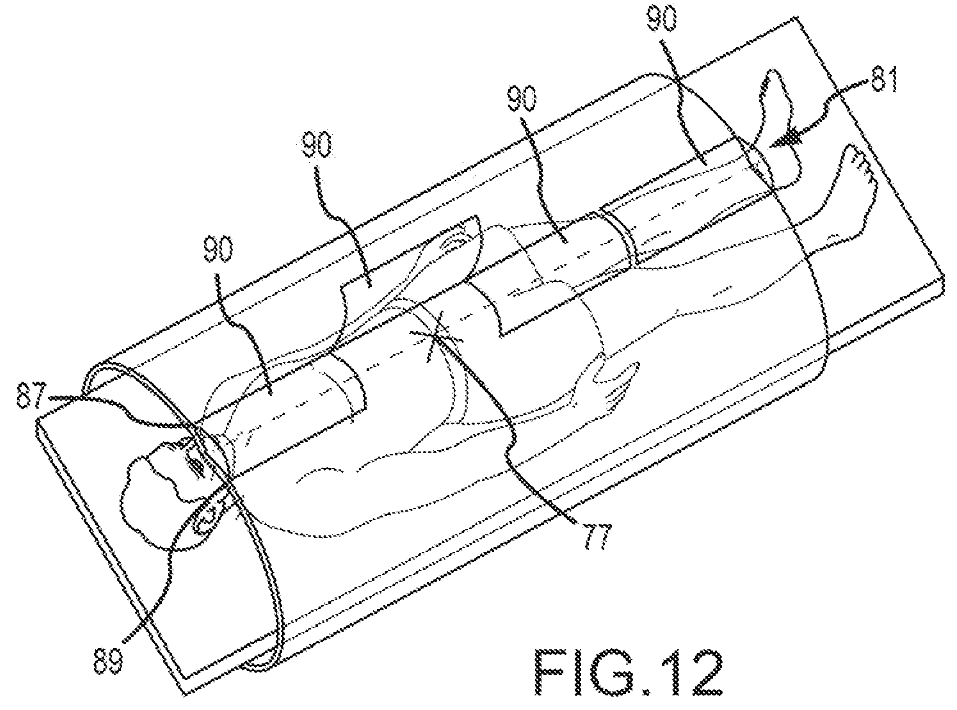
FIG. 12 is a top perspective view of the draping device according to one embodiment of the present disclosure.

FIG. 12 depicts an embodiment of a drape 81 provided with a plurality of hinged portions 90 which allow for selective access to various regions or objects disposed under the drape.

Figure 13A:
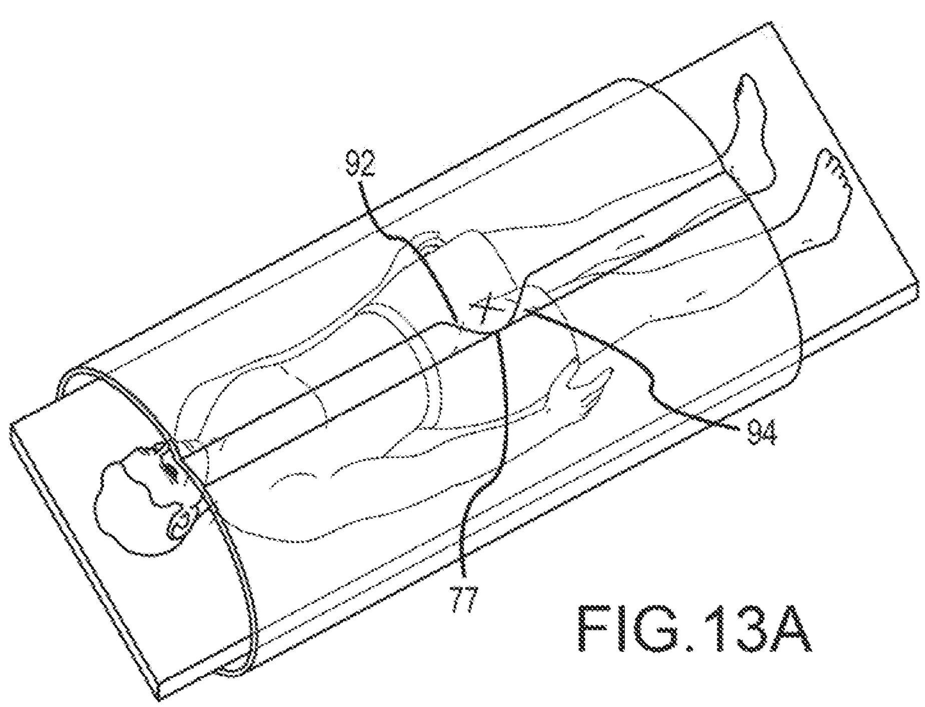
FIG. 13A is a top perspective view of a draping device according to one embodiment of the present disclosure.
Figure 13B:
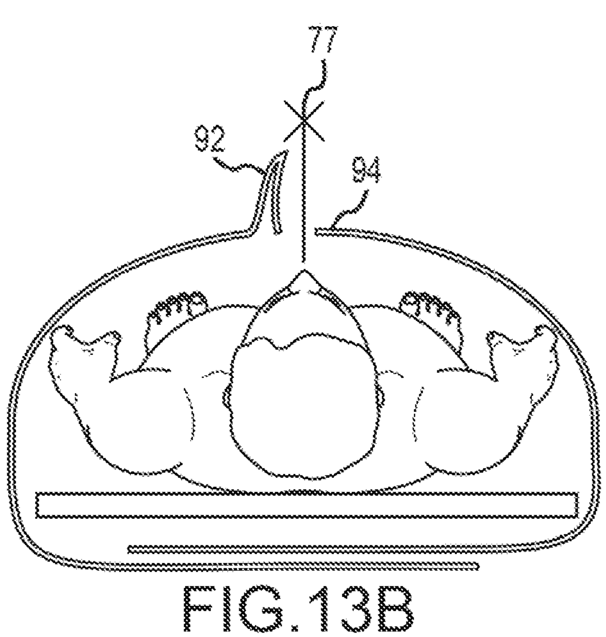
FIG. 13B is an end view of the draping device shown in FIG. 13A.

FIG. 13A-B depict yet another embodiment wherein a hinged portion 92 and corresponding flap 94 are provided for selective access. These features 92, 94 allow for access to a surgical workspace and/or exposure of a reference frame 77.

For the purpose of streamlining the present disclosure, Applicants hereby incorporate by reference U.S. Provisional Patent Application Nos. 61/352,045 and 61/357,637 herein in their entireties. The drape disclosed in these two prior filed provisional patent applications have been designed to meet all basic design requirements considered to be mandatory for operating room use. For those surgeons who remain highly concerned about the potential inaccuracy of the readability of the reference frame by the navigation monitor through a transparent plastic cover or lens for that matter, yet at the same time are unwilling to accept any potential slight breach in sterility (such as in RWD2 where reference frame is left exposed to overlying radiological device as an option), a unique alternate design to address such a concern is provided. This alternate design will be referred to as RWD4.

The RWD4 is a one piece customized disposable surgical drape to be used in any surgery that involves one of the following technologies: (1) stand alone non-draped 3D image acquisition device (requiring greater than 180 degrees of orbital rotation); and (2) image-guided navigation technology. This RWD4 drape accommodates a surgeon's preference, as it allows for both indirect (through plastic or lens) as well as direct navigation readability of the reference frame while the 3D acquisition is taking place.

This drape is different, however, from RWD2 in that in both instances (direct and indirect navigation readability of the reference frame) it maintains sterility of the field to include the protruding reference frame. This drape is modifiable in that the concepts may be adapted to accommodate different anatomical placements of the reference frame and/or various positions of the monitor.

This drape has utility in other surgeries (in addition to spine surgery) such as the pelvic trauma, brain surgery, ENT surgery among others. The 'Frame Hood Cover' is the unique aspect of RWD4 that is designed to cover and protect the reference frame (with attached neck) from the above non-draped (and thus unsterile) 3D radiological device (e.g. O-arm). It is made of a clear, thin plastic to allow navigation readability of the reference frame through the 'Frame Hood Cover' as the 3D data acquisition is taking place. At the same time, it allows for direct and open-air readability by the navigation monitor (rather than through the plastic) in that the 'Frame Hood Cover' is able to be partially open while concomitantly maintaining 'above the reference frame' protection from the directly overlying 3D radiographic device.

In embodiments, one or more additional features may be provided in or with the patient drapes illustrated in FIGS. 1A through 13B and/or other drapes according to the present invention. In particular, features may be provided that reduce the likelihood of overhanging or "dirty" (i.e. potentially contaminated) edges from being brought above the surface of the table during separation and removal of the drape and/or cause the drape to be inadvertently displaced prior to separation and removal. As a first non-limiting example, a drape of the present invention may be provided with one cinch or strap for each leg of the underlying table (in most embodiments, four straps for a four-legged operating table), thereby permitting operating room personnel to secure the drape to each leg of the table. As a second non-limiting example, a drape of the present invention may be provided with a "belt"-type cinch or strap that completely encircles the table when the drape is positioned over the patient and/or other drapes of the invention; such a cinch or strap can be fed through belt loops on a surface of the drape, and/or be adhered to itself using a tamperproof adhesive or similar connecting mechanism. As a third non-limiting example, a drape of the present invention may be provided with an elastic band, e.g. a rubber band, and one or more hooks, e.g. S-hooks, which may be used to secure one selected portion of the drape below the surface of the table to another selected portion of the drape below the surface of the table, or to the table itself or a portion thereof. In any one or more of the above examples, any one or more of a plurality of cinches, straps, bands, hooks, etc. may be configured to interconnect at a single point below the surface of the table; in this way, operating room personnel may be to engage or disengage such cinches, straps, bands, hooks, etc. in a single step. Further, in any one or more of the above examples, it may be desirable to provide such cinches, straps, bands, hooks, etc. in such a configuration as to allow the entire drape to fall to the floor of the operating room as a single unitary piece of material after separation of the perforation above the table; such a constructions allows for easier and more sanitary removal of the drape and greater safety (e.g. due to reduced tripping hazard) for operating room personnel.

Figure 14A:
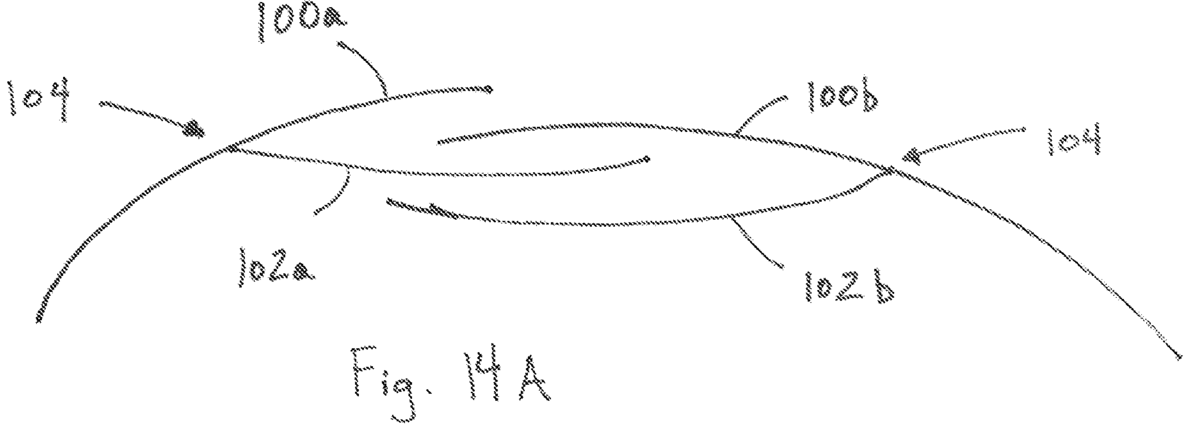
FIG. 14A is an end view depicting a feature of a draping device.
Figure 14B:
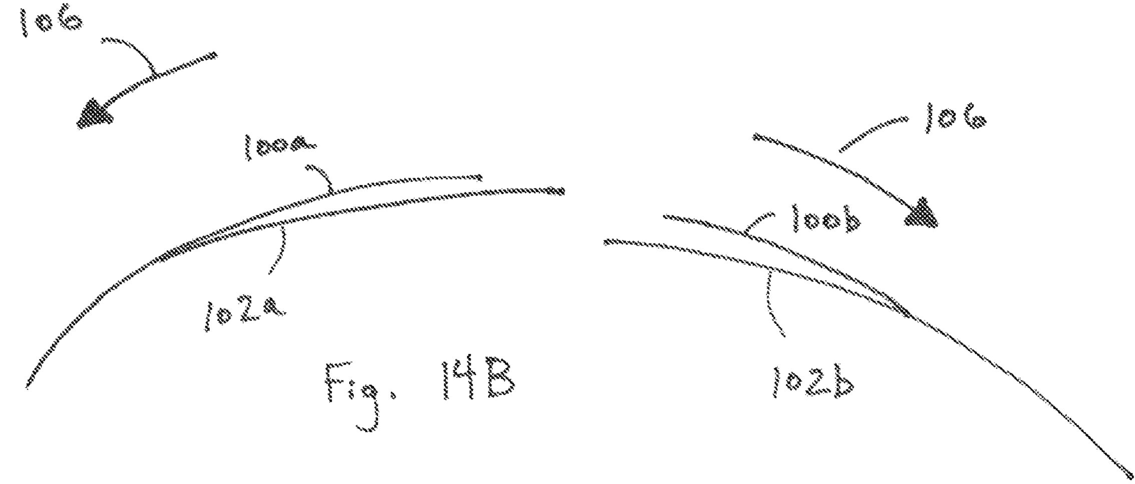
FIG. 14B is an end view depicting a feature of a draping device.

FIGS. 14A-B provide additional end views of yet another sterility maintaining feature that may be employed in various embodiments. As shown, a drape comprises upper 100*a* and lower 100*b* superior portions as well as upper 102*a* and lower 102*b* inferior portions. One or more separable portions and/or fasteners for securing the drape as described herein and as will be recognized by one of ordinary skill in the art may be provided. The drape may be separable at numerous different locations. For example, separable portion(s) may connect upper superior portion 100*a* to lower superior portion 100*b*, lower superior portion 100*b* to upper inferior portion 102*a*, upper inferior portion 102*a* to lower inferior portion 102*b*, and/or may be connected/provided at the intersections 104 of these features.

When the drape is separated and removed or allowed to fall, upper superior portion 100*a* will fall to upper inferior portion 102*a* and lower superior portion 100*b* will fall to lower inferior portion 102*b*. Accordingly, superior portions 100*a,b* which are exposed to various contaminants are prevented from contacting and/or contaminating a patient and/or a workspace by virtue of the dimensions and positioning of the inferior portions 102*a,b*. As shown, superior portions 100*a,b* cover the entire surface area of the inferior portions 102*a,b* in at least a first position of use. Contamination of inferior portions 102*a,b* from, for example, radiographic and imaging equipment is thus prevented. Upon separation and removal of the drape, contamination of the underlying workspace and/or patient is likewise prevented by inferior portions 102*a,b*.

FIG. 14B further depicts removal of the drape subsequent to detachment of a selectively securable feature and wherein portions of the drape are transmitted as shown by directional arrows 106. As shown, potentially contaminated upper and lower superior portions 100*a,b* are prevented from contacting a sterile space by upper and lower inferior portions 102*a,b*.

Figure 15A:
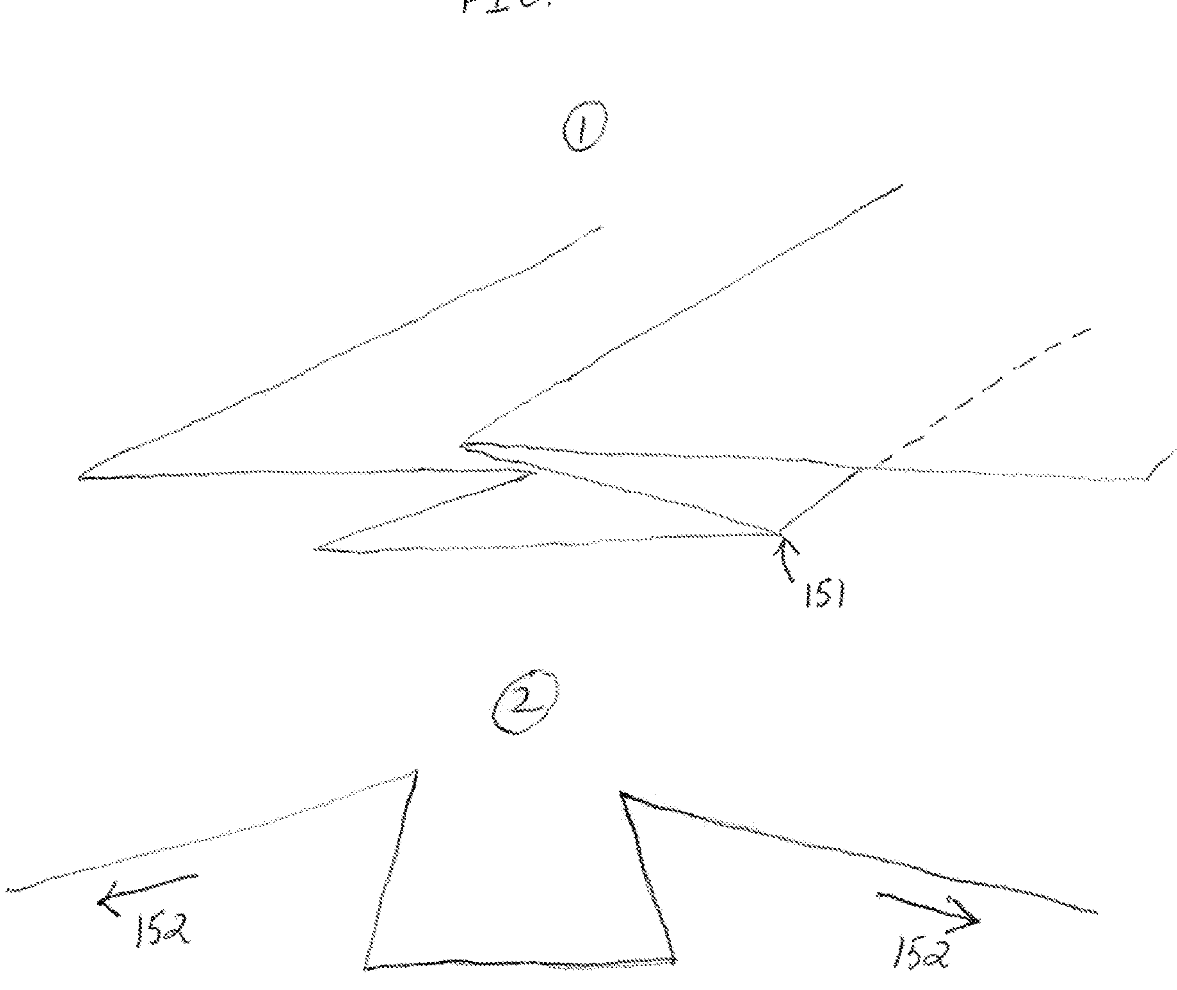
FIG. 15A is an end view depicting a feature of a draping device according to yet another embodiment.

FIG. 15A depicts end views of another sterility-maintaining surgical drape. As shown in FIG. 15A, a portion of the drape comprising a "double Z" flap orientation, which comprises at least one perforation 151 overlying the sterile field. A user applies a pulling force 152 to pull apart the two top portions of the "double Z" flap, and the drape portions separate along the perforation 151. The two halves of the drape may thus be pulled, or allowed to fall, over opposing sides of the sterile field without compromising the sterility of the sterile field. The "double Z" configuration of the drape shown in FIG. 15A maintains a sterile surface adjacent the perforation 151. Although a perforated separable drape is described in these embodiments, it is expressly understood that other means of providing a predetermined separable portion of the drape are included and considered within the scope of the invention. For example, a surface with scoring along the predetermined separable portion may be provided. As another example the drape may be comprised of a different material along the predetermined separable portion, wherein the different material comprises a characteristic which allows it to be torn or separated more easily than the material of the remainder of the drape.

Figure 15A:
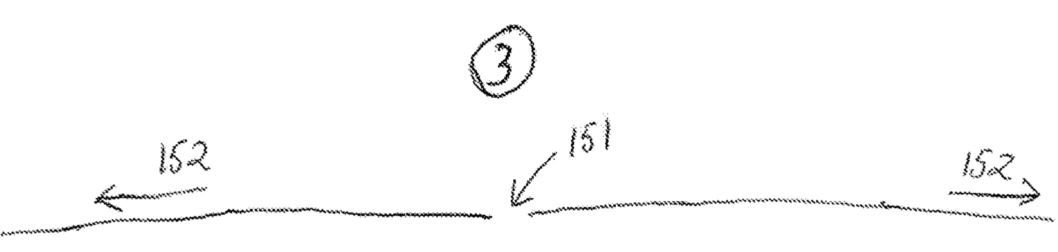
Figure 15B:
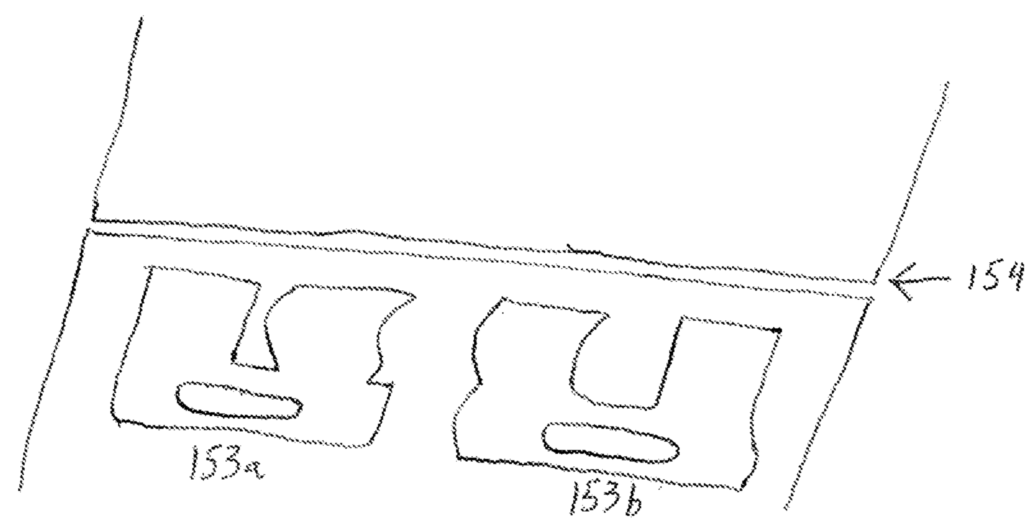
FIG. 15B is another end view depicting a feature of a draping device.

FIGS. 15B and 15C depict a drape with asymmetric handles 153*a,b* for separating the drape at a drape separation point 154. In the embodiment depicted in FIGS. 15B and 15C, the drape has an outside attachment that is shorter than an inside attachment, resulting in a pulling force 155 applied by a user to be transmitted non-uniformly along a perforation of the drape. In particular, when the user applies the pulling force 155, the outer edges of the drape separate first, creating a necking 156. As the user continues to apply the pulling force 155, the inner portion of the drape further separates until the drape is fully separated.

The embodiments shown in FIGS. 15A-15C may be particularly employed to maintain the sterility of a surgical "back table" and the instruments and equipment lying thereon. The drape may include a separable portion located in a medial section of the "double Z" configuration, or alternatively the separable portion may be located at the seam or transition point or either of the "double Z" folds of the drape shown in FIGS. 15A-C.

Figure 16:
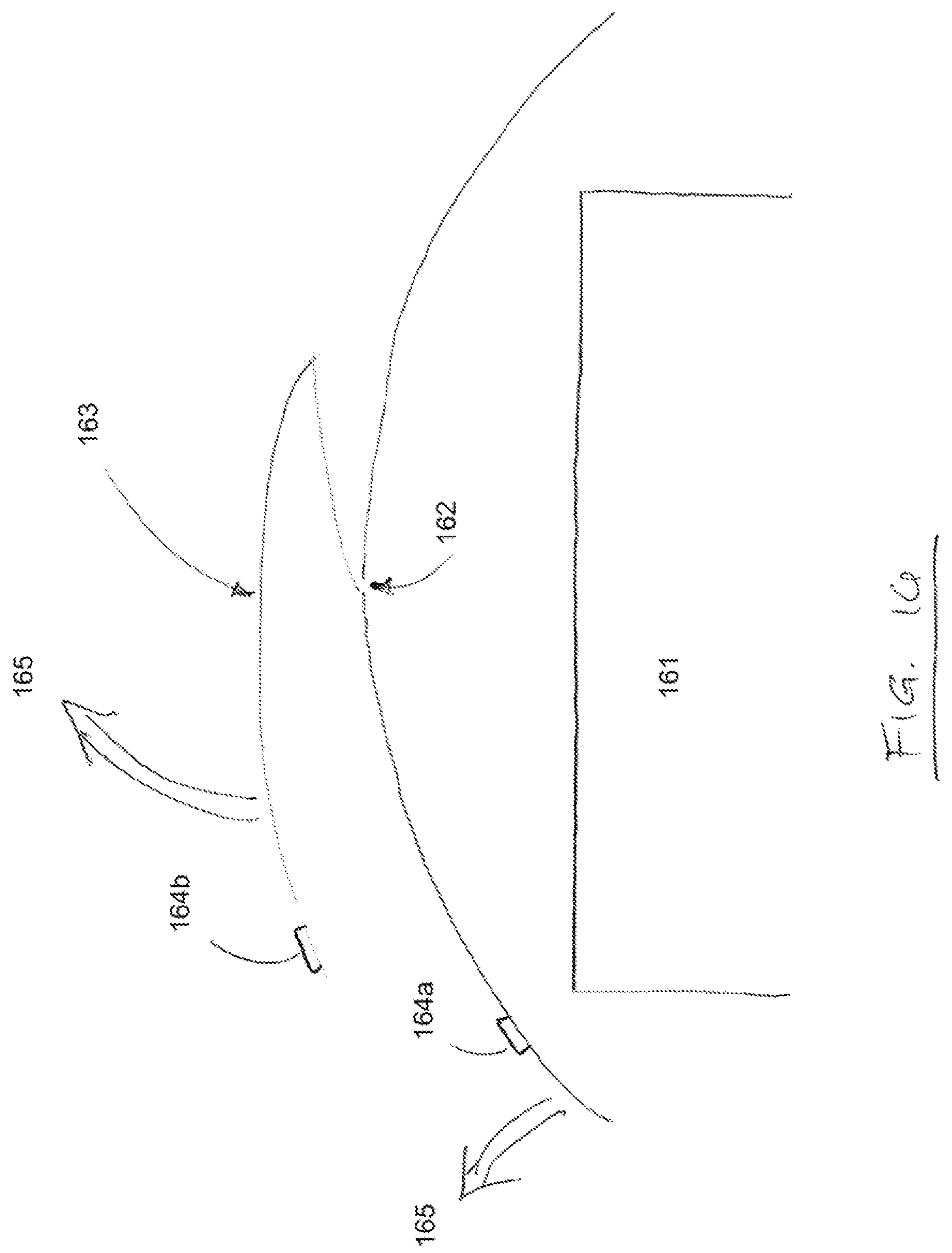
FIG. 16 is an end view depicting one possible use of a draping device according to one embodiment of the present disclosure.

FIG. 16 depicts an end view of another drape, which preferably may be used to maintain the sterility of a surgical back table 161. In this embodiment, the drape comprises a perforated portion 162, which is preferably provided with a superior cover or "dust cover" 163 to an inferior cover. The superior cover 163 and inferior cover preferably comprise handles 164*a,b* accessible on the same side of the table 161. When the drape is to be removed, a user applies a pulling force 165 to the handles 164*a,b* to pull the handles toward opposite sides of the table 161 or other sterile underlying surface. The drape separates along the perforated portion 162 and may be pulled, or allowed to fall, over opposing sides of the table 161 without compromising the sterility of the back table 161 or the instruments and equipment thereon. Although handles are described, other mechanisms may be provided for ease of separation and to prevent forces being imparted on the drape in a direction other than the direction required to cause separation of the drape shown in FIG. 16. It is to be expressly understood that the dust cover 163 may be of any suitable length, and that any number and arrangement of dust cover handles 164*b* may be provided. By way of non-limiting example, a second set of one or more dust cover handles 164*b* may be disposed on an underside or inferior surface of the dust cover 163 and thus exposed only when the dust cover 163 is folded back in preparation for separation of the drape; such a second set of handles may aid operating room personnel in applying the pulling force needed to separate the drape.

In one embodiment, the "dust cover" further comprises one or more handles for ease of use in separating the "dust cover." In one embodiment, the "dust cover" may be selectively removable without separating the underlying drape. In yet another embodiment, the act of separating dust cover from drape in turn causes the drape to be separated along a predetermined separable portion.

In one embodiment, the handles may be positioned and oriented such that separation first occurs about an outer edge of the drape, as depicted in FIG. 16. In one particular embodiment, the handles may not be symmetrical, and in a preferred embodiment as asymmetrical. These embodiments permit both temporary separation of an outer portion of drape, and also ensure that the separable portions of drape are continually removed away from the underlying sterile field while the remainder of the predetermined separable portion of drape is in the process of separation. As the user continues to pull on the asymmetric handles, the drape will continue to separate from the outer edge to an inner portion of the predetermined separable portion of drape.

It is generally desirable for back table drapes, as illustrated in FIGS. 15A through 16 and described elsewhere throughout this disclosure, to be sized such that there is an appropriate degree of "overhang" between the edge of the surgical back table and the edge of the drape, which in embodiments allows surgical instruments to be piled, stacked, or otherwise placed on the underlying table while maintaining an appropriate overhang. Particularly, an overhang of between about 16 inches and about 22 inches is usually desired to ensure complete coverage of the surgical back table and allow a certain amount of "slack" in the drape so that it can be easily secured, e.g. to legs of the surgical back table. By way of first non-limiting example, for a small rectangular back table measuring 20 inches by 36 inches, an appropriately sized drape may measure 52-64 inches by 68-80 inches to allow an overhang of 16 to 22 inches about each of the four sides of the back table. By way of second non-limiting example, for a medium rectangular back table measuring 24 inches by 60 inches, an appropriately sized drape may measure 56-68 inches by 92-104 inches to allow an overhang of 16 to 22 inches about each of the four sides of the back table. By way of third non-limiting example, for a large rectangular back table measuring 30 inches by 72 inches, an appropriately sized drape may measure 62-74 inches by 104-116 inches to allow an overhang of 16 to 22 inches about each of the four sides of the back table. In embodiments, surgical back table drapes may be provided with a visual indicator, e.g. a color of a drape material, that allows operating room personnel to quickly and easily select and/or identify the correct size of drape for a given application.

In embodiments, one or more additional features may be provided in or with the back table drapes illustrated in FIGS. 15A through 16. As a first non-limiting example, back table drapes of the present invention may be provided with handles, similar to the handles provided on, e.g., Mayo stand and patient drapes of the present invention, to assist in separating and removing the back table drape. As a second non-limiting example, instead of or in addition to handles, back table drapes of the present invention may be provided with grip region indicators, e.g. a portion of the drape made of a different material or having a different color, that allow operating room personnel to readily identify gripping points of the back table drape. As a third non-limiting example, instead of or in addition to either or both of the above features, back table drapes of the present invention may be provided with finger loops to allow operating room personnel to move or reposition the drape using one, two, or more than two fingers, and/or to lift the drape slightly prior to separation, e.g. to maintain continuity of a reference frame of imaging equipment or prevent inadvertent movement of underlying surgical instruments; such finger loops may, in embodiments, be located in several different places on a given drape to allow the drape to be used to cover back tables of multiple different sizes.

It is to be expressly understood that the sterility maintenance elements of back table drapes of the present invention, e.g. Z folds and the like, need not always be provided across an entire length (or width) of the back table drape. In embodiments, it may be desirable for the Z fold or any other sterility maintenance element or other configuration of overlapping drape edges to be included only on those portions of the drape which cover certain defined portions of the back table; the Z fold may thus terminate short of the edge of the drape, with the perforation continuing to the edge of the drape to allow the drape to be separated.

Figure 17:
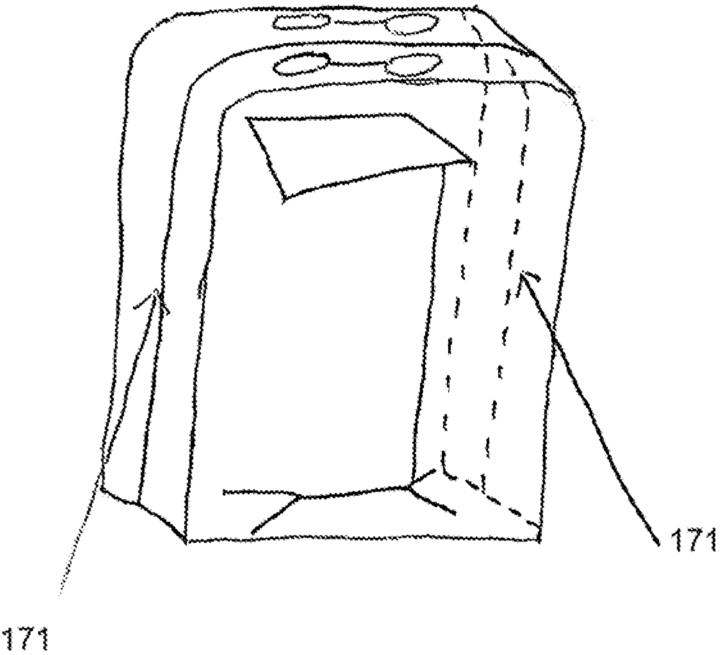
FIG. 17 is a side elevation view depicting a feature of a draping device according to one embodiment of the present disclosure.

FIG. 17 depicts an embodiment of a drape which may be used to cover a movable or repositionable instrument stand, commonly referred to as a "mayo stand," and maintain the sterility of the mayo stand. In this embodiment, the drape comprises a perforated flap 171 along the vertical faces. As shown, the drape of this embodiment further comprises handles in the top face. When the drape is to be removed, the handles are pulled in opposite directions. The drape separates along the perforated flap 171 and may be pulled, or allowed to fall, over the mayo stand without compromising the sterility of the stand or the instruments and equipment thereon. Although handles are described, other mechanisms may be provided for ease of separation and to prevent forces being imparted on the drape in a direction other than the direction required to cause separation of the drape shown in FIG. 17.

Figure 18A:
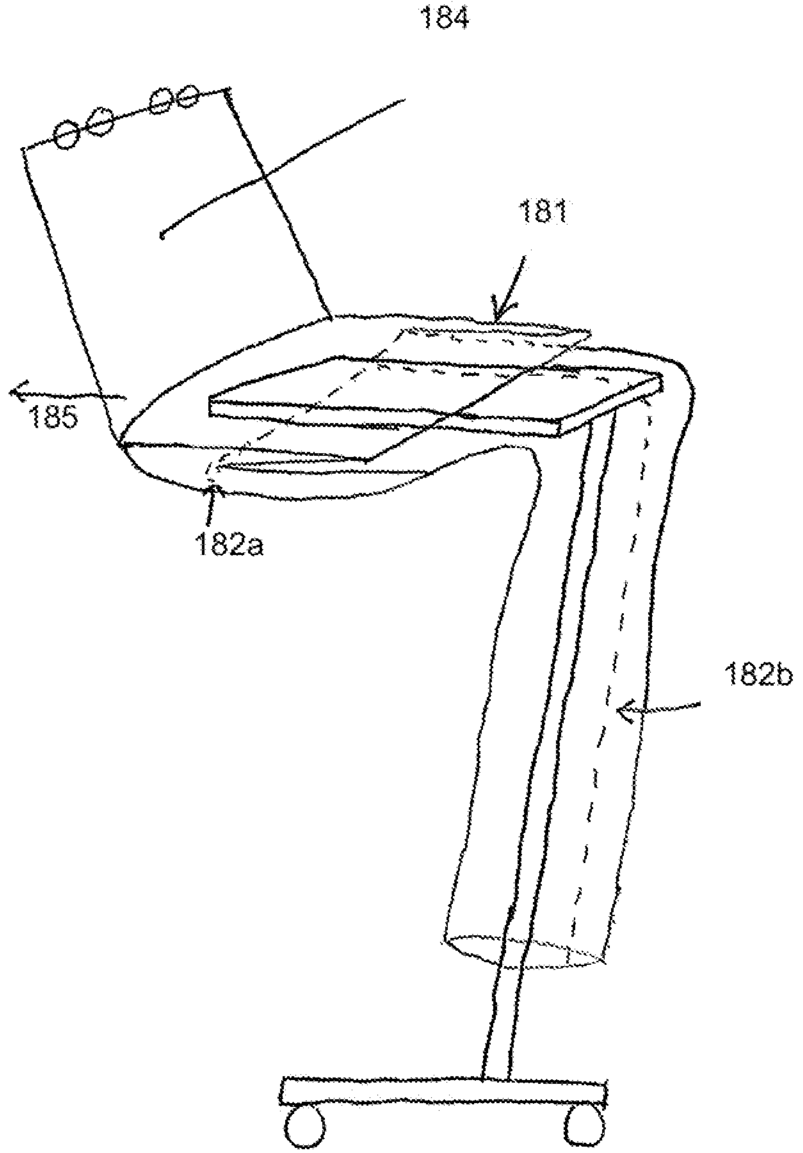
FIG. 18A is a side elevation view depicting one possible use of a draping device according to one embodiment of the present disclosure.
Figure 18B:
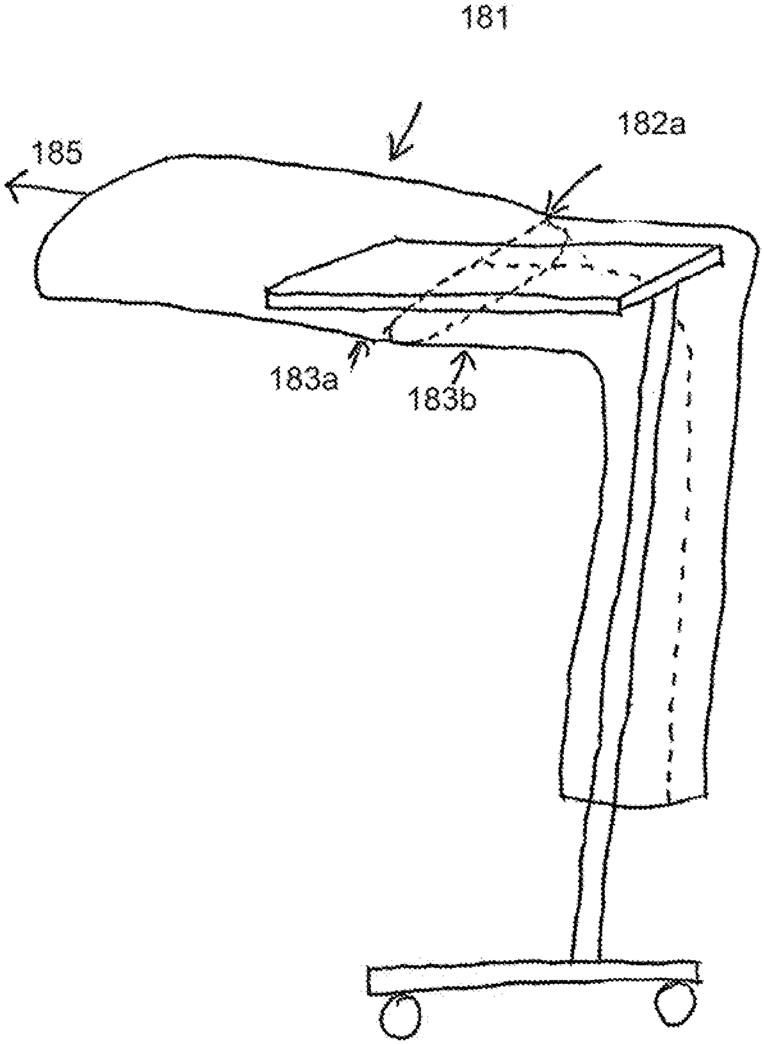
FIG. 18B is another side elevation view depicting one possible use of a draping device according to one embodiment of the present disclosure.
Figure 18C:
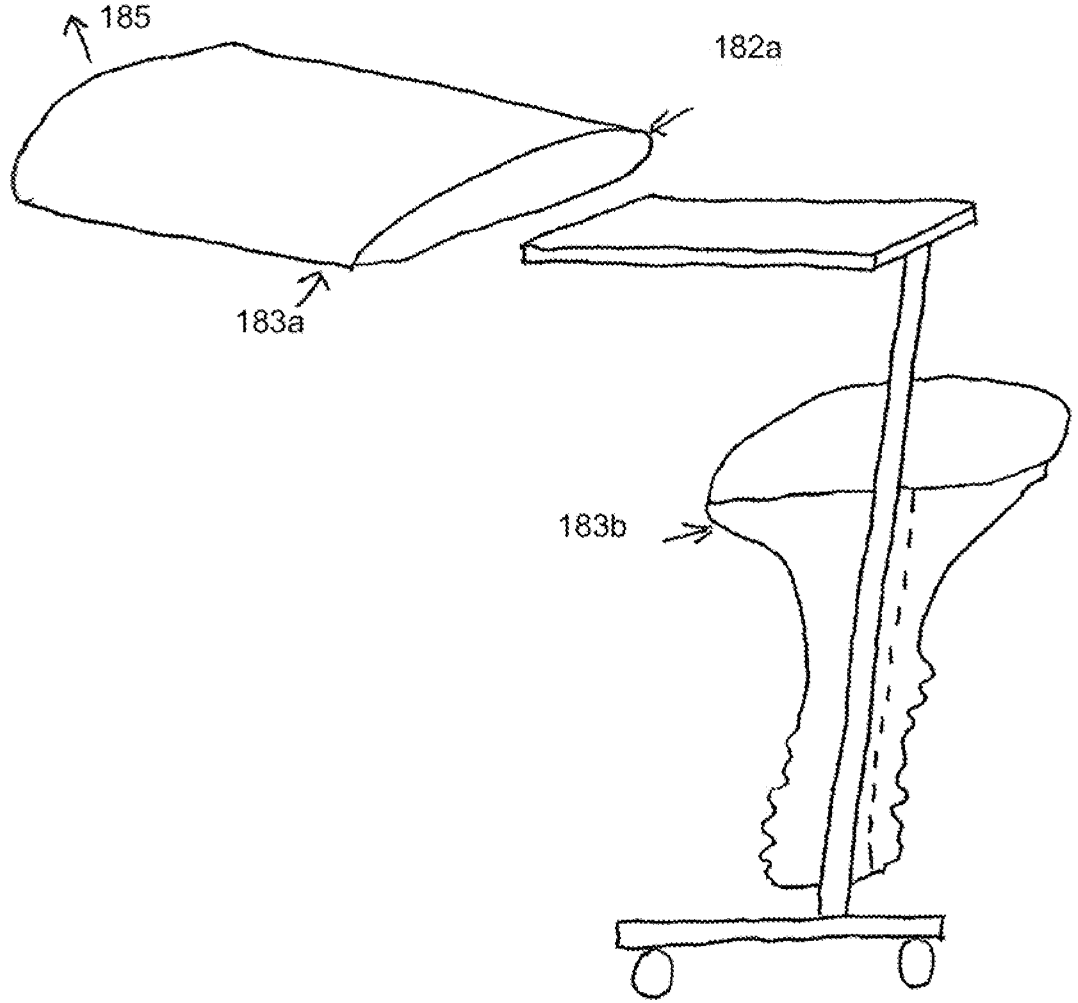
FIG. 18C is another side elevation view depicting one possible use of a draping device according to one embodiment of the present disclosure.
Figure 18D:
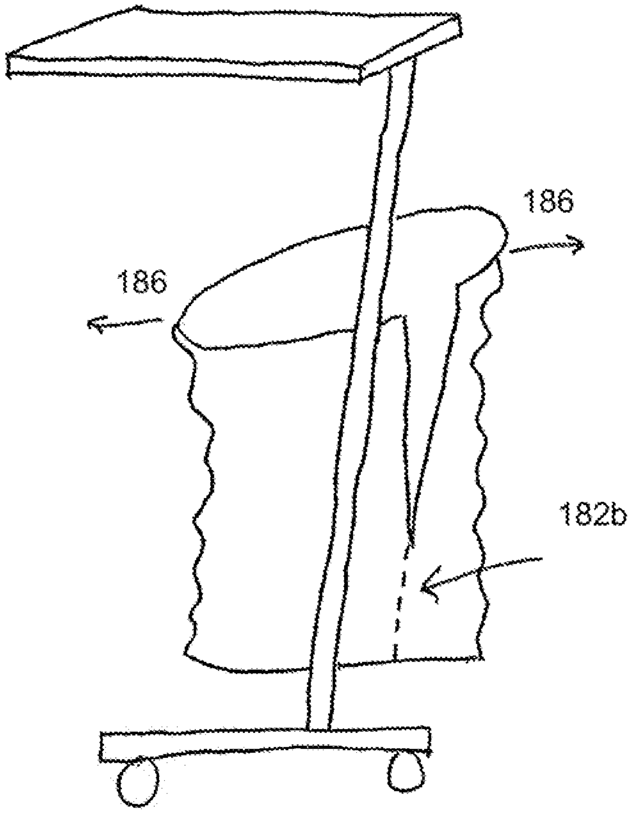
FIG. 18D is another side elevation view depicting one possible use of a draping device according to one embodiment of the present disclosure.

FIGS. 18A-D depict side elevation views of another drape for maintaining the sterility of a mayo stand. A portion of the drape comprises a flap 181, which comprises a breakaway perforation 182*a* which overlies the top surface of the mayo stand and joins edges of two separable portions of the drape 183*a,b*. The flap surrounds a table portion of the mayo stand, maintaining the sterility of that portion and the tools and instruments thereon. The drape further comprises other breakaway perforations 182*b* and a dust cover 184, which, in FIG. 18A, has been pulled up by a user applying a pulling force 185. In FIG. 18B, the flap 181 is pulled straight by the pulling force 185, placing tension on the breakaway perforation 182*a* of the flap, and, as shown in FIG. 18C, the drape portions separate along the perforation between the separable portions 183*a,b*. The lower portion of the drape "falls away" without compromising the sterility of the table portion of the mayo stand. The flap 181 maintains a sterile surface adjacent the perforation 182*a*. As shown in FIG. 18D, the other breakaway perforations 182*b* on the lower portion of the drape may allow a user to "unzip" the lower portion of the drape by applying a pulling force 186, facilitating easier removal and disposal of the drape. Although a perforated separable drape is described in these embodiments, it is expressly understood that other means of providing a predetermined separable portion of the drape are included and considered within the scope of the invention. For example, a surface with scoring along the predetermined separable portion may be provided. As another example the drape may be comprised of a different material along the predetermined separable portion, wherein the different material comprises a characteristic which allows it to be torn or separated more easily than the material of the remainder of the drape.

Figure 19:
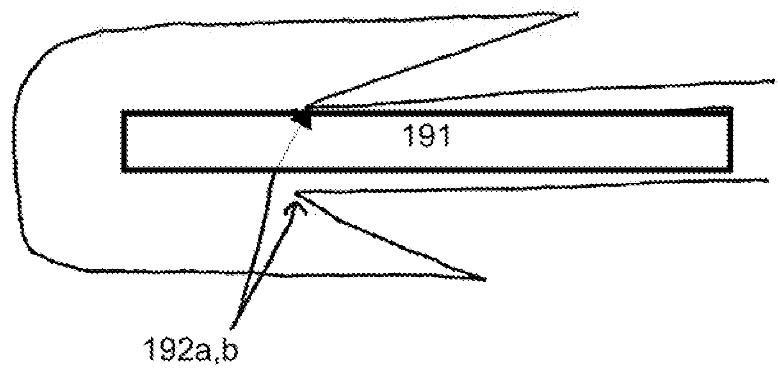
FIG. 19 is a side elevation view depicting a feature of a draping device according to one embodiment of the present disclosure.

FIG. 19 depicts a side elevation view of a drape for maintaining the sterility of a mayo stand. In this embodiment, the drape comprises a Z flap, which surrounds a table portion 191 of the mayo stand circumferentially. Perforations 192*a,b* on inner portions of the Z flap allow the drape to be separated when the Z flap is pulled straight, as depicted in FIG. 18B.

Figure 20A:
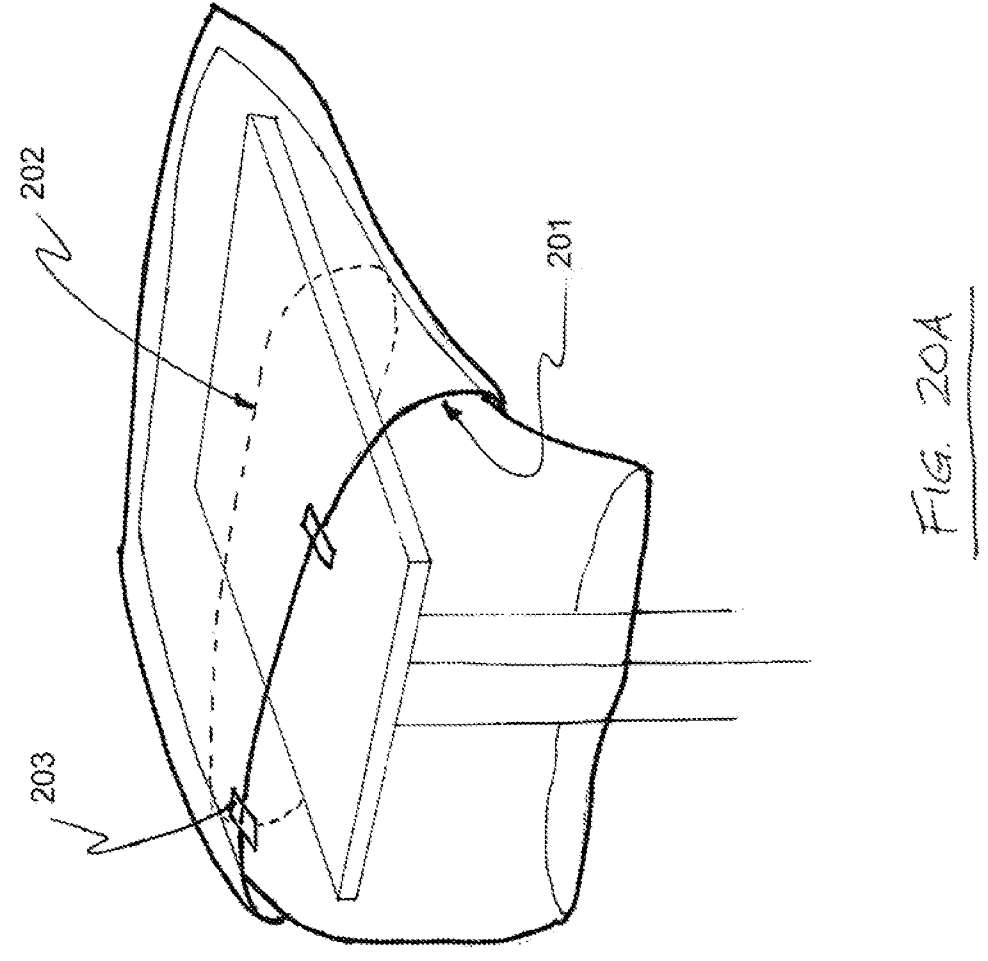
FIG. 20A is a top perspective view depicting one possible use of a draping device according to one embodiment of the present disclosure.
Figure 20B:
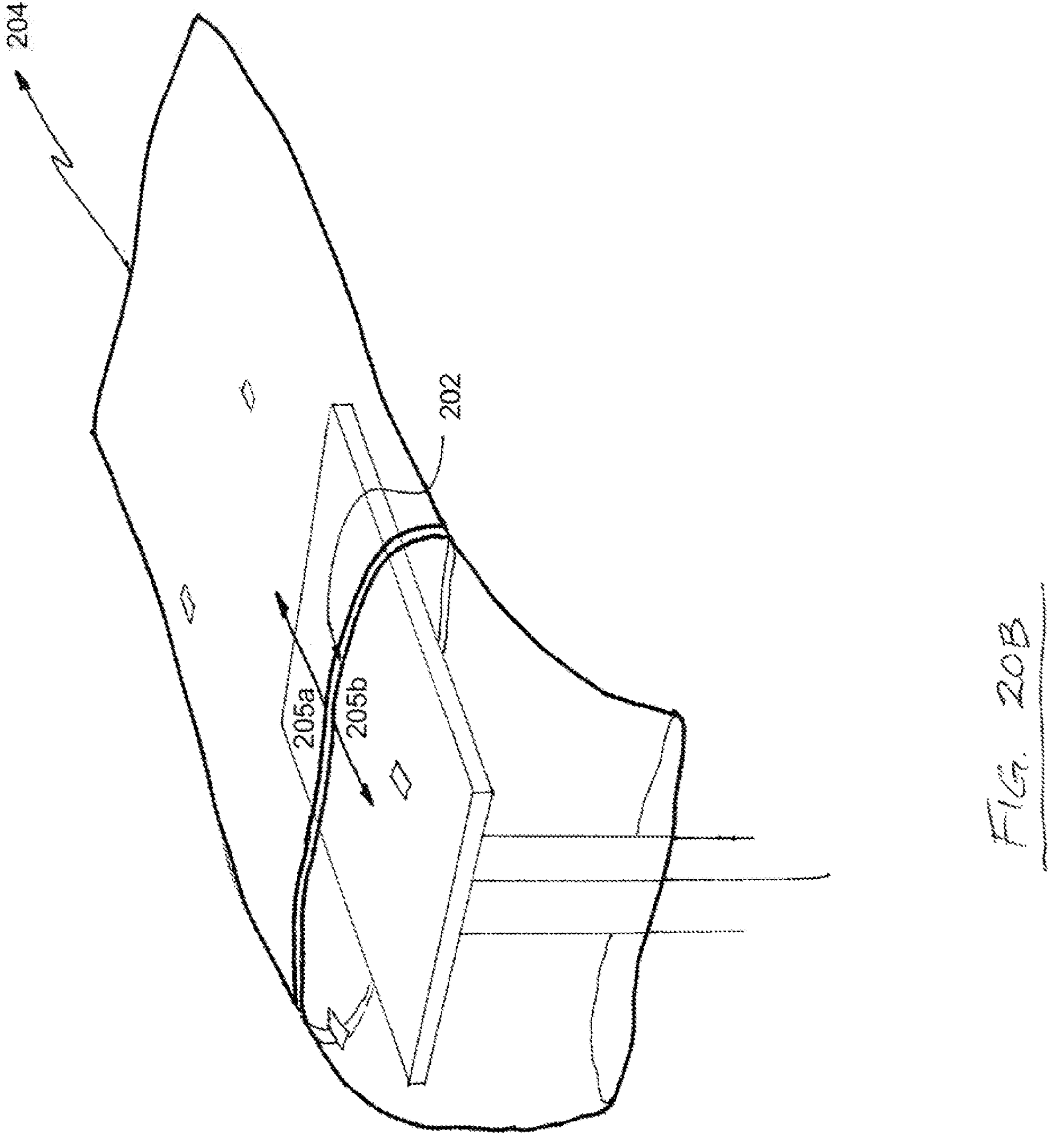
FIG. 20B is another top perspective view depicting one possible use of a draping device according to one embodiment of the present disclosure.

FIGS. 20A and 20B depict top perspective views of another drape for maintaining the sterility of a mayo stand. As shown in FIG. 20A, the drape comprises a telescope fold 201, which covers a perforation 202 overlying a table portion of a mayo stand. The telescope fold is held in place by at least one "tear here" label 203. As shown in FIG. 20B, the distal end of the drape is pulled outward by a user applying a pulling force 204, breaking the "tear here" labels

203 and unfolding the telescope fold 201. Separable portions 205*a,b* of the drape then separate along the perforation 202.

Figure 21A:
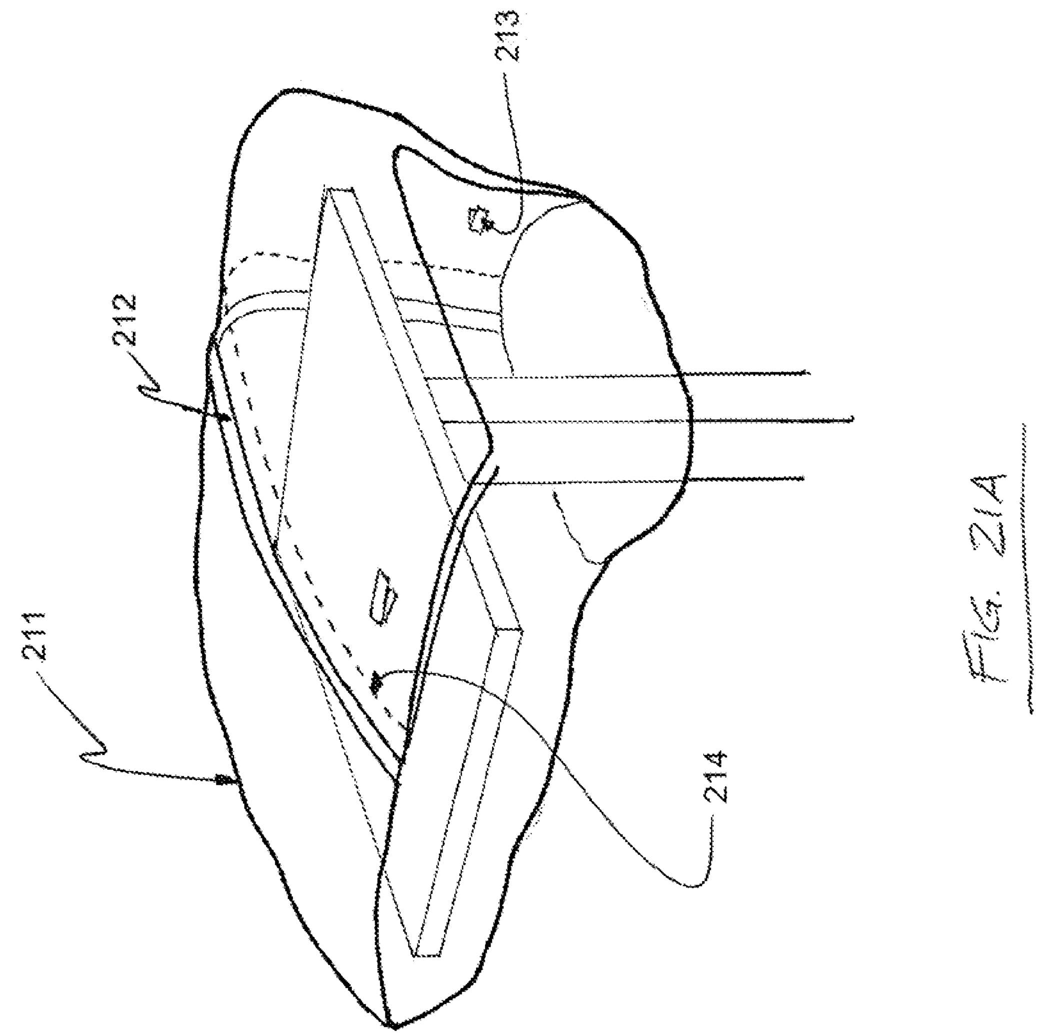
FIG. 21A is a top perspective view depicting one possible use of a draping device according to one embodiment of the present disclosure.
Figure 21B:
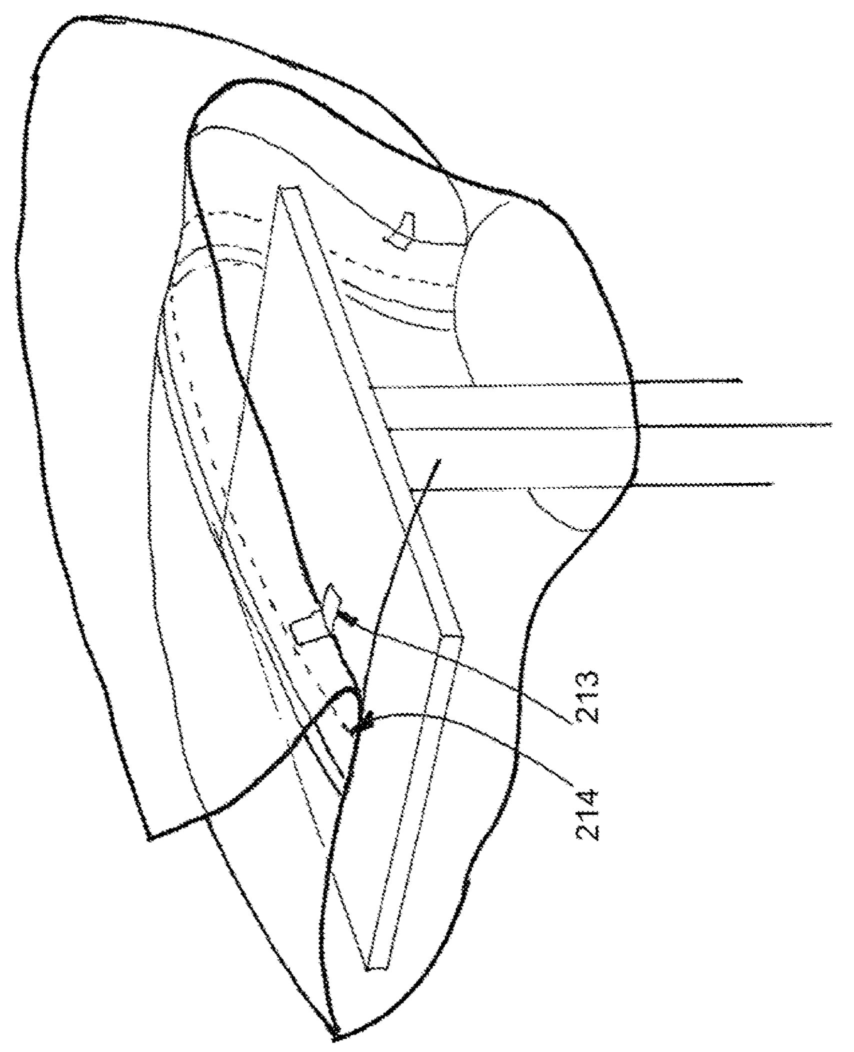
FIG. 21B is another top perspective view depicting one possible use of a draping device according to one embodiment of the present disclosure.
Figure 21C:
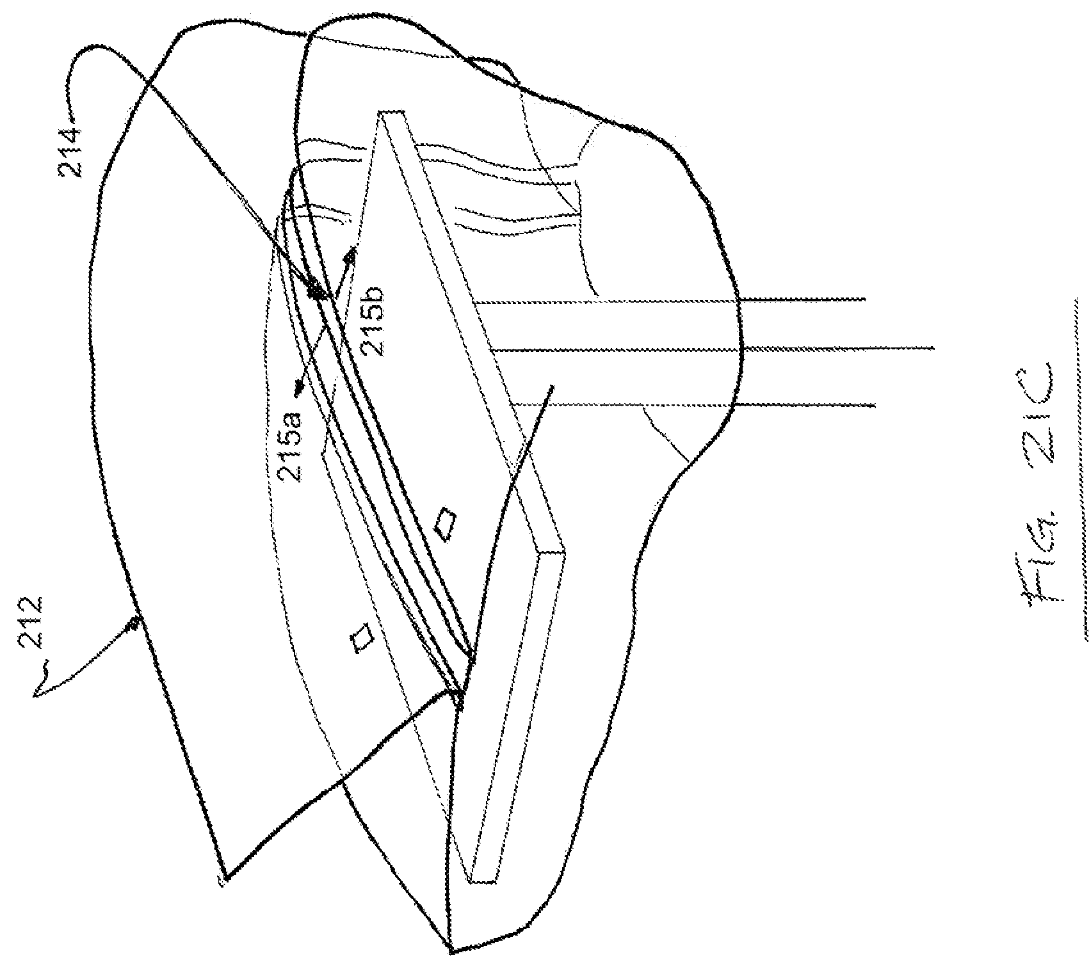
FIG. 21C is another top perspective view depicting one possible use of a draping device according to one embodiment of the present disclosure.

FIGS. 21A-C depict top perspective views of another drape 211 for maintaining the sterility of a mayo stand. As shown in FIG. 21A, the drape 211 is placed over the top surface of a mayo stand and comprises a sealed flap 212, which is held in place by at least one "tear here" label 213. The drape 211 further comprises a perforation 214, which is covered by the flap 212. As shown in FIG. 21B, the "tear here" labels 213 hold the flap 212 in place when the flap 212 is put in light tension, preventing the perforation 214 from being exposed and opening accidentally or prematurely. As shown in FIG. 21C, a greater degree of tension on the flap 212 breaks the "tear here" labels 213 and separates separable portions 215*a,b* along the perforation 214.

Figure 22A:
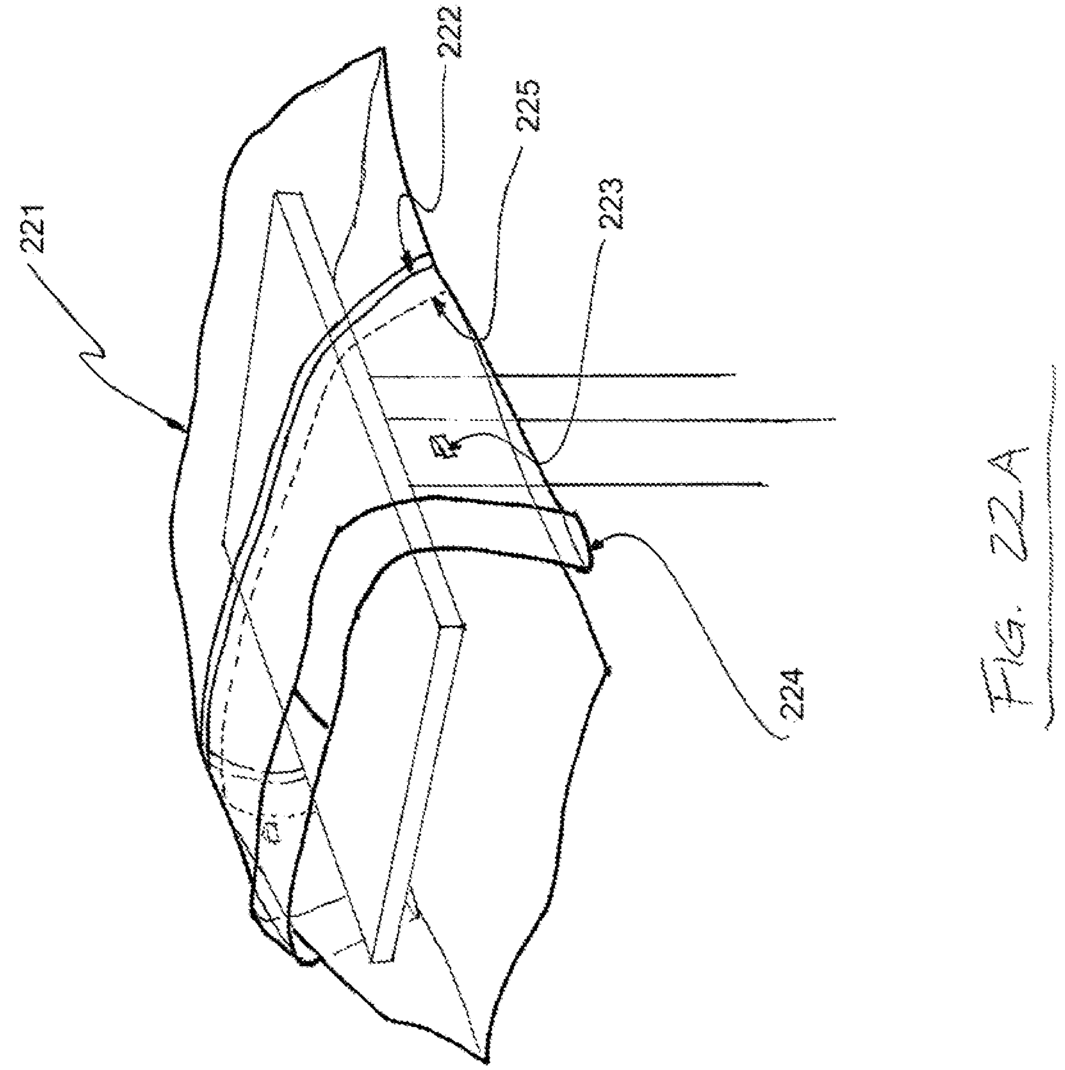
FIG. 22A is a top perspective view depicting one possible use of a draping device according to one embodiment of the present disclosure.
Figure 22B:
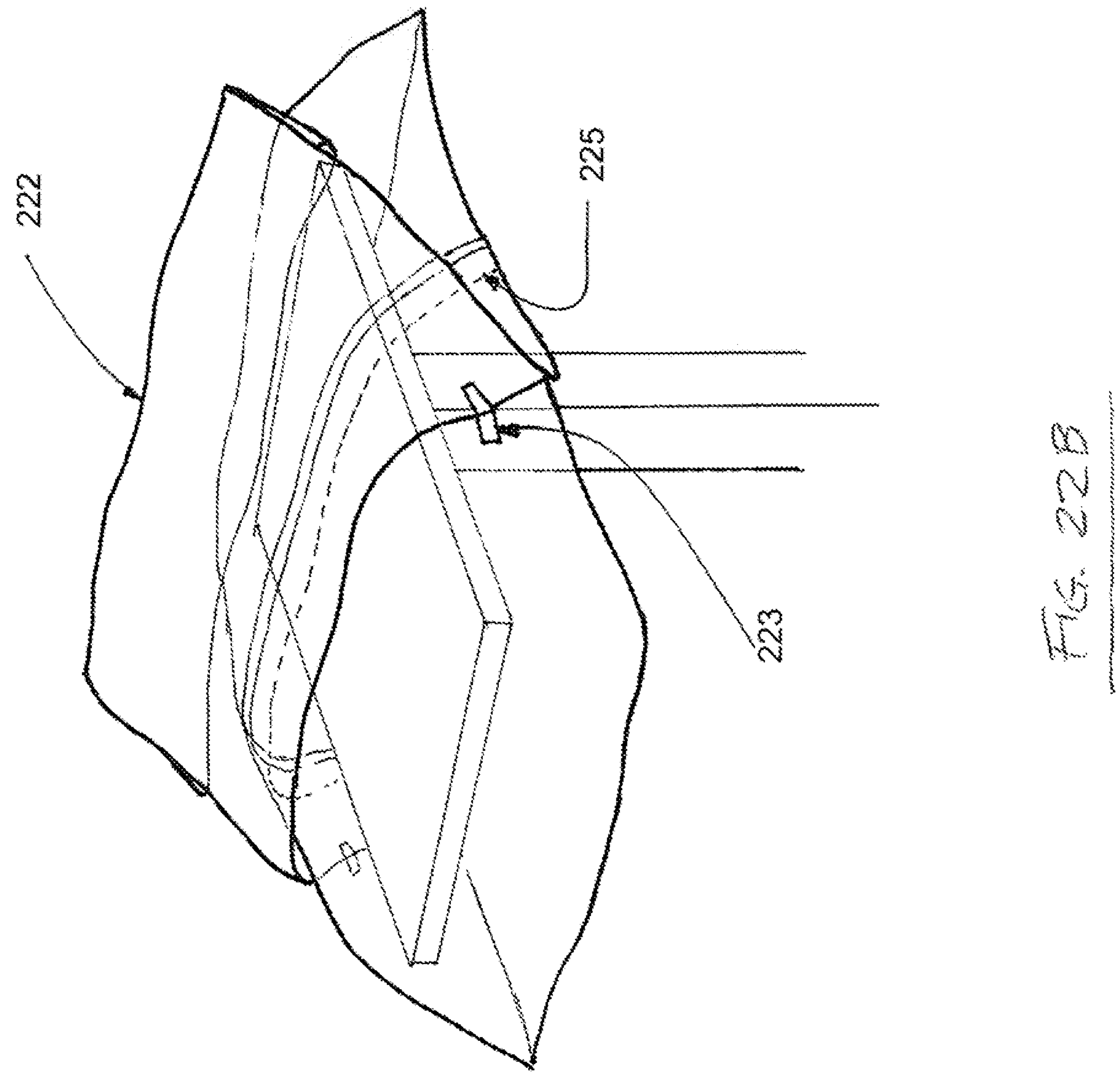
FIG. 22B is another top perspective view depicting one possible use of a draping device according to one embodiment of the present disclosure.
Figure 22C:
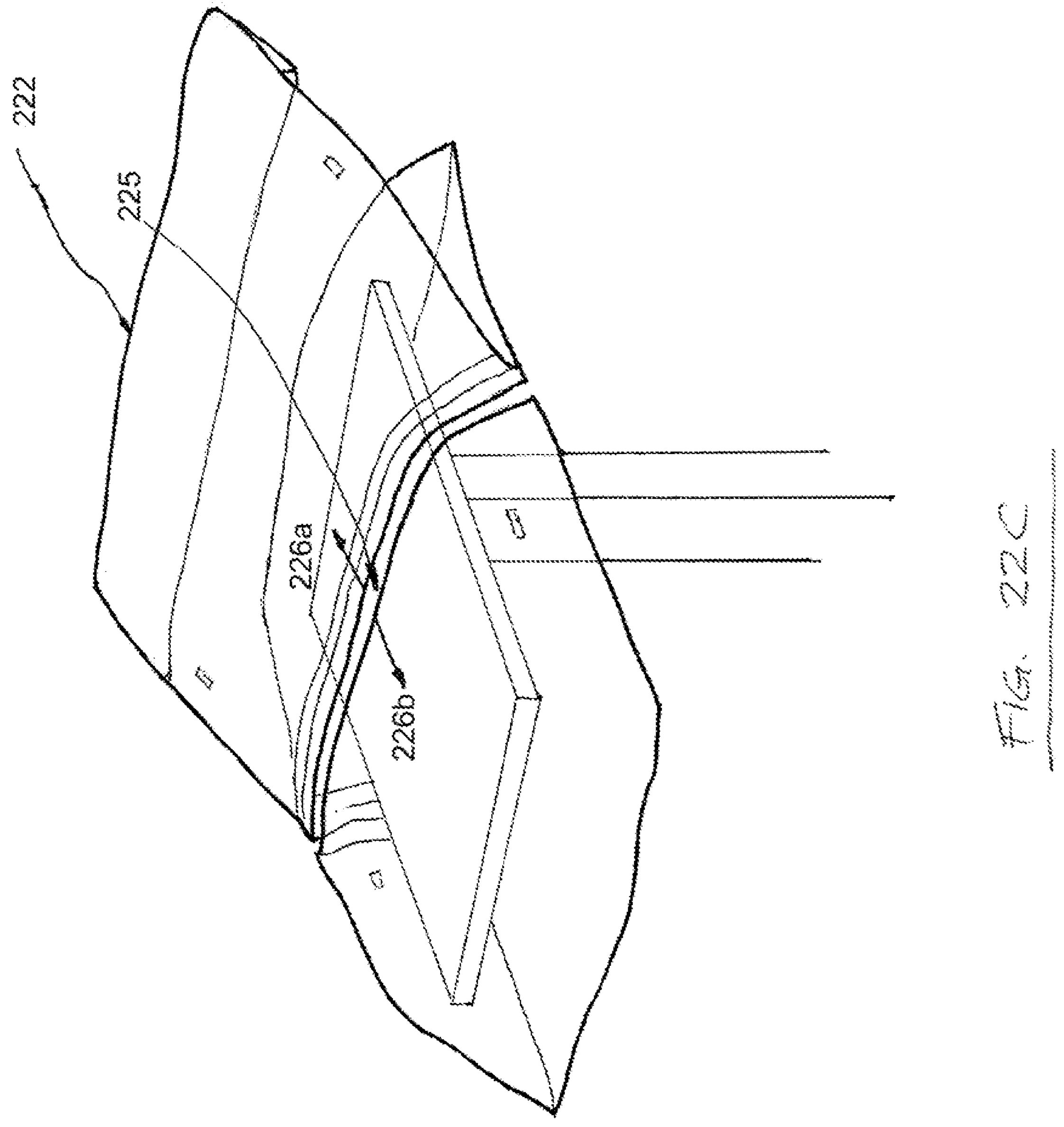
FIG. 22C is another top perspective view depicting one possible use of a draping device according to one embodiment of the present disclosure.

FIGS. 22A-C depict top perspective views of another drape 221 for maintaining the sterility of a mayo stand. As shown in FIG. 22A, the drape 221 is placed over the top surface of a mayo stand and comprises a sealed flap 222, which is held in place by at least one "tear here" label 223 and comprises a cuff end fold 224. The drape 221 further comprises a perforation 225, which is covered by the flap 222. As shown in FIG. 21B, the "tear here" labels 223 hold the flap 222 in place when the flap 222 is put in light tension, preventing the perforation 225 from being exposed and opening accidentally or prematurely. As shown in FIG. 22C, a greater degree of tension on the flap 222 breaks the "tear here" labels 223 and separates separable portions 226*a,b* along the perforation 225.

Figure 23A:
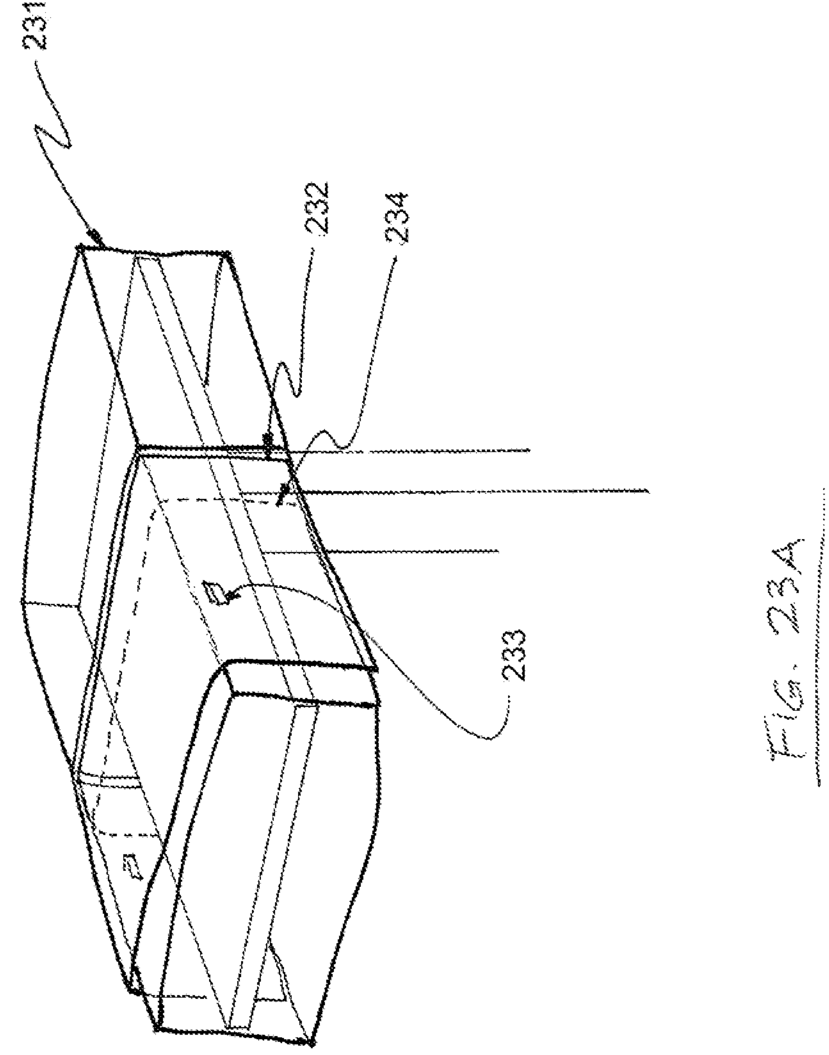
FIG. 23A is a top perspective view depicting one possible use of a draping device according to one embodiment of the present disclosure.
Figure 23B:
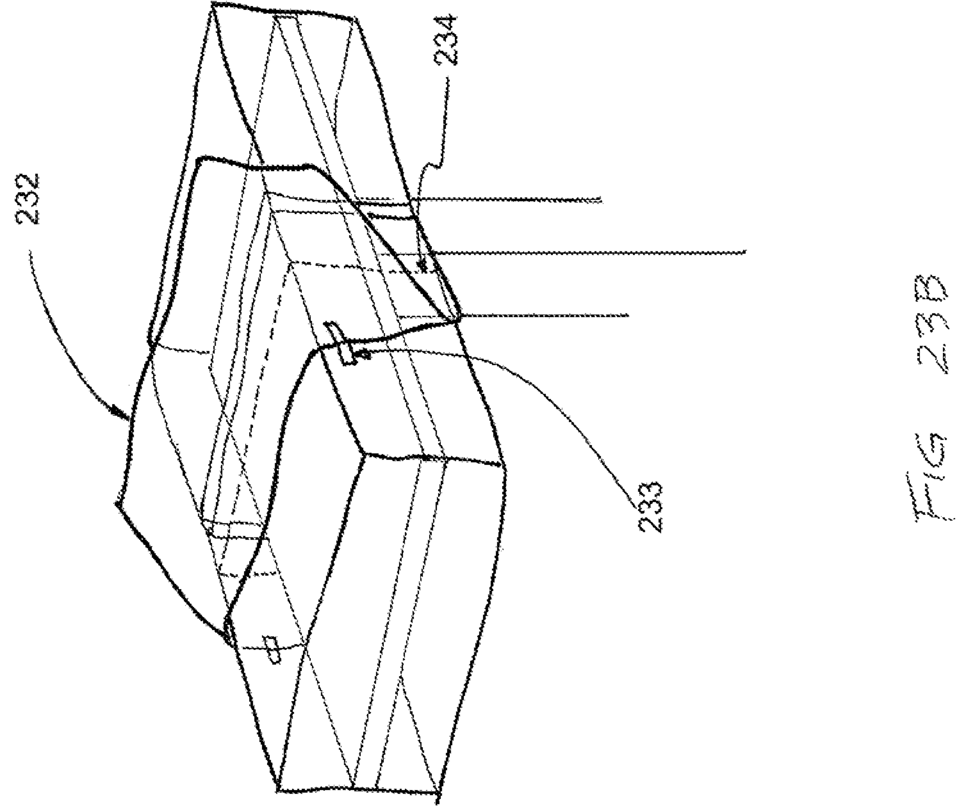
FIG. 23B is another top perspective view depicting one possible use of a draping device according to one embodiment of the present disclosure.
Figure 23C:
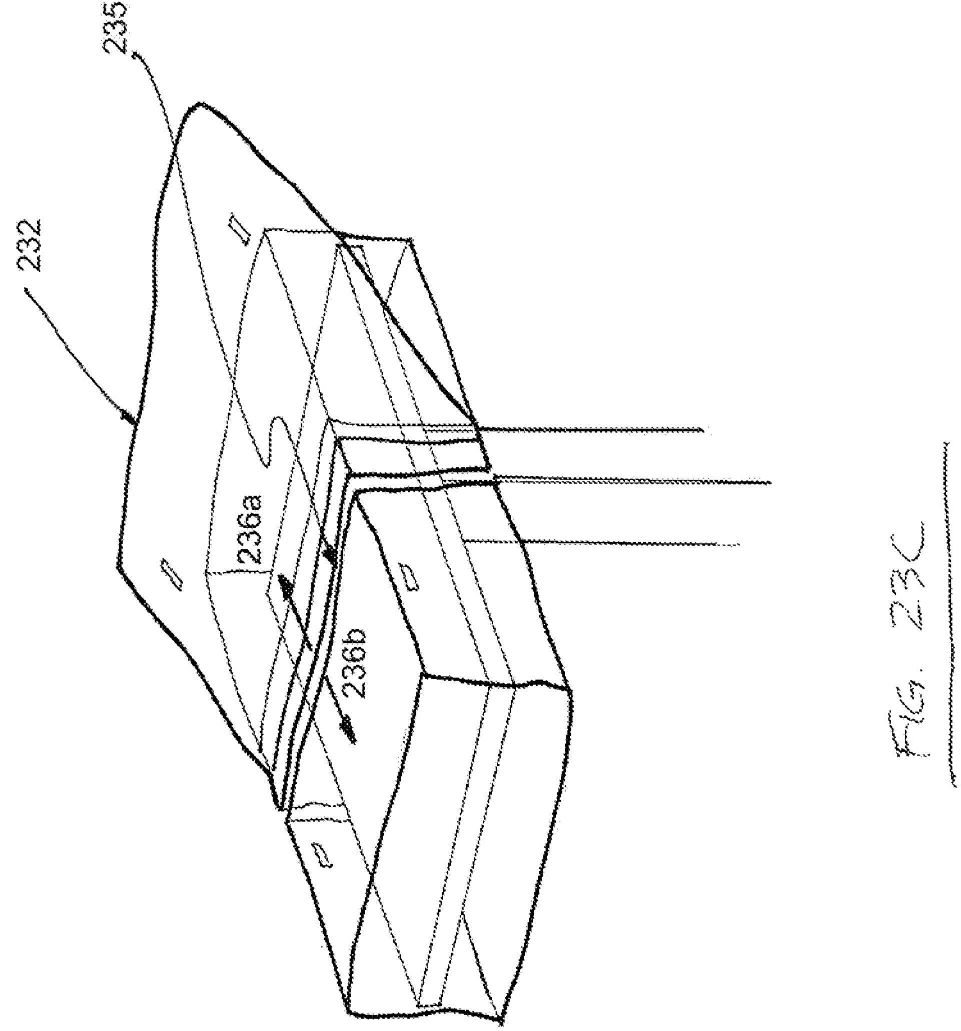
FIG. 23C is another top perspective view depicting one possible use of a draping device according to one embodiment of the present disclosure.

FIGS. 23A-C depict top perspective views of another drape 231 for maintaining the sterility of a mayo stand. As shown in FIG. 23A, the drape 231 comprises rigid or "boxed" sides and a sealed flap 232, which is held in place by at least one "tear here" label 233. The drape 231 further comprises a perforation 234, which is covered by the flap 232. As shown in FIG. 23B, the "tear here" labels 233 hold the flap 232 in place when the flap 232 is put in light tension, preventing the perforation 234 from being exposed and opening accidentally or prematurely. As shown in FIG. 23C, a greater degree of tension on the flap 232 breaks the "tear here" labels 233 and separates separable portions 235*a,b* along the perforation 234.

Referring now to FIGS. 24 through 37, embodiments of single-use disposable outer surgical drapes comprising a circumferential Z-fold are illustrated. Outer surgical drapes according to these embodiments may have several advantages and benefits relative to the covering and draping solutions of the prior art. Particularly, outer surgical drapes comprising a circumferential Z-fold can maintain the sterility of an underlying item of surgical equipment until such time as the item of surgical equipment is needed for use, or, in other words, contamination of the item of surgical equipment can be eliminated at all times up to and including the moment the item of surgical equipment must be used in a sterile field. Additionally, outer surgical drapes according to the present invention allow an item of surgical equipment to be carefully and meticulously draped with an inner drape (often a custom-fit inner drape) prior to, rather than during, a surgical procedure, and then covered with the outer drape; given the ease and speed (generally three to five seconds) with which the outer drape can be removed, this saves operating room personnel considerable time and effort during the surgical procedure, resulting in reduced cost and risk to the patient of the surgical procedure.

Embodiments of single-use disposable outer surgical drapes of the present invention are characterized in that they comprise a perforation or separation portion whereby separating edges have been protected and/or maintained as sterile by an overlying circumferential Z-fold pleat or other mechanism as described herein, including, by way of non-limiting example, a "double overbite," a double perforation, a peel-away adhesive portion, multiple opposing pleats, a superior cover or dust cover, and so on. Outer surgical drapes of the present invention are also characterized in that they constitute protective coverings having at least one open mouth or end on one side of the protective covering. The outer surgical drape may take any suitable shape, including but not limited to a tube-like shape (i.e. having two open mouths or ends) and/or a bag-like shape (i.e. having one open mouth or end), and may define an interior volume having a cross-section of any suitable shape, including but not limited to a rectangular cross-section (similar to, e.g., a sandwich bag) and/or a circular or elliptical cross-section (similar to, e.g., a condom or garbage bag). A particular advantage of the outer surgical drapes of the present invention is that none of the one or more open ends or mouths of the drape comes into contact with the item of surgical equipment covered by the drape; any one or more of a variety of sterile separation mechanisms as disclosed herein (a "double overbite," a sterile Z-fold, a secondary "dust cover," etc.) are provided on or in the outer drape at a point distant from the open mouth or end, allowing for separation of two or more portions of the drape without contaminating an underlying surface or item.

Figure 24:
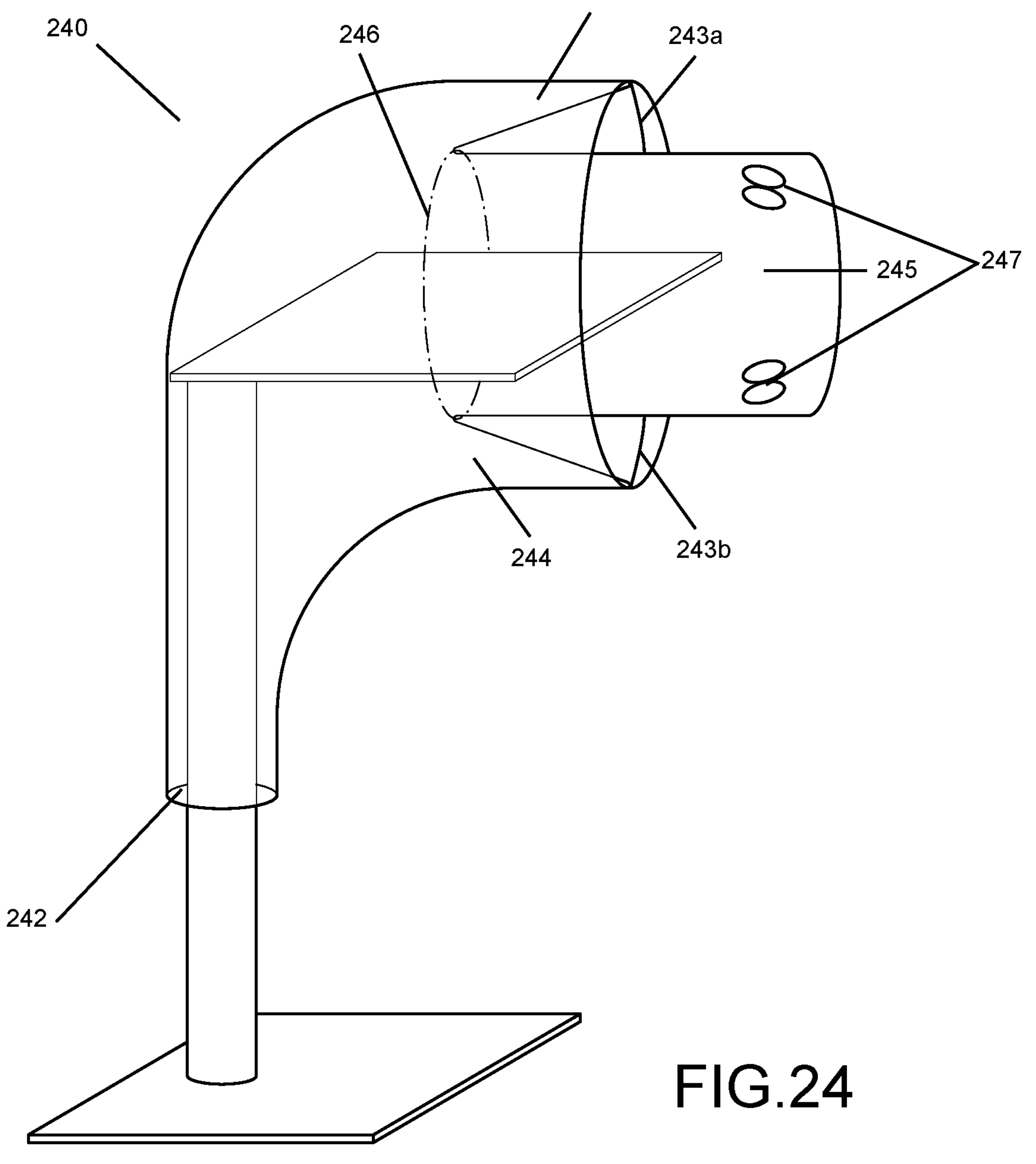
FIG. 24 is an illustration of a single-use disposable outer surgical drape having a circumferential Z-fold pleat, according to embodiments of the present disclosure.

Referring now to FIG. 24, a single-use disposable outer surgical drape 240 having a circumferential Z-fold pleat 241 is illustrated. In the illustrated embodiment, the outer drape 240 is covering and maintaining the sterility of a Mayo stand having surgical instruments thereon, and has a bag-type shape, i.e. has a single open end or mouth 242. To allow the surgical instruments on the Mayo stand to be used without compromising the sterility of the stand or instruments, the outer drape 240 must be removed in such a way that the open end or mouth 242, which has been disposed below the surface of the table in a non-sterile region and thus may not be considered sterile, is not brought over or across the sterile surface of the stand or the sterile instruments thereon. To accomplish this, break tabs 243*a,b* or a similar feature (e.g. a perforation) are provided, in conjunction with the circumferential Z-fold pleat 241, that secure an outer portion 244 of the drape to an inner portion of the drape 245 and may be broken or separated by operating room personnel, allowing the inner portion 245 to be pulled away from (in this illustration, to the right) the outer portion 244; the inner portion 245 then separates from the outer portion 244 along a circumferential perforation 246. Inner portion handles 247 may, but need not, be provided to assist operating room personnel in pulling the inner portion 245 away from the outer portion 244. With the inner portion 245 removed (as illustrated, to the right), the outer portion 244, under its own weight, falls away from the surface of the stand, i.e. the Z-fold pleat 241 falls in the direction of the non-sterile open end or mouth 242. In this way, the non-sterile open end or mouth 242 is never brought into close proximity with the sterile surface of the stand or the sterile instruments thereon, thereby preserving the sterility of the surface and instruments. It is to be expressly understood that the outer drape 240 illustrated in FIG. 24 may, but need not always, cover an inner drape, and that the outer drape 240 and inner drape (if any) may cover and maintain the sterility of surgical apparatuses, devices, and/or machines other than Mayo stands.

Figure 25:
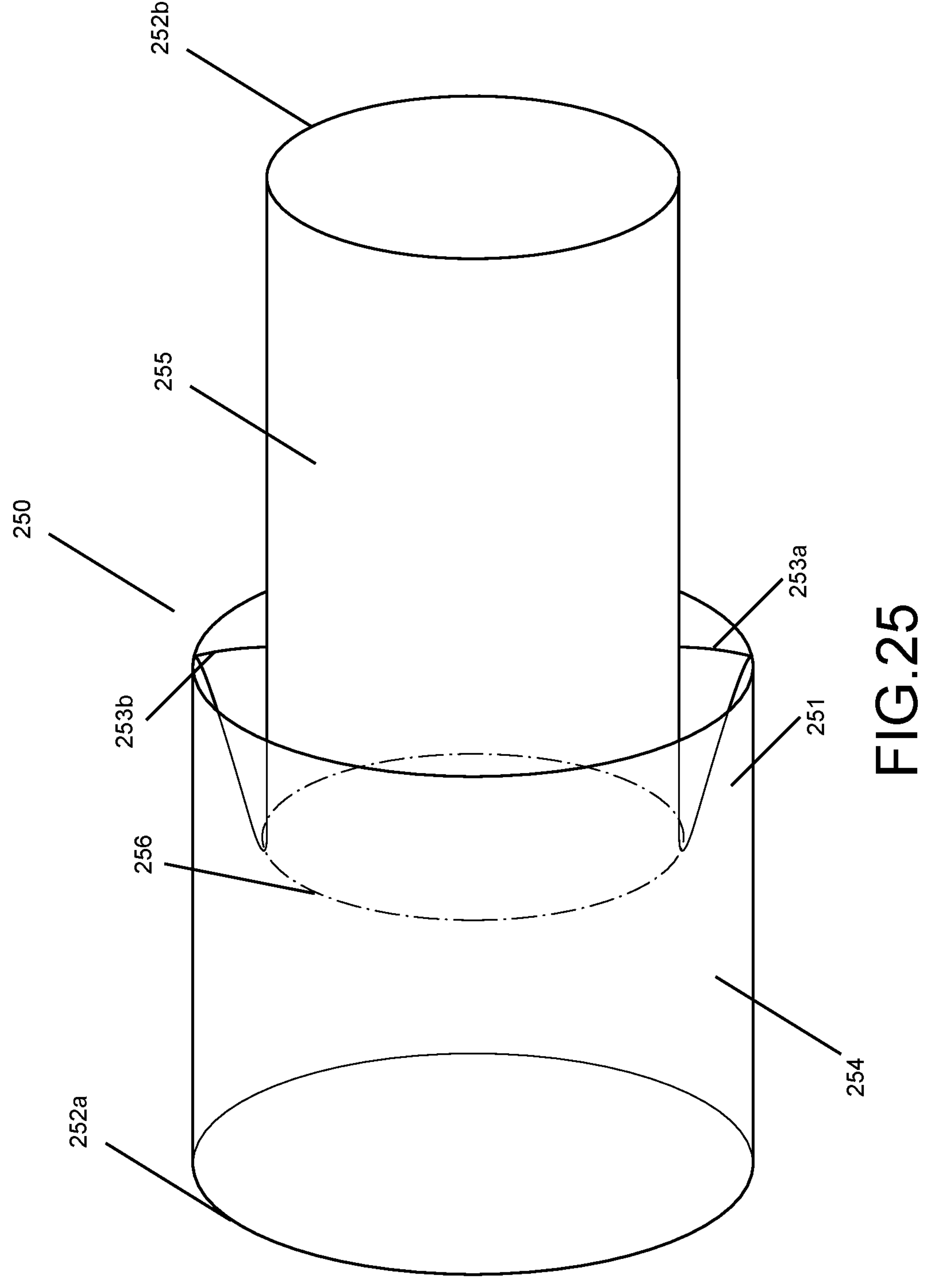
FIG. 25 is an illustration of a "tube"-shaped outer surgical drape having two open ends or mouths, according to embodiments of the present disclosure.

Referring now to FIG. 25, a "tube"-shaped outer surgical drape 250, having two open ends or mouths 252*a,b*, is illustrated. In the illustrated embodiment, the outer drape 250 is approximately cylindrical and defines an interior volume having a circular or elliptical cross-section. The outer drape 250 is provided with a circumferential perforation 256, provided at any point along a longitudinal axis of the outer drape 250 between first open end or mouth 252*a* and second open end or mouth 252*b*. Similar to the embodiment illustrated in FIG. 24, a circumferential overlapping protective element 251, e.g. a circumferential Z-fold or "double overbite" pleat, protects and maintains the sterility of an outer portion 254 and an inner portion 255 proximate to the circumferential perforation 256. When operating room personnel break the break tabs 253*a,b* (or other similar feature) and pull on or otherwise place in tension inner portion 255 (and optionally outer portion 254), the outer 254 and inner 255 portions separate along circumferential perforation 256, and the edges and surfaces of both portions that were proximate to circumferential perforation 256 (and thus maintained sterile by overlapping protective element 251) fall away from the covered, draped, and/or protected item of surgical equipment. Similar to the embodiment illustrated in FIG. 24, the outer drape 250 illustrated in FIG. 25 may, but need not always, cover an inner drape, and the outer drape 250 and inner drape (if any) may cover and maintain the sterility of any suitable surgical apparatus, device, and/or machine.

Figure 26:
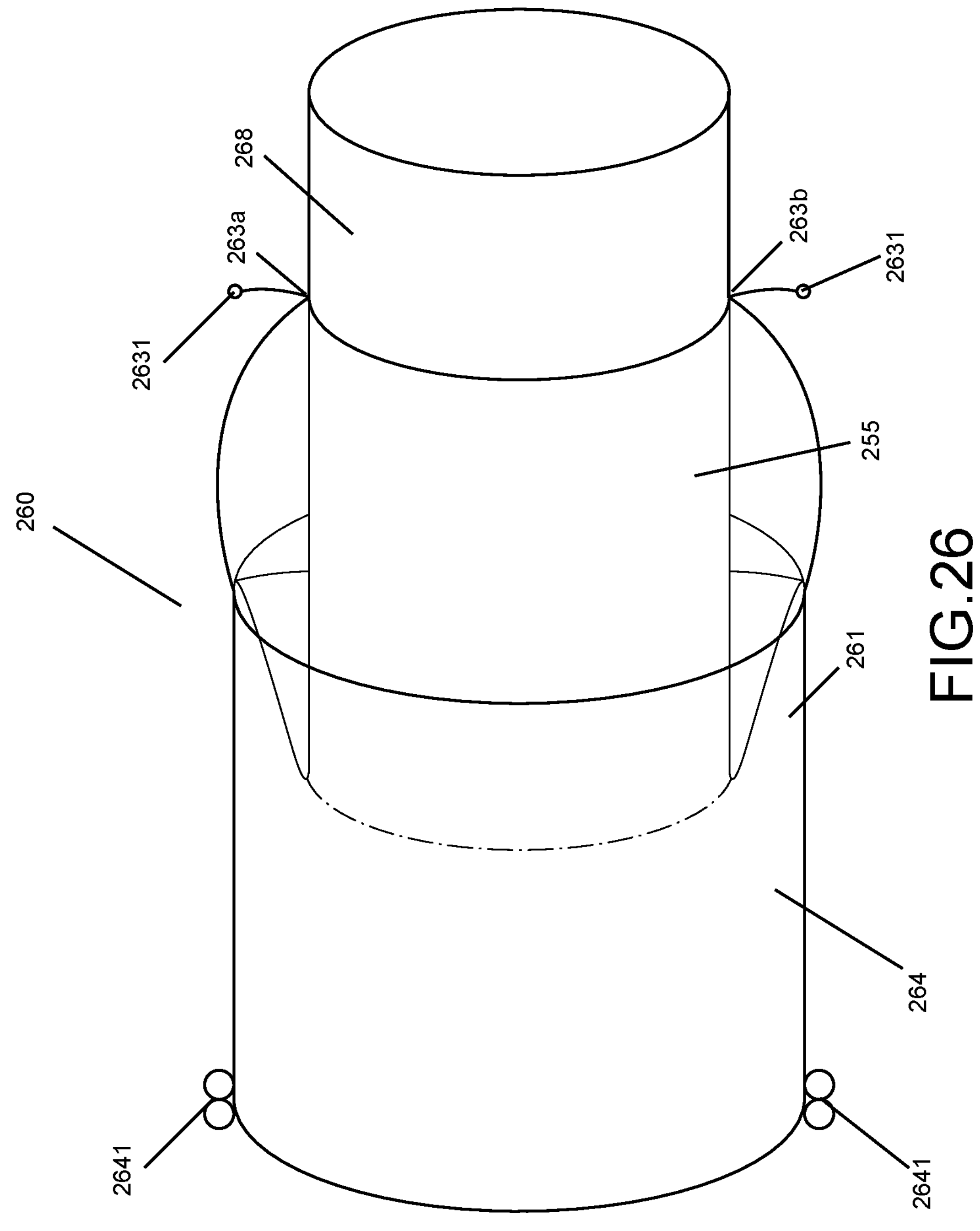
FIG. 26 is an illustration of a single-use disposable outer surgical drape having a circumferential Z-fold pleat and an elastic element, according to embodiments of the present disclosure.

Referring now to FIG. 26, a single-use disposable outer surgical drape 260 is illustrated, similar to the bag-type embodiment illustrated in FIG. 24. However, the outer drape 260 illustrated in FIG. 26 is different from the embodiment illustrated in FIG. 24 in several ways. First, outer drape 260 is adapted to be removed by pulling outer portion 264 instead of or in addition to inner portion 265 (and handles 2641 are optionally provided for this purpose). Second, additional handles 2631 are provided in association with break tabs 263*a,b* to assist in separating the break tabs 263 and "pulling back" Z-fold 261. Finally, an optional element, namely an elastic element 268, is provided in association with open end or mouth 262 to assist operating room personnel in placing the outer drape 260; a tightening mechanism (not shown), e.g. a strap, may be provided to allow operating room personnel to selectively tighten the open end or mouth 262.

Figure 27:
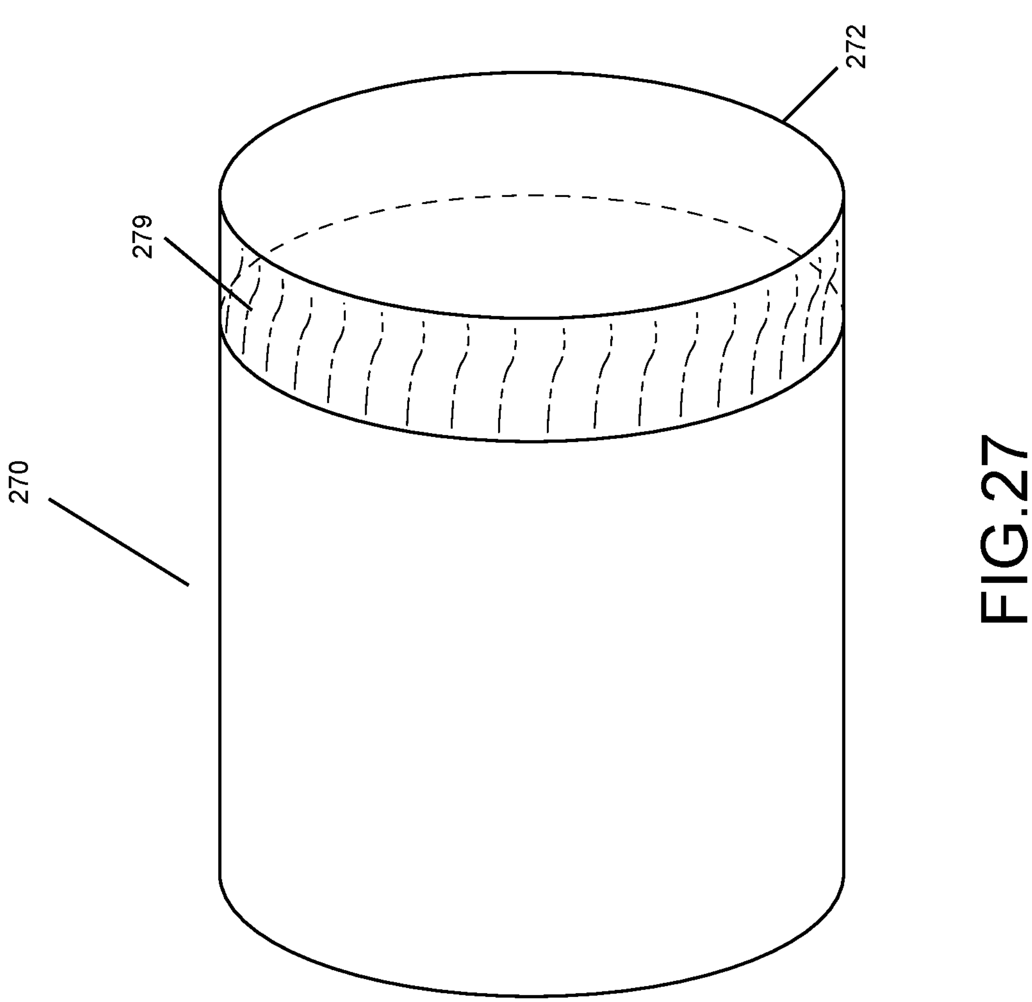
FIG. 27 is an illustration of a single-use disposable outer surgical drape having a circumferential Z-fold pleat and a circumferential cuff, according to embodiments of the present disclosure.

Referring now to FIG. 27, a single-use disposable outer surgical drape 270 is illustrated, similar to the bag-type embodiment illustrated in FIG. 24. In this embodiment, a circumferential cuff 279 is provided in association with open end or mouth 272; it is to be expressly understood that this circumferential cuff 279 may be provided instead of or in addition to other features associated with an open end or mouth of the outer drape, e.g. inner portion handles 247 as illustrated in FIG. 24 or elastic element 268 as illustrated in FIG. 26. The circumferential cuff 279 permits operating room personnel to place their hands under the circumferential cuff 279 and grasp an edge of the open end or mouth 272 or a feature associated therewith, e.g. handles or an elastic element, thereby making it easier for operating room personnel to spread or widen the open end or mouth 272 during placement of the drape and preventing contamination of the hands of operating room personnel due to any contaminants present on the open end or mouth 272.

Figure 28:
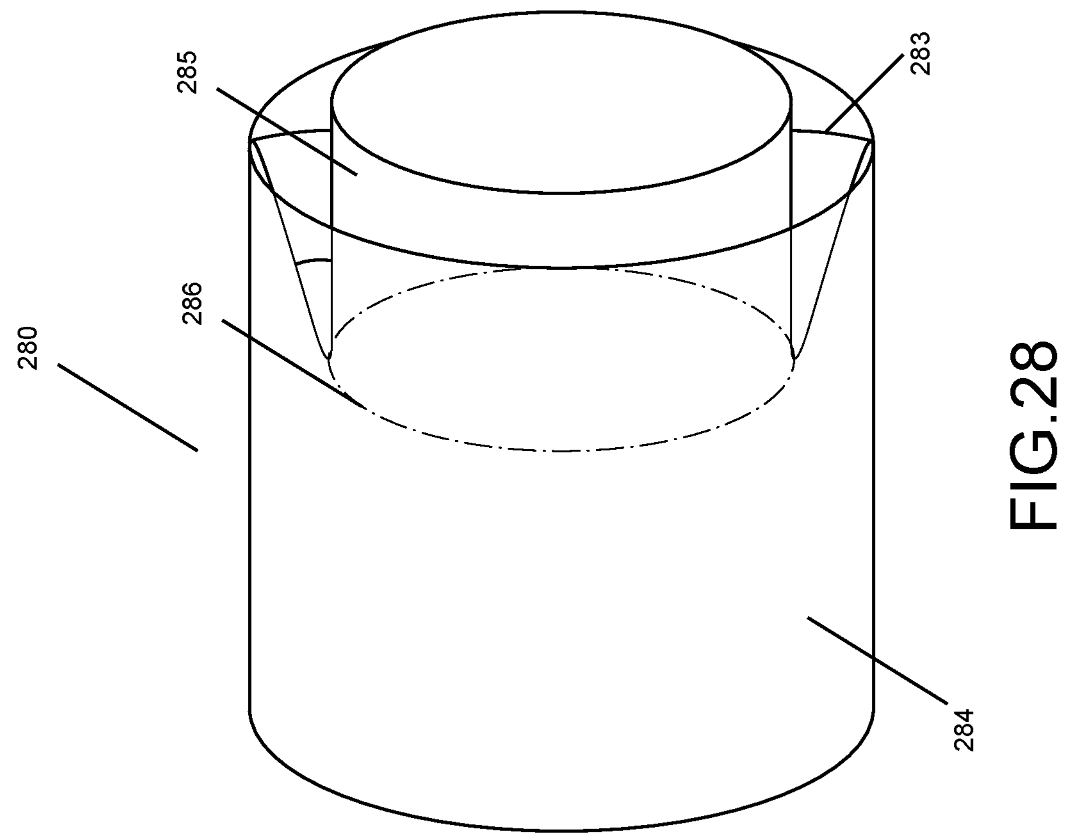
FIG. 28 is an illustration of a single-use disposable outer surgical drape having a circumferential Z-fold pleat and a "peel-away" adhesive element, according to embodiments of the present disclosure.
Figure 29:
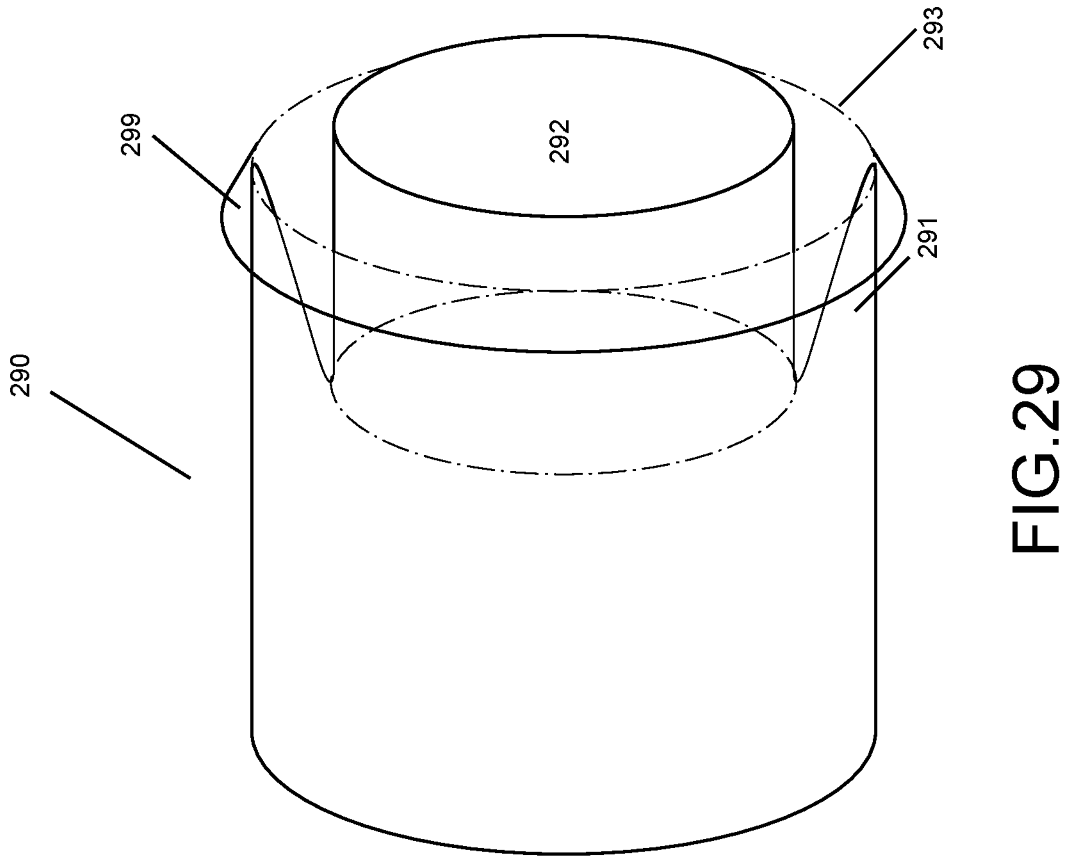
FIG. 29 is an illustration of a single-use disposable outer surgical drape having a circumferential Z-fold pleat and second perforations, according to embodiments of the present disclosure.
Figures 30A, 30B, 30C, 30D:
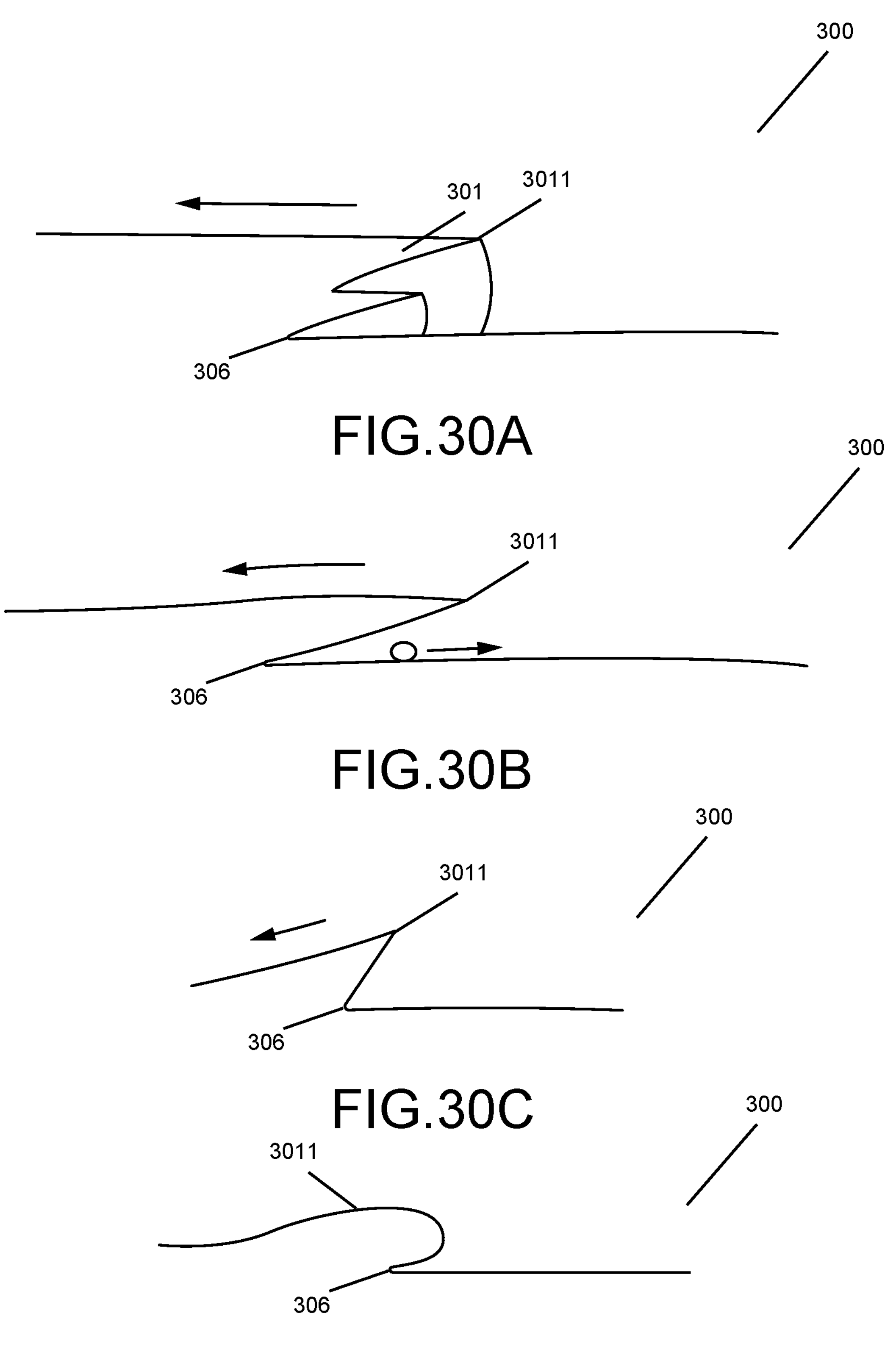
FIGS. 30A through 30D are illustrations of a "roll-back" Z-fold for a surgical drape being unfolded or "rolled back," according to embodiments of the present disclosure.

Referring now to FIGS. 28 and 29, embodiments of single-use disposable outer surgical drapes 280, 290 are illustrated, similar to the bag-type embodiment illustrated in FIG. 24. In FIG. 28, the break tabs 243*a,b* have been replaced with a "peel-away" adhesive mechanism 283; this mechanism may permit the non-sterile open end or mouth 242 (not shown in FIG. 28) to "roll" away from the circumferential perforation 286 and thus from the separating edges of inner and outer portions 284, 285. In FIG. 29, a circumferential cuff 299 is provided and the break tabs 243*a,b* have been replaced with second perforation 293; use of second perforation 293 in place of the break tabs 243*a,b* illustrated in FIG. 24 allows operating room personnel to spread or widen the open end or mouth 292 during placement of the drape without prematurely disengaging or "pulling back" the circumferential Z-fold 291. It is to be expressly understood that second perforation 293 may consist of a single continuous perforation, disposed around an entirety or only a portion of a circumference of the drape 290, or second perforation 293 may comprise two or more discrete perforated portions disposed about at least a portion of the circumference of the drape 290.

Referring now to FIGS. 30A through 30D, a process for using an embodiment of a "roll-back" Z-fold 301 for a surgical drape 300 is illustrated. In this embodiment, a non-sterile or potentially non-sterile edge 3011 of the Z-fold 301 is configured to "peel away" or "roll back" from circumferential perforation 306. In this way, the possibility that debris may fall, during separation, from a tip of edge 3011 toward perforation 306, is eliminated; any such debris will instead "roll back" together with edge 3011, and the sterility of perforation 306 is guaranteed. The "roll-back" capability of this Z-fold pleat 301 may be achieved by providing an adhesive element on an underside of Z-fold pleat 301, a series of break tabs arranged in a pattern and configured to be broken in a sequence that allows for rollback of edge 3011, or any of a variety of other suitable separation mechanisms, e.g. a zipper storage bag-type mechanism. In some embodiments, the "roll-back" Z-fold 301 may permit operating room personnel to unfold the Z-fold 301, separate the portions of the drape 300 along perforation 306, and remove the drape 300 from the underlying sterile field or equipment in a single smooth, continuous motion, preferably with one hand. It is to be expressly understood that this "roll-back" mechanism may be incorporated into a fold of any suitable shape, i.e. the "roll-back" edge may be included in surgical drapes that do not comprise a Z-fold pleat, "double overbite" fold, or similar feature; by way of non-limiting example, a "roll-back" edge may be incorporated into the separation mechanism illustrated in FIG. 12 of U.S. patent application Ser. No. 14/280,416.

Referring now to FIGS. 31-37, a single-use disposable outer surgical drape 310 having a circumferential Z-fold pleat 311 is illustrated. In the illustrated embodiment, the outer drape 310 is covering and maintaining the sterility of a Mayo stand having surgical instruments thereon, and has a bag-type shape, i.e. has a single open end or mouth 312. To allow the surgical instruments on the Mayo stand to be used without compromising the sterility of the stand or instruments, the outer drape 310 must be removed in such a way that the open end or mouth 312, which may have been exposed to open air in the operating room for a prolonged period and thus may not be considered sterile, is not brought over or across the sterile surface of the stand or the sterile instruments thereon. To accomplish this, a perforation or a similar feature (e.g. break tabs) are provided, in conjunction with the circumferential Z-fold pleat 311, that secure an outer portion 314 of the drape to an inner portion of the drape 315 and may be broken or separated by operating room personnel, allowing the inner portion 315 to be pulled away from (in this illustration, to the left) the outer portion 314; the inner portion 315 then separates from the outer portion 314 along a circumferential perforation. With the inner portion 315 removed (as illustrated, to the left), the outer portion 314, under its own weight, falls away from the surface of the stand, i.e. the Z-fold pleat 311 falls in the direction of the non-sterile open end or mouth 312. In this way, the non-sterile open end or mouth 312 is never brought into close proximity with the sterile surface of the stand or the sterile instruments thereon, thereby preserving the sterility of the surface and instruments. It is to be expressly understood that the outer drape 310 illustrated in FIG. 31 may, but need not always, cover an inner drape, and that the outer drape 310 and inner drape (if any) may cover and maintain the sterility of surgical apparatuses, devices, and/or machines other than Mayo stands.

Figure 31:
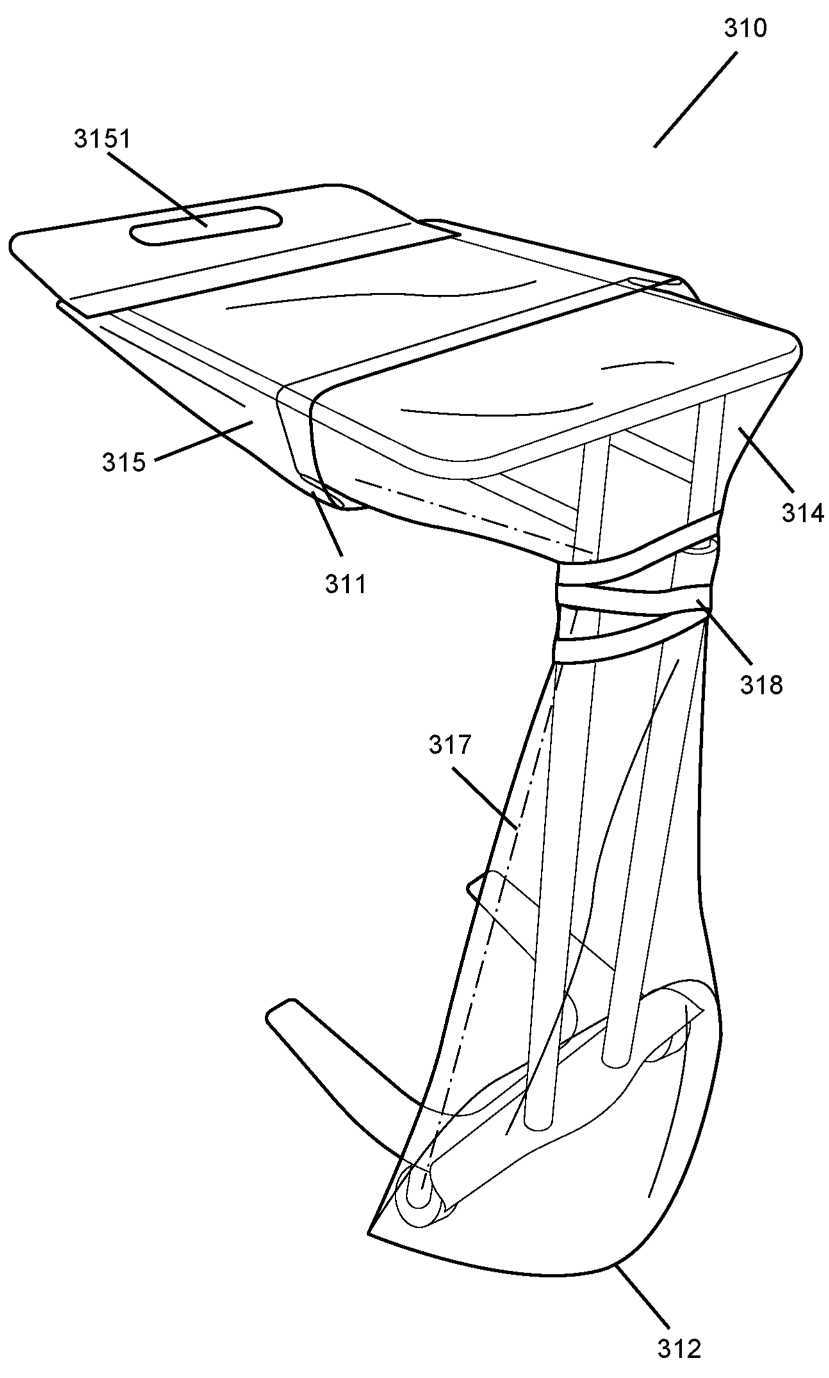
FIG. 31 is an illustration of a single-use disposable outer surgical drape 310 having a circumferential Z-fold pleat, according to embodiments of the present disclosure.

One significant additional feature of the single-use disposable outer surgical drape 310 having a circumferential Z-fold pleat 311 illustrated in FIG. 31 is a longitudinal or "inseam" perforation 317 in addition to the circumferential perforation. After the inner portion 315 is pulled away from the outer portion 314 and separated from the outer portion 314 along the circumferential perforation, and the outer portion 314 falls away from the surface of the stand under its own weight, the outer portion 314 may surround and/or be entangled with the legs of the Mayo stand, which impedes the portability of the Mayo stand during or after the surgical procedure. Inclusion of the longitudinal or "inseam" perforation 317, however, allows the outer portion 314 to be easily opened (e.g. by pulling or tearing) and removed from around the legs of the Mayo stand by operating room personnel, then subsequently discarded. When provided, the longitudinal or "inseam" perforation 317 maintains the sterility of the underlying Mayo stand and tools thereon by any means disclosed herein or known in the art, which may be similar to or different from the means by which the circumferential perforation maintains the sterility of the underlying Mayo stand and tools thereon.

In embodiments, the longitudinal or "inseam" perforation 317 comprises a portion that is weakened, or made of a material having a lower tear strength, than a remainder of the surgical drape 310, and may or may not comprise a score line. Such a weakened or tear-prone area would thus constitute a "fault line," i.e. an area that can be more readily torn and so represents an easy or convenient region for opening and/or separating the surgical drape 310. The longitudinal or "inseam" perforation may, but need not, include a visual indicator, i.e. a line or label, that allows operating room personnel to easily determine where the surgical drape 310 should be pulled or torn in order to be removed from around the Mayo stand.

Figure 33:
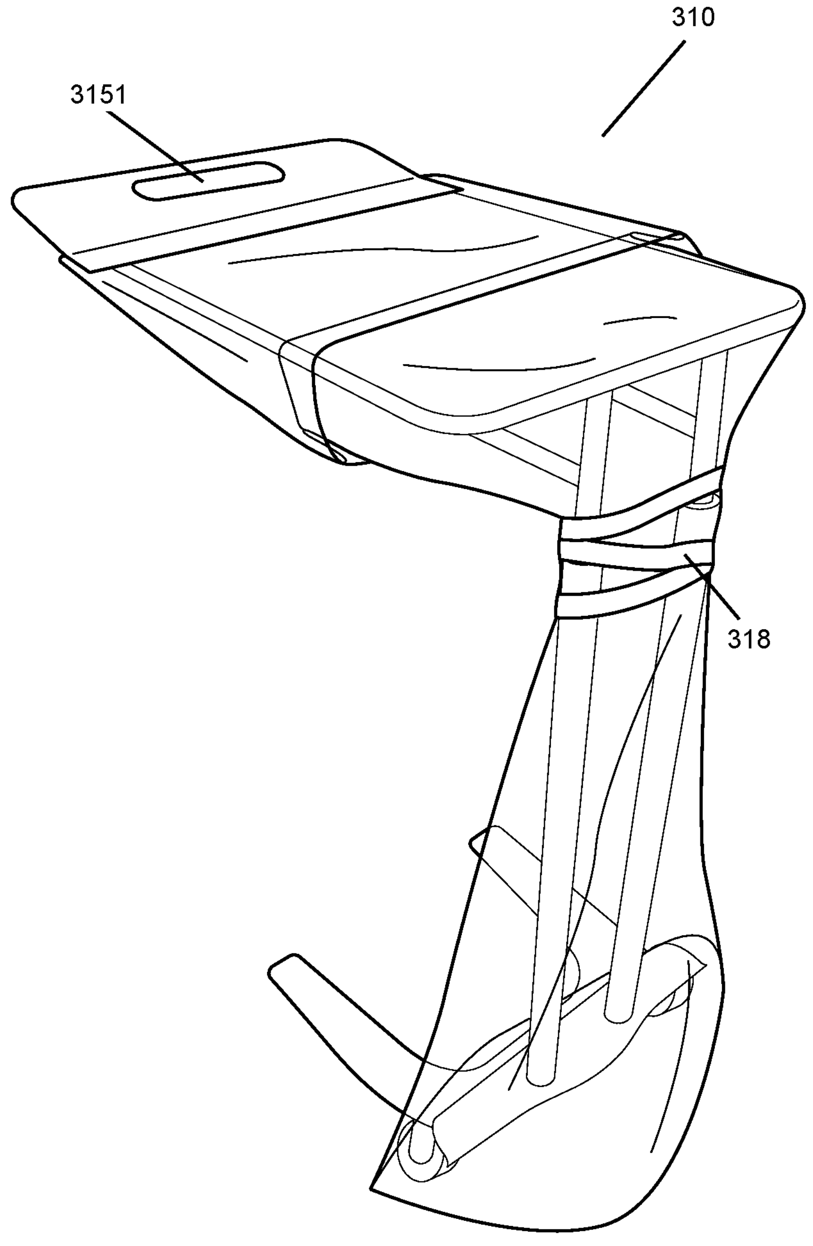
FIGS. 33, 34, and 35 are illustrations of a surgical drape having an inner portion handle and a cinch, according to embodiments of the present disclosure.
Figure 34:
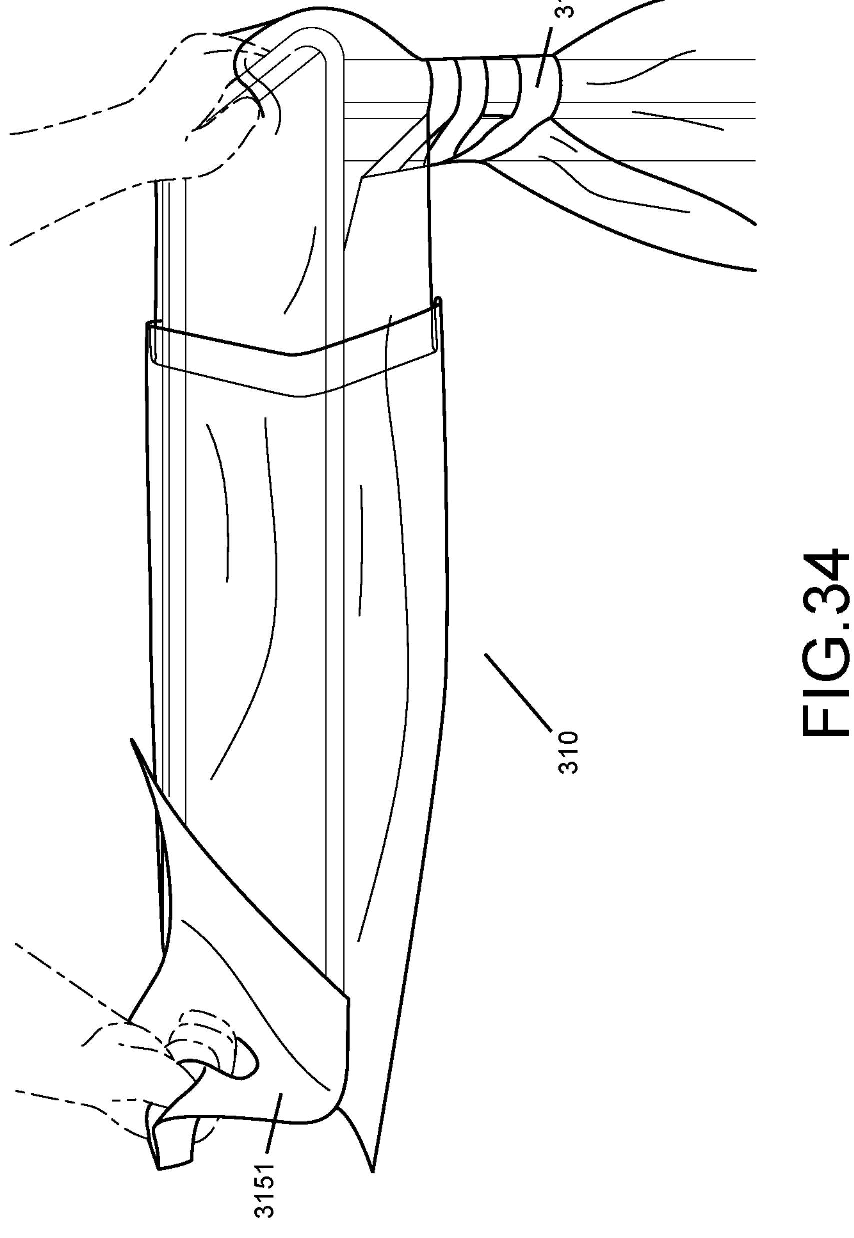
Figure 35:
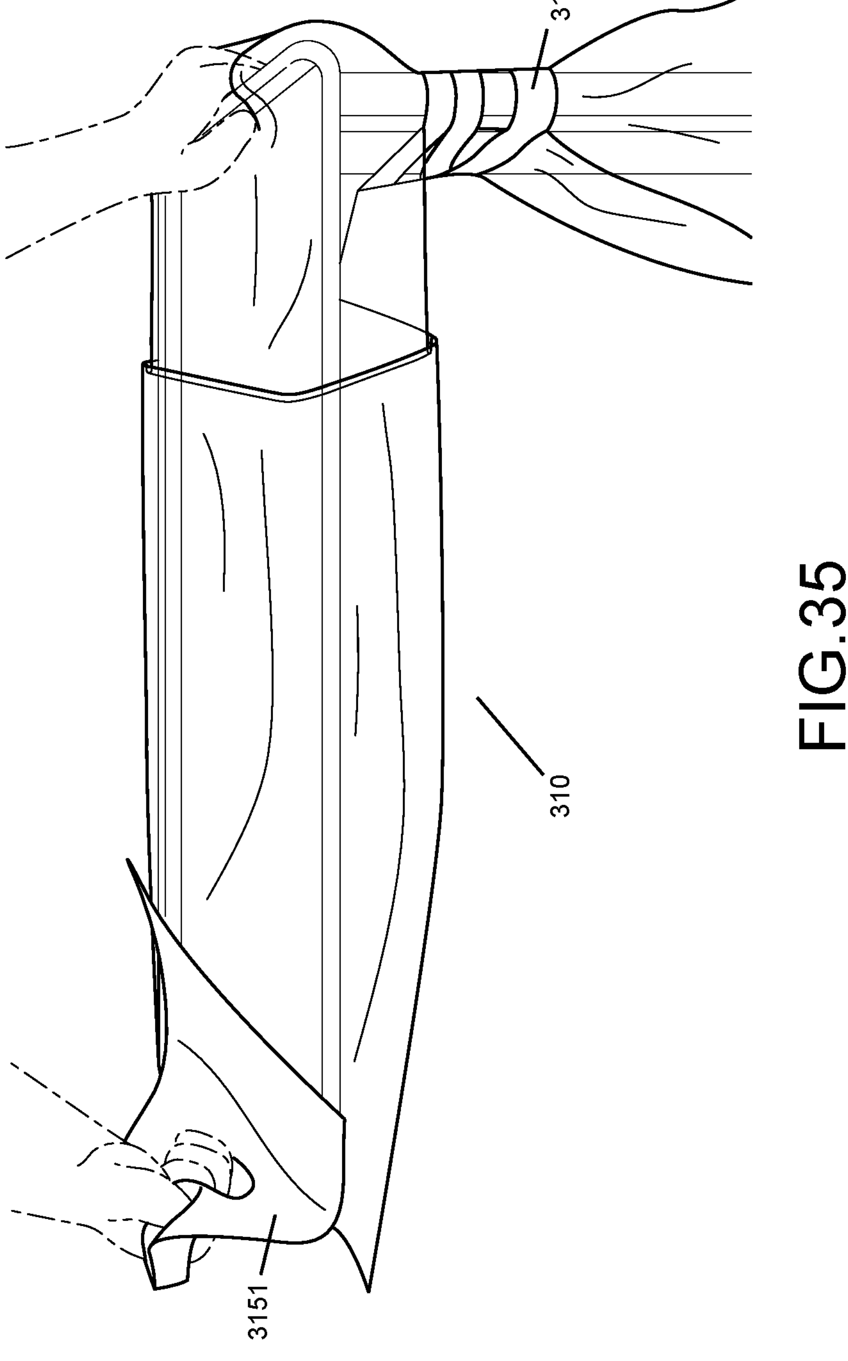
Figure 36:
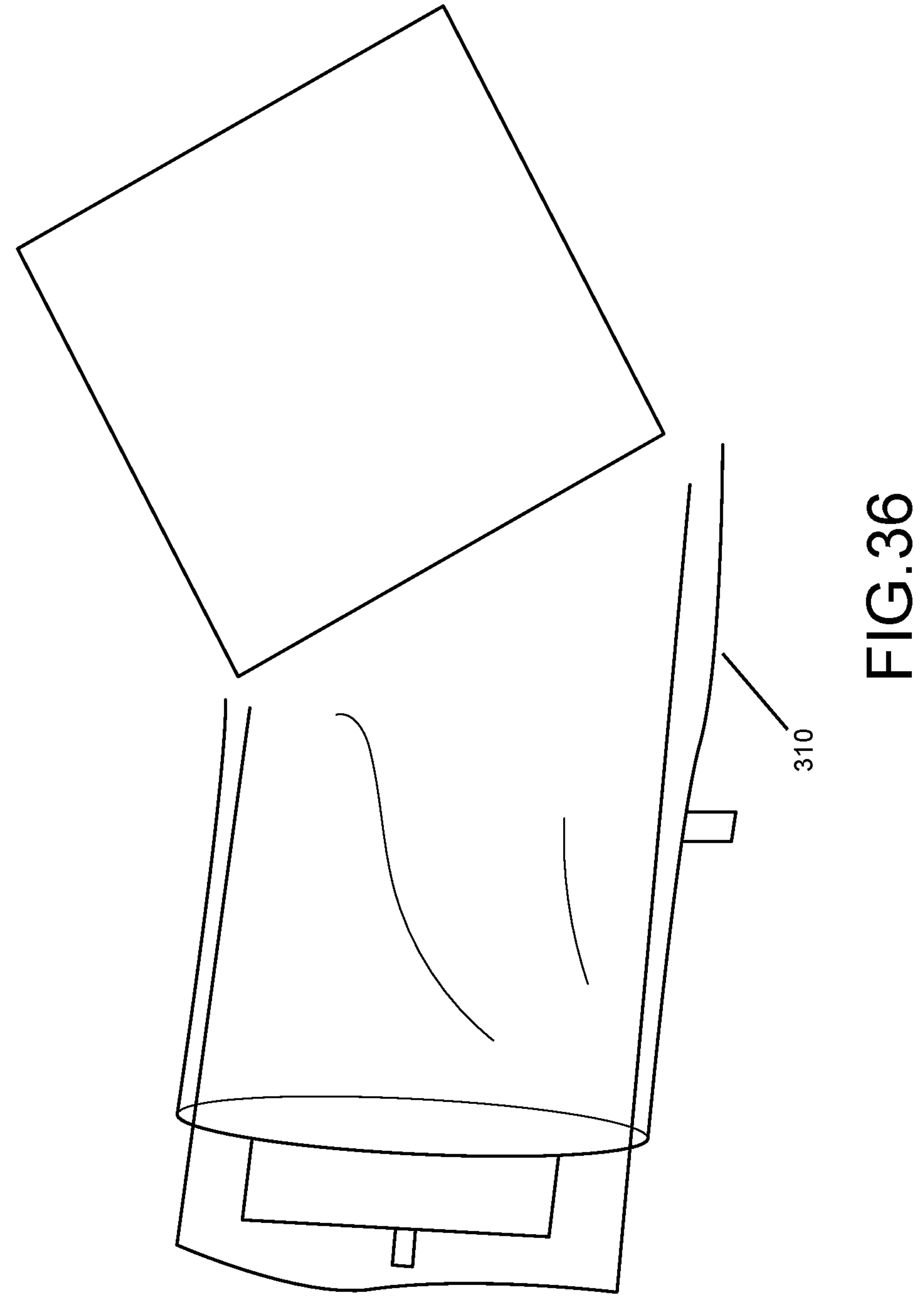
FIG. 36 is an illustration of a Mayo stand drape having an accommodation at a lower end of an outer portion thereof for tucking the lower end between legs of the stand, according to embodiments of the present disclosure.

In some embodiments, the surgical drape 310 illustrated in FIG. 31 may comprise a cinch 318, as illustrated in FIGS. 33-35. The cinch 318 is a tightening and/or attachment element that operating room personnel may use to tighten the surgical drape 310 around the legs of the Mayo stand and/or affix the surgical drape 310 to upper portions of the legs of the Mayo stand. The cinch 318 is positioned on the surgical drape 310 such that, when the surgical drape 310 is applied to the Mayo stand, there is sufficient vertical distance between the table surface of the Mayo stand and the cinch 318 to allow for easy separation of the portions of the surgical drape 310 overlying the table surface of the Mayo stand; the cinch 318 thus securely affixes the surgical drape 310 to the Mayo stand without impeding operating room personnel's ability to separate and remove the surgical drape 310 when desired. The cinch 318 may take the form of any suitable tightening and/or attachment element, including, by way of non-limiting example, any one or more of a strap, an adhesive element, a lacing or tying element, and/or an elastic element (e.g. a rubber band-like element), and may be provided with a closing or securing element (e.g. adhesive devices, pins, clips, snaps, hooks, loops, hook and loop devices, velcro, magnetic strips, etc.) that keeps the cinch 318 secured in place and prevents inadvertent or premature disengagement of the cinch 318.

In embodiments, the cinch 318 and/or other features of the surgical drape 310 illustrated in FIG. 31 may be designed and/or configured to cover and affix to a Mayo stand having a particular geometry. By way of first non-limiting example, where the Mayo stand is a "single-leg" Mayo stand (i.e. has a single upright interconnecting the table surface to the base), there may be two cinch elements 318 at two different vertical points of the outer portion 314, e.g. approximately one-third and approximately two-thirds along a vertical extent of the outer portion 314 and/or the upright of the Mayo stand; operating room personnel may, in their discretion, thus affix the surgical drape 310 to the Mayo stand using either the upper or lower cinch 318, or both. By way of second non-limiting example, where the Mayo stand is a "double-leg" Mayo stand (i.e. has two uprights interconnecting the table surface to the base), the surgical drape 310 may include an accommodation at a lower end of the outer portion 314, illustrated in FIG. 36, that may permit the lower end to be "tucked" between the legs of the Mayo stand to reduce the quantity of loose material, reduce tripping hazard, reduce the footprint of the surgical drape 310, more completely occlude the bottom portion of the drape and/or close an open mouth or end of the drape, etc.; such an embodiment can, of course, also be used with a single-leg Mayo stand, in which case the accommodation will not be used. In these and other embodiments, the purpose of these varying designs of the cinch 318 and/or surgical drape 310 is to ensure that the surgical drape 310 is securely affixed to the Mayo stand about a mid-portion of the upright of the Mayo stand.

A particularly advantageous and beneficial feature of the cinch 318 is that it may be easily broken or torn prior to or during separation of the surgical drape 310 along the circumferential perforation. In this way, the cinch 318 may secure the surgical drape 310 to the Mayo stand until separation and removal of the surgical drape 310 is desired, e.g. at a point in a surgical procedure when tools on the table surface of the Mayo stand must be accessed and used, whereupon separation and removal of the surgical drape 310 is facilitated by easy detachment or disengagement of the cinch 318. By way of first non-limiting example, the cinch 318 may take the form of a strap or band made of a tearable material, e.g. a tearable plastic or paper material, such that operating room personnel may break or tear the strap, then separate the surgical drape 310 about the circumferential perforation (and, if included, the longitudinal or "inseam" perforation 317). By way of second non-limiting example, the cinch 318 may take the form of one or more adhesive tabs, i.e. break tabs, that adhere to one or more legs of the Mayo stand (but do not cross over circumferential perforation or, if provided, longitudinal or "inseam" perforation 317) such that operating room personnel may easily break open the adhesive tab and thus disengage the cinch 318 at a desired time.

Figure 32:
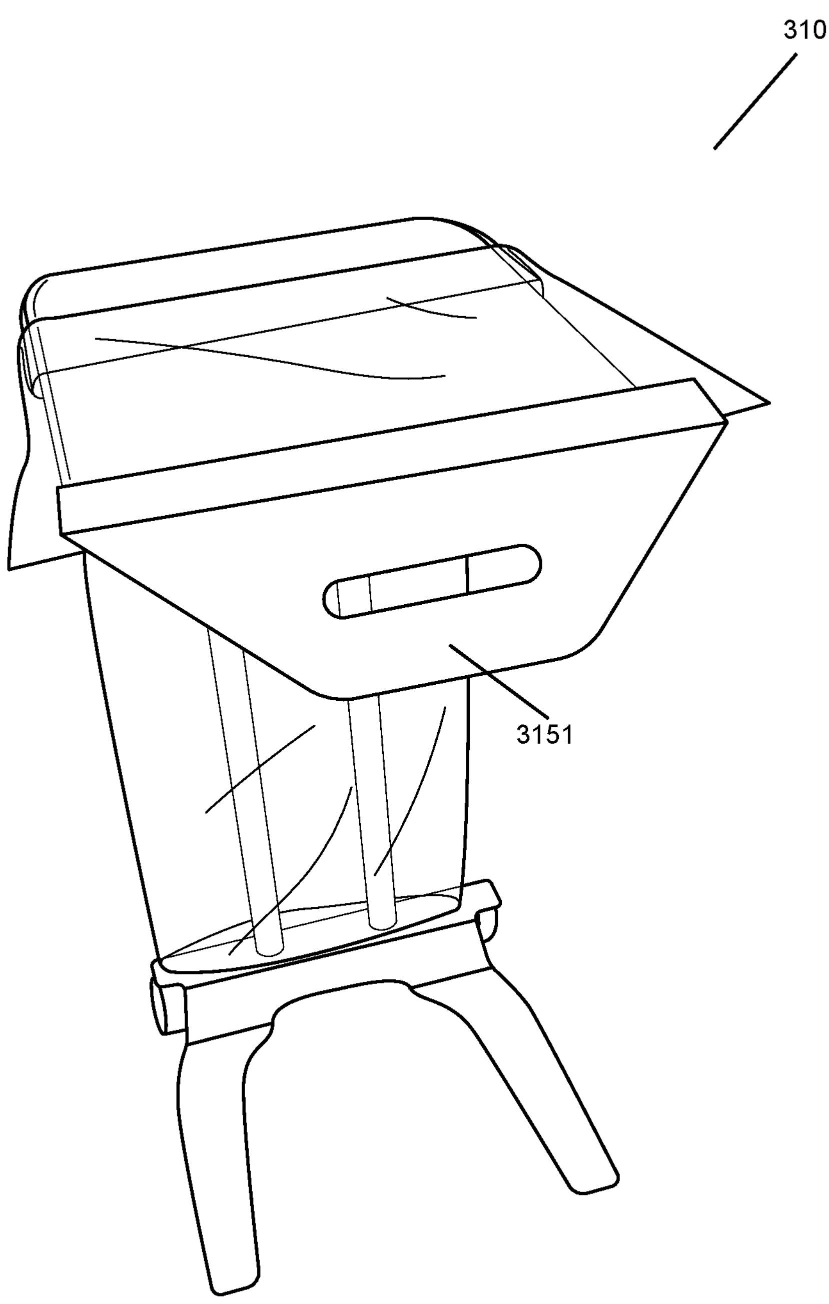
FIG. 32 is an illustration of an inner portion of a surgical drape having an inner portion handle, according to embodiments of the present disclosure.

Referring now to FIGS. 32, 34, and 35, at least one inner portion handle 3151 may, but need not, be provided to assist operating room personnel in pulling the inner portion 315 away from the outer portion 314. Although the inner portion handle 3151 is illustrated in FIGS. 32, 34, and 35 as attached only to the top surface of the inner portion 315, it is to be expressly understood that one or multiple inner portion handles 3151 may be attached to only the top surface, only the bottom surface, or both the top and bottom surfaces of the inner portion 315. In embodiments, including the embodiments illustrated in FIGS. 32, 34, and 35, it may be particularly beneficial for the inner portion handle 3151 to have a width that is equal to or approximately equal to a width of the inner portion 315, which may aid operating room personnel in transmitting a pulling force, and thus disengaging the Z-fold, evenly and substantially simultaneously about the entire width of the inner portion 315.

Figure 37:
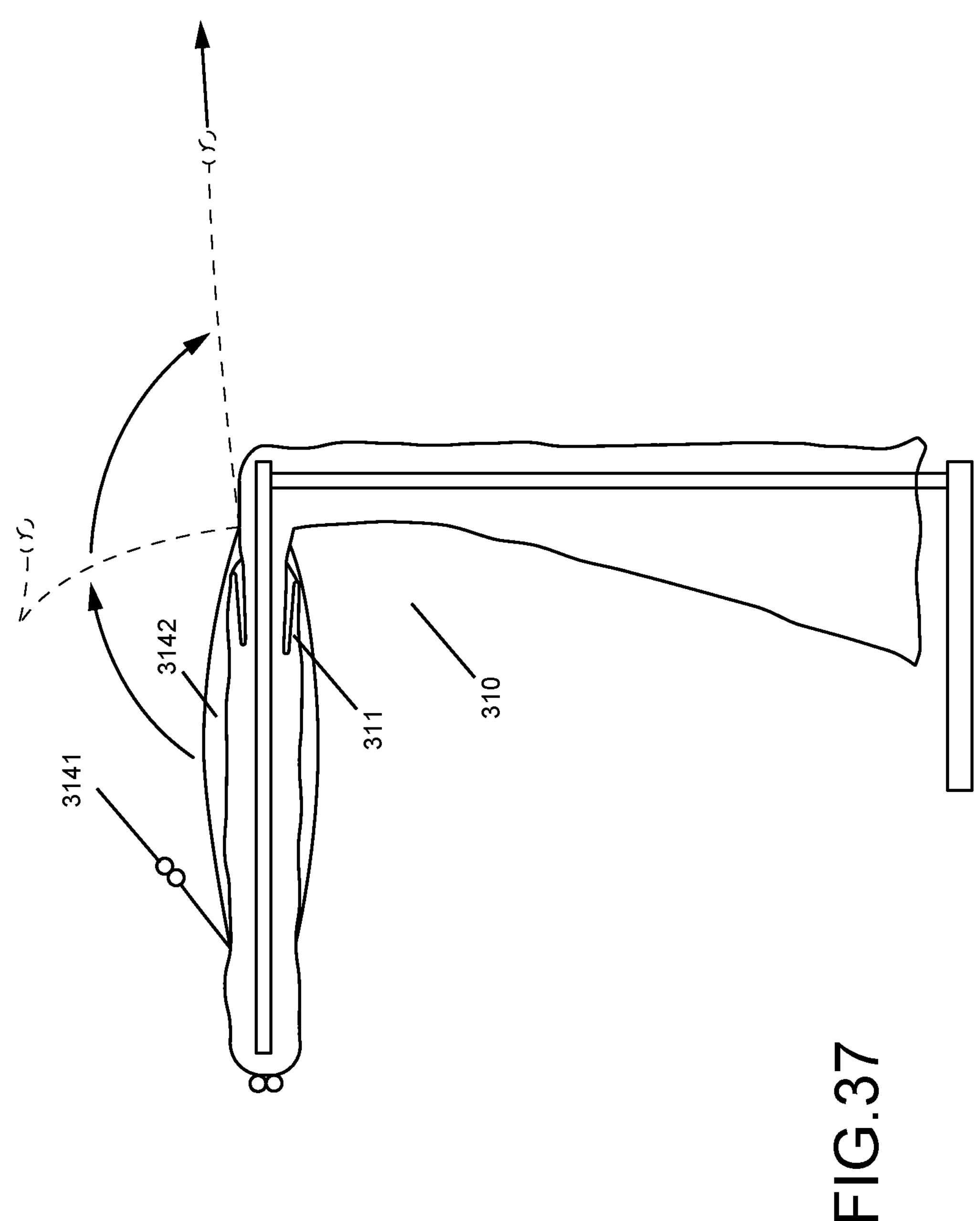
FIG. 37 is an illustration of a surgical drape having an outer portion handle and a dust cover, according to embodiments of the present disclosure.

The surgical drape 310 may also be adapted to be removed by pulling outer portion 314 instead of or in addition to inner portion 315, and at least one outer portion handle 3141, illustrated in FIG. 37, may be optionally provided for this purpose. Provision of an outer portion handle 3141 may be particularly helpful and advantageous when the surgical drape 310 is adapted to maintain the sterility of a Mayo stand. Specifically, Mayo stand covers having a handle at only a single end are typically removed by a single member of an operating team, who grips the tray or table surface of the Mayo stand itself with one hand while pulling the handle with the other hand; while such designs are suitable for separating the Mayo stand drape, they allow the user to remove only a portion (not the entirety) of the drape from around the surface of the Mayo stand. By using an outer portion handle 3141, the team member can fully separate the drape; by way of non-limiting example, as the team member pulls inner portion handle 3151 away from the Mayo stand with one hand, he or she may simultaneously pull outer portion handle 3141 away from the Mayo stand and downwardly with the other hand, thus completely exposing the table surface of the Mayo stand in a single step. (If one or more cinches 318 are provided with the surgical drape 310 in such embodiments, the team member may then disengage the cinches 318 to remove the surgical drape 310 from around the legs or uprights of the Mayo stand.) Provision of one or more outer portion handles 3141 may also allow for the surgical drape 310 to include a dust cover 3142 as part of the outer portion 314, as illustrated in FIG. 37.

Particularly, as illustrated in FIG. 37, outer portion handle 3141 may be attached to or incorporated into the dust cover 3142 and positioned at a leg or upright end of the Mayo stand, such that an operating team member can cause the dust cover 3142 to reflect away from the table surface by grabbing the outer portion handle 3141 and pulling in a direction opposite a direction in which the inner portion handle 3151 is pulled. This allows for reflection of the dust cover 3142 and separation of the circumferential perforation 316 in one single, fluid motion, and provides additional protection against accidental or premature unfolding of the circumferential Z-fold 311.

In general, surgical drapes 310 according to the embodiments illustrated in FIGS. 31-37 may have a diameter that is slightly larger than a corresponding dimension of the underlying Mayo stand (or other apparatus or device whose sterility must be maintained), such that the Mayo stand and tools thereon may easily fit within the surgical drape 310 but a cinch 318 (if provided) may be easily applied. By way of non-limiting example, surgical drapes 310 adapted to maintain the sterility of a Mayo stand that is 19 inches wide may have a circumference of, e.g., at least about 60 inches, so that the diameter of the surgical drape 310 is slightly longer than the 19-inch width of the Mayo stand. A length of the surgical drape 310 may also be selected to provide for coverage of substantially all of a height of the Mayo stand, taking into account, e.g., a height of an upright of the Mayo stand and/or the height of surgical tools and instruments arranged thereon.

Figure 38:
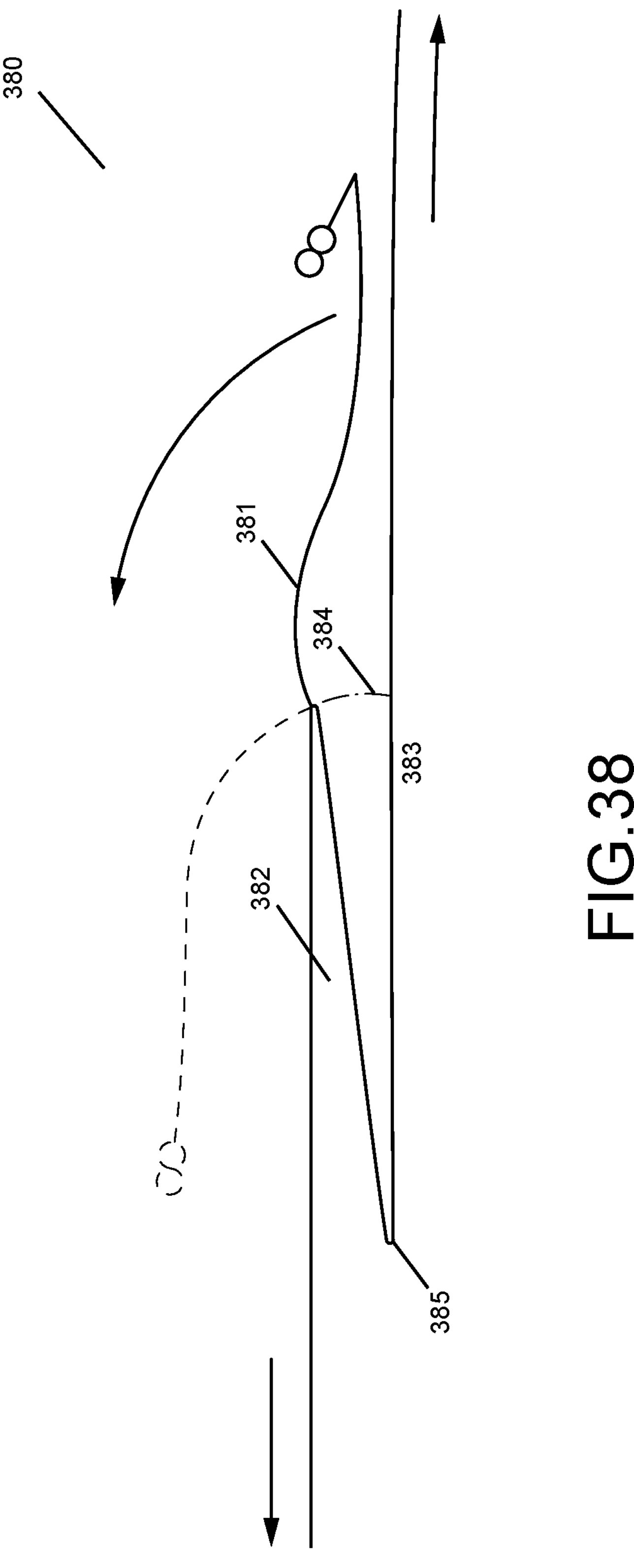
FIG. 38 is an illustration of a surgical drape for a surgical back table, according to embodiments of the present disclosure.

Referring now to FIG. 38, an embodiment of a surgical drape 380 for a surgical back table is illustrated. This embodiment includes a superior cover or dust cover 381 and a "locked" Z-fold 382. It is to be expressly understood that the dust cover 381 itself provides primary protection, and in some embodiments the only protection, against contamination to the underlying back table surface, and that it is not necessary for the Z-fold 382 to impart any additional contamination prevention characteristics (although it may do so in some embodiments as a secondary means of protecting the underlying back table). In the embodiment illustrated in FIG. 38, the dust cover 381 is a "peel-away" dust cover, which may be "peeled away" by pulling in a first direction (in this illustration, leftwardly). As illustrated in FIG. 38, the point of intersection between dust cover 381 and Z-fold 382 may initially be affixed to an inferior portion 383 by a perforation 384, which may be broken by "peeling away" the dust cover 381 (optionally, with the use of a dust cover handle provided for the purpose); this provides the "locking" of Z-fold 382, because the Z-fold 382 cannot be unfolded until the dust cover 381 is "peeled away." Once the dust cover 381 is "peeled away," the locked Z-fold 382 is exposed and unlocked, and the perforation 385 underlying the Z-fold 382 may be opened and the drape 380 separated by pulling in an opposing direction (in this illustration, rightwardly).

Figure 39:
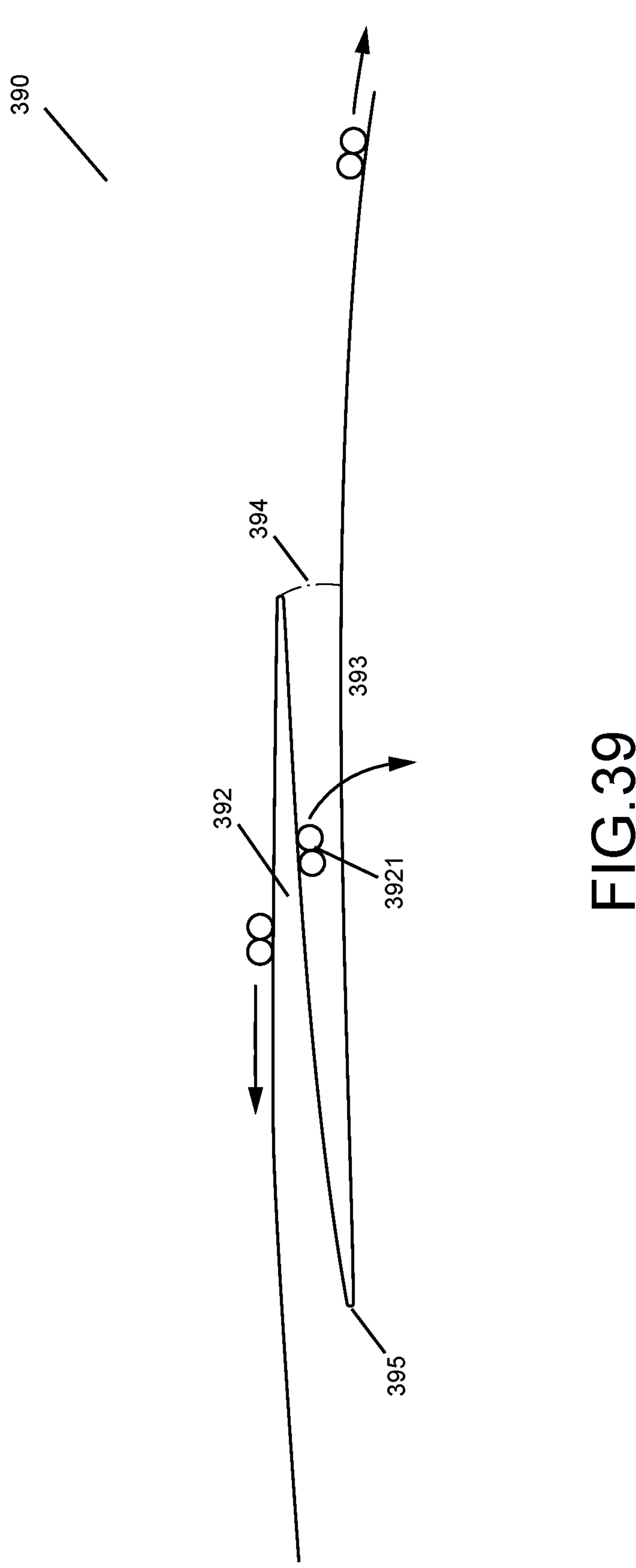
FIG. 39 is an illustration of another surgical drape for a surgical back table, according to embodiments of the present disclosure.

Referring now to FIG. 39, another embodiment of a surgical drape 390 for a surgical back table is illustrated. This embodiment includes a superior cover or dust cover (not shown) and a "locked" Z-fold 392. It is to be expressly understood that the dust cover itself provides primary protection, and in some embodiments the only protection, against contamination to the underlying back table surface, and that it is not necessary for the Z-fold 392 to impart any additional contamination prevention characteristics (although it may do so in some embodiments as a secondary means of protecting the underlying back table). As in the embodiment illustrated in FIG. 38, the dust cover is a "peel-away" dust cover, and the point of intersection between the dust cover and the Z-fold 392 is initially affixed to an inferior portion 393 by a perforation 394 (or a similar feature, such as a break tab), which may be broken by "peeling away" the dust cover. Unlike in the embodiment illustrated in FIG. 38, however, the embodiment illustrated in FIG. 39 includes a Z-fold handle 3921, disposed on an underside of an intermediate segment of the Z-fold 392, which becomes exposed and available to the operating room personnel once the Z-fold 392 is unlocked and unfolded; this handle permits the operating room personnel to pull in the same direction as the "peel-away" of the dust cover to separate the drape at underlying perforation 395. Such a design may be particularly advantageous where a width of the Z-fold and/or the width of the overlap between the dust cover and the inferior portion 393 is large (e.g. two feet or more), as it enables operating room personnel (either a single person or two people) to more easily separate the surgical drape 390 without requiring a long reach across the surgical drape 390.

Figures 40A, 40B:
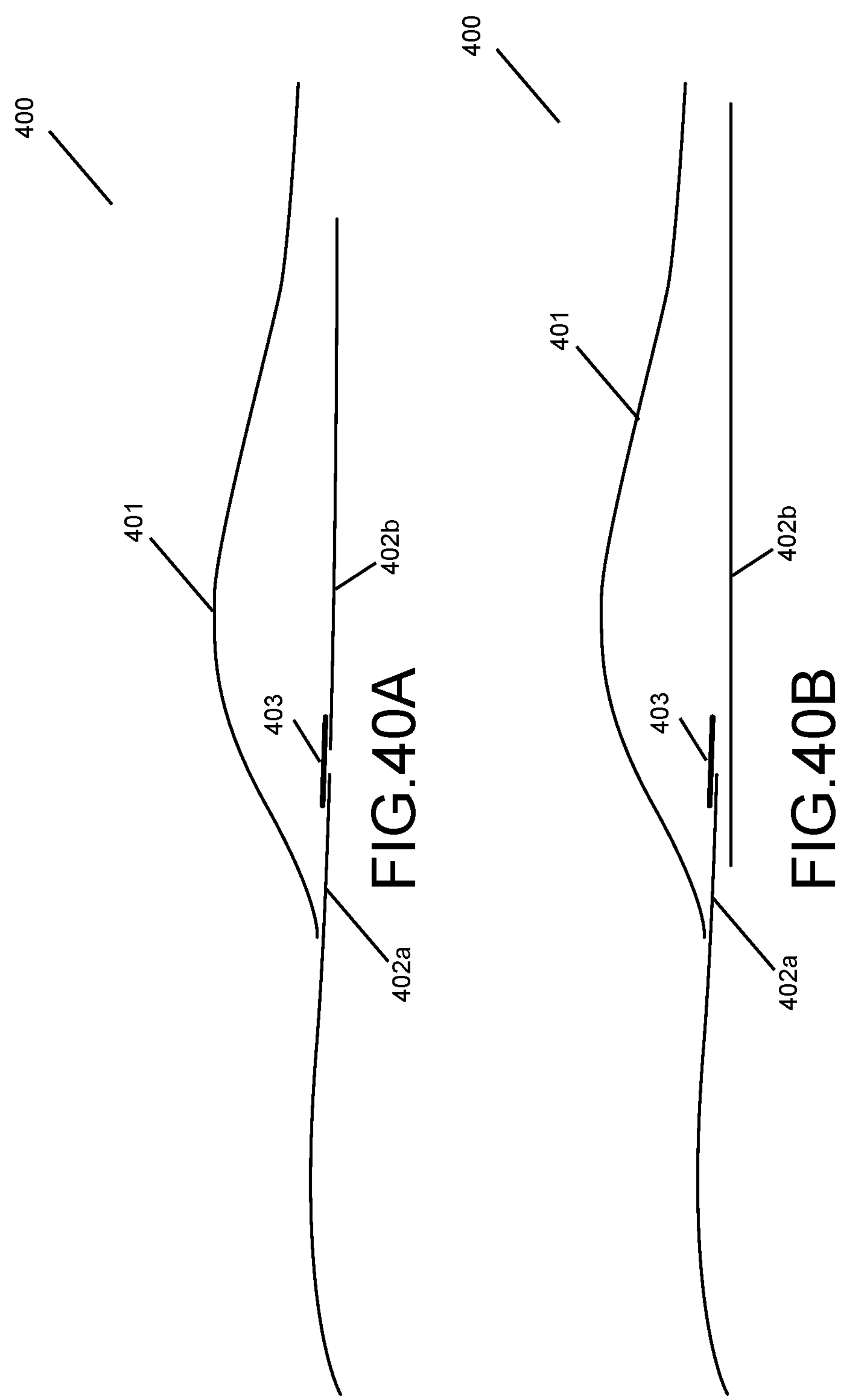
FIGS. 40A and 40B are illustrations of a process of using a surgical draping system having a separable attachment, according to embodiments of the present disclosure.

Referring now to FIGS. 40A and 40B, a process of using a surgical draping system 400 is illustrated in side view. The surgical draping system 400 may be used to maintain the sterility of any one or more of a surgical back table, a Mayo stand, a patient, and so on. In this embodiment, the draping system 400 comprises a superior drape or dust cover 401 and an inferior drape 402, the latter of which comprises two adjacent or overlapping inferior drape sheets 402*a,b* that are initially connected by a separable attachment 403, as illustrated in FIG. 40A. A Z-shaped protective fold is thus created by the arrangement of the superior drape 401 over the overlap or intersection of the inferior drape sheets 402*a,b*. This Z-fold may be disengaged, and the surgical draping system 400 may be separated, by separating the separable attachment 403, as illustrated in FIG. 40B. It is to be expressly understood that in the embodiment illustrated in FIG. 40, the separable attachment may take any suitable form, such as, by way of non-limiting example, any one or more of a break tab, low-strength adhesive, or other breakable element, or a tear line formed by a perforation in a single sheet of material that comprises both inferior drape sheets 402*a,b*.

Figure 41A:
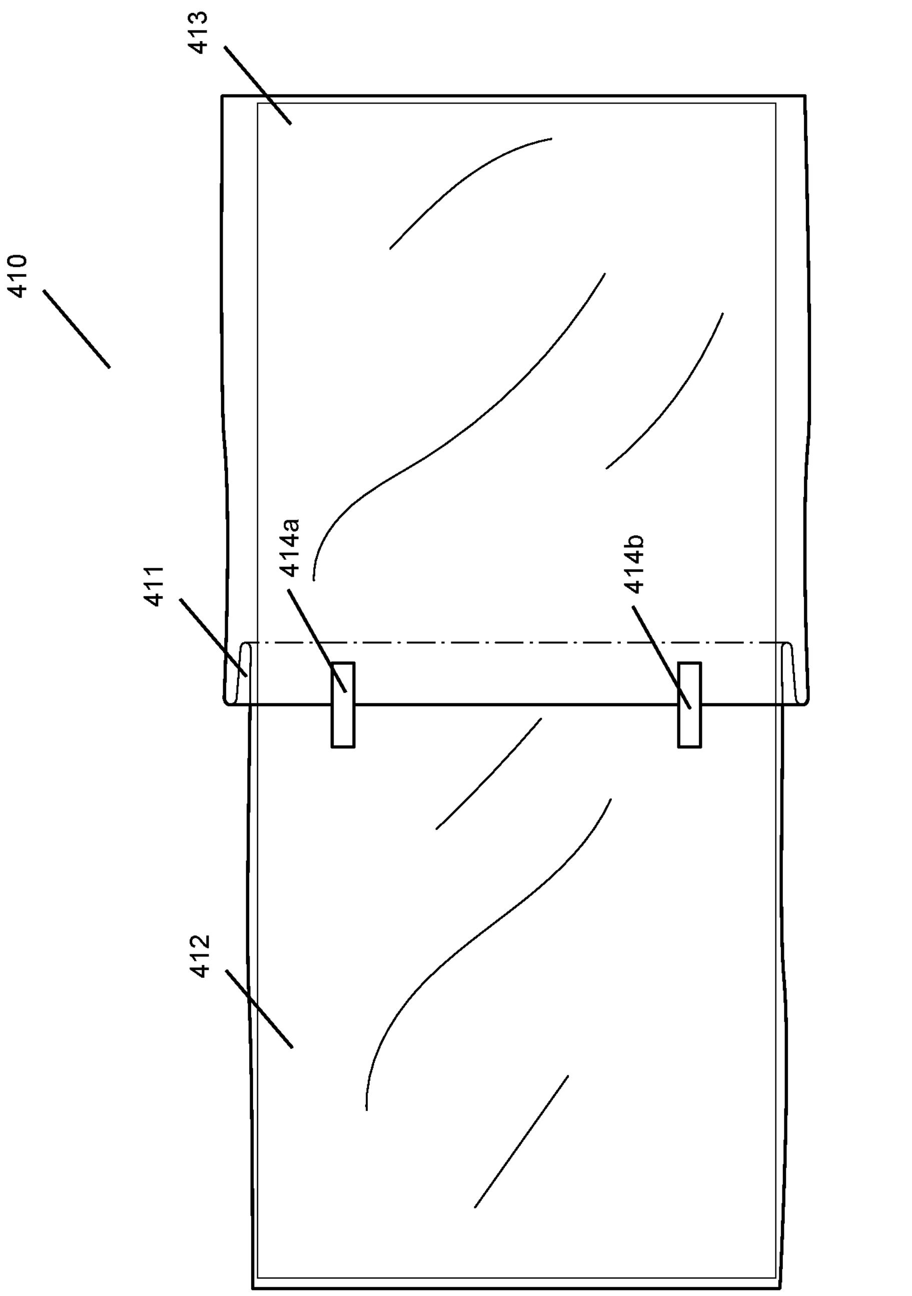
FIGS. 41A through 41C are illustrations of the use of a surgical drape having a "cinnamon role"-type fold, according to embodiments of the present disclosure.
Figure 41B:
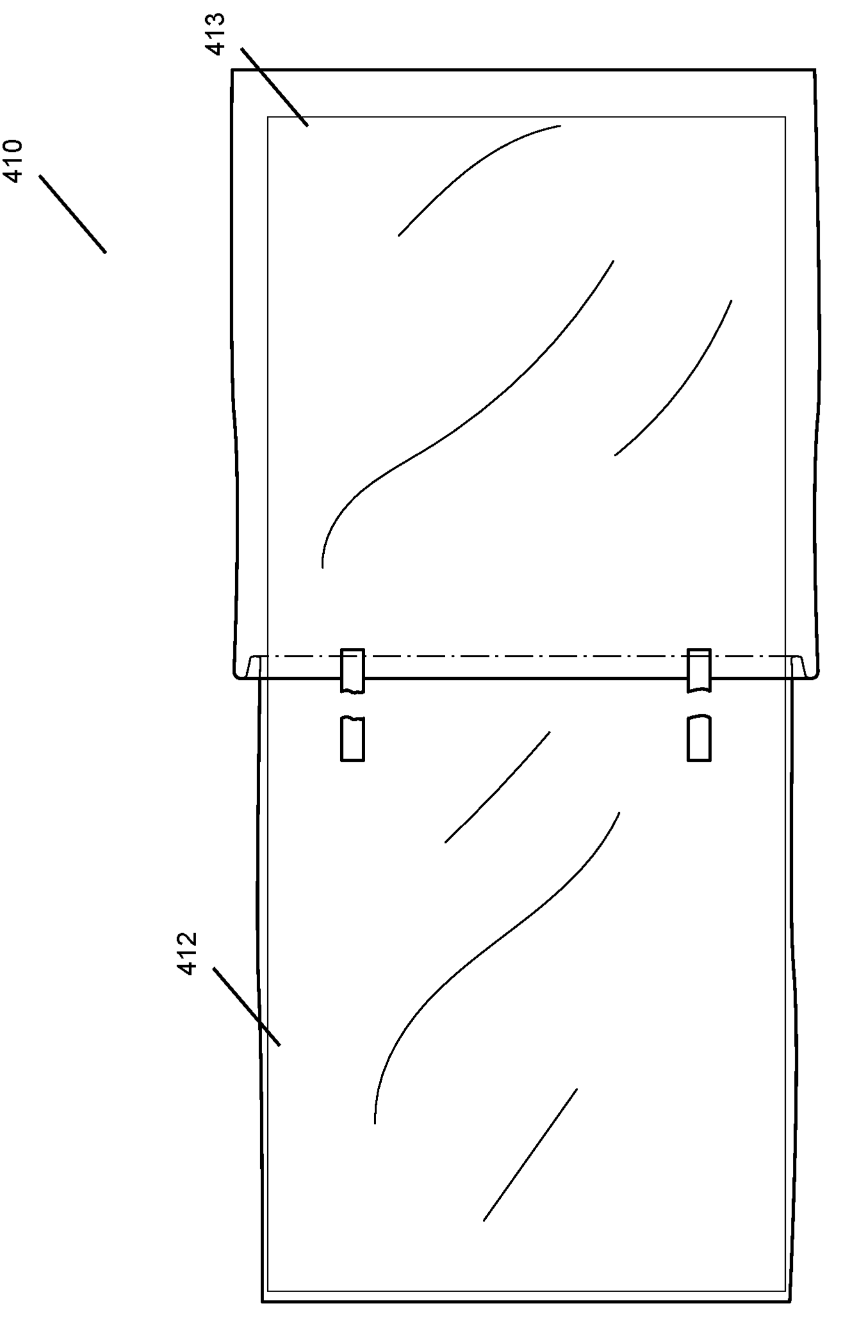
Figure 41C:
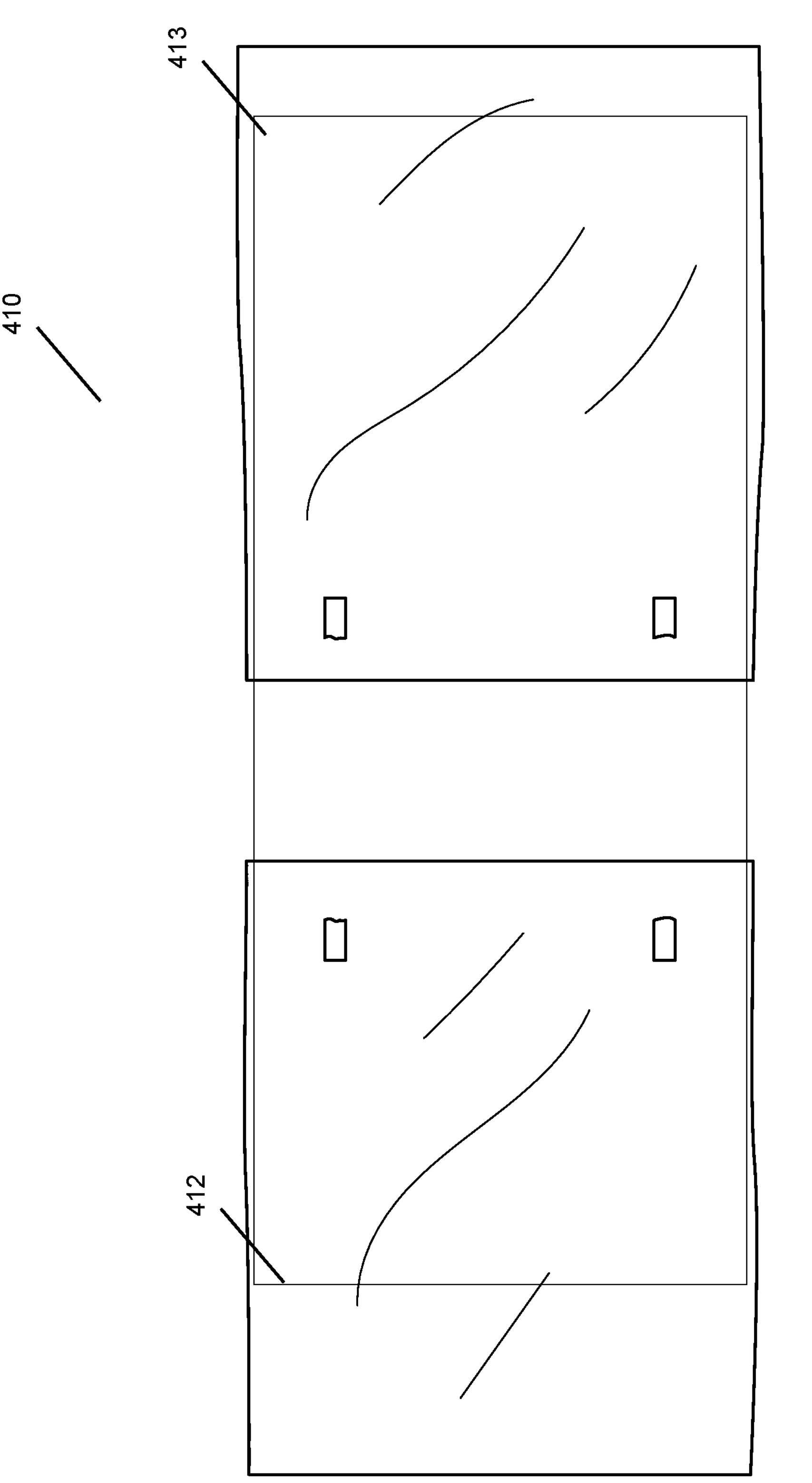

Referring now to FIGS. 41A through 41C, a surgical drape 410 comprising a "cinnamon roll"-type fold 411 is illustrated. The "cinnamon roll"-type fold 411 consists of a series of folds or a circular roll, whereby overlapping or concentric rolls or folds of an inner portion 412 of the drape 410 and an outer portion 413 of the drape 410 are tightly interspersed in a spiraling and/or interlocking manner to provide a secure connection between the inner portion 412 and the outer portion 413; as shown in FIGS. 41A through 41C, break tabs 414*a,b* or similar breakable adhesive features may be provided to maintain the "cinnamon roll"-type fold 411 in its folded configuration and prevent inadvertent or premature disengagement of the "cinnamon roll"-type fold 411. Once the break tabs 414*a,b* are broken, the portions of the drape 412, 413 may be pulled in opposing directions, which causes the rolls or folds forming the "cinnamon roll"-type fold 411 to be separated, thus opening and disengaging the "cinnamon roll"-type fold 411. It is to be expressly understood that the "cinnamon roll"-type fold 411 may comprise a perforation (e.g. where the inner and outer portions 412, 413 are each part of a single unitary but separable drape sheet), or may not comprise a perforation (e.g. where the inner and outer portions 412, 413 are each separate drape sheets held together only by the spiraling/interlocking interspersion of the "cinnamon roll"-type fold 411).

Figure 42:
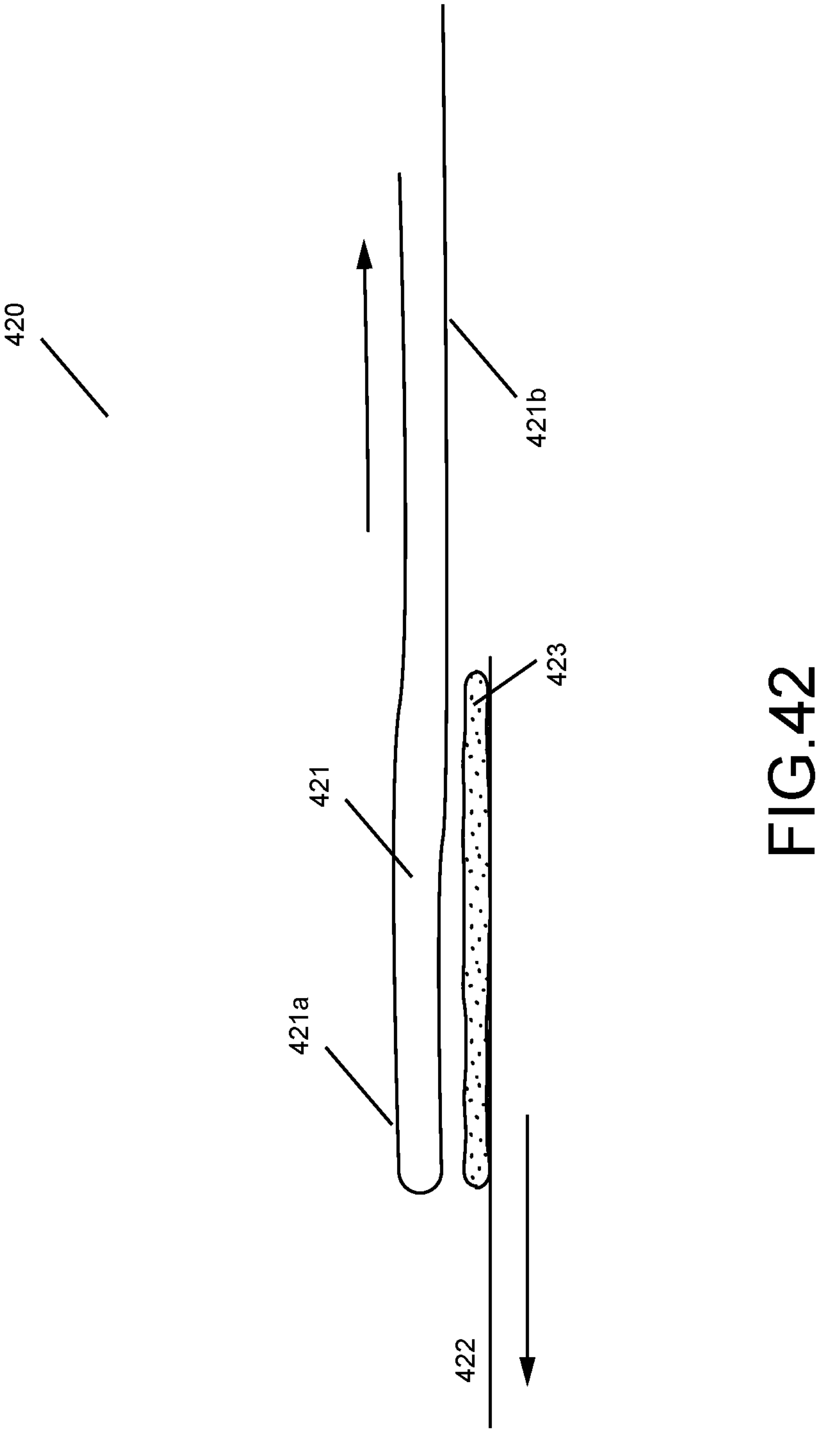
FIG. 42 is an illustration of a surgical draping system having two overlapping sheets, according to embodiments of the present disclosure.

Referring now to FIG. 42, a generalized schematic of a surgical draping system 420 comprising two overlapping sheets, a superior sheet 421 and an inferior sheet 422, is illustrated. As FIG. 42 illustrates, a superior edge 421*a* of the superior sheet 421 is "dirty," i.e. has been exposed to a surrounding environment and is thus at risk for contamination. As a result, it is crucial that the superior edge 421*a* of the superior sheet 421 not slide along or otherwise come in contact with the inferior sheet 422, which has been maintained as sterile as a result of the overlap between the sheets. In the surgical draping system 420, this is accomplished by providing an attachment mechanism 423 that interconnects an inferior edge 421*b* of the superior sheet 421 to the inferior sheet 422 about at least part of the area of overlap between the two sheets. The attachment mechanism 423 can be any suitable physical means that ensures that the superior edge 421*a* of the superior sheet cannot "roll over," "pass over," or otherwise contact or come into close proximity with the inferior sheet 422, and provides an attachment of sufficient strength to ensure that the sheets are not inadvertently or prematurely separated but can be easily broken by operating room personnel; non-limiting example of such physical means include adhesive (either separate elements, e.g. tape, or adhesive portions of the sheets 421, 422 themselves), hook and loop fasteners (e.g. Velcro), heat seals, electrostatically attractive elements, and the like.

Figure 43A:
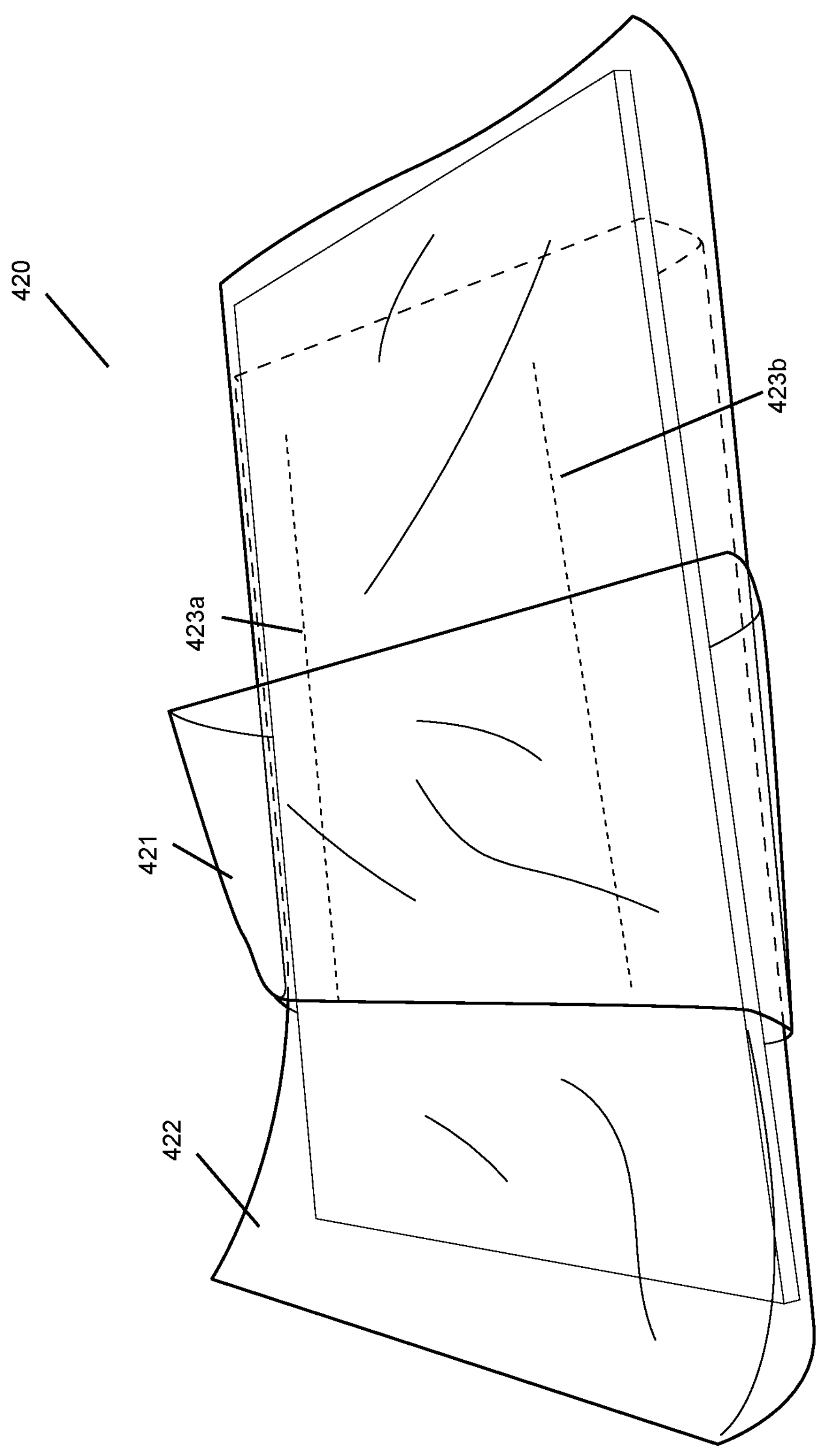
FIGS. 43A through 43C are illustrations of the use of a surgical draping system having an attachment mechanism in the form of perforated "rails," according to embodiments of the present disclosure.
Figure 43B:
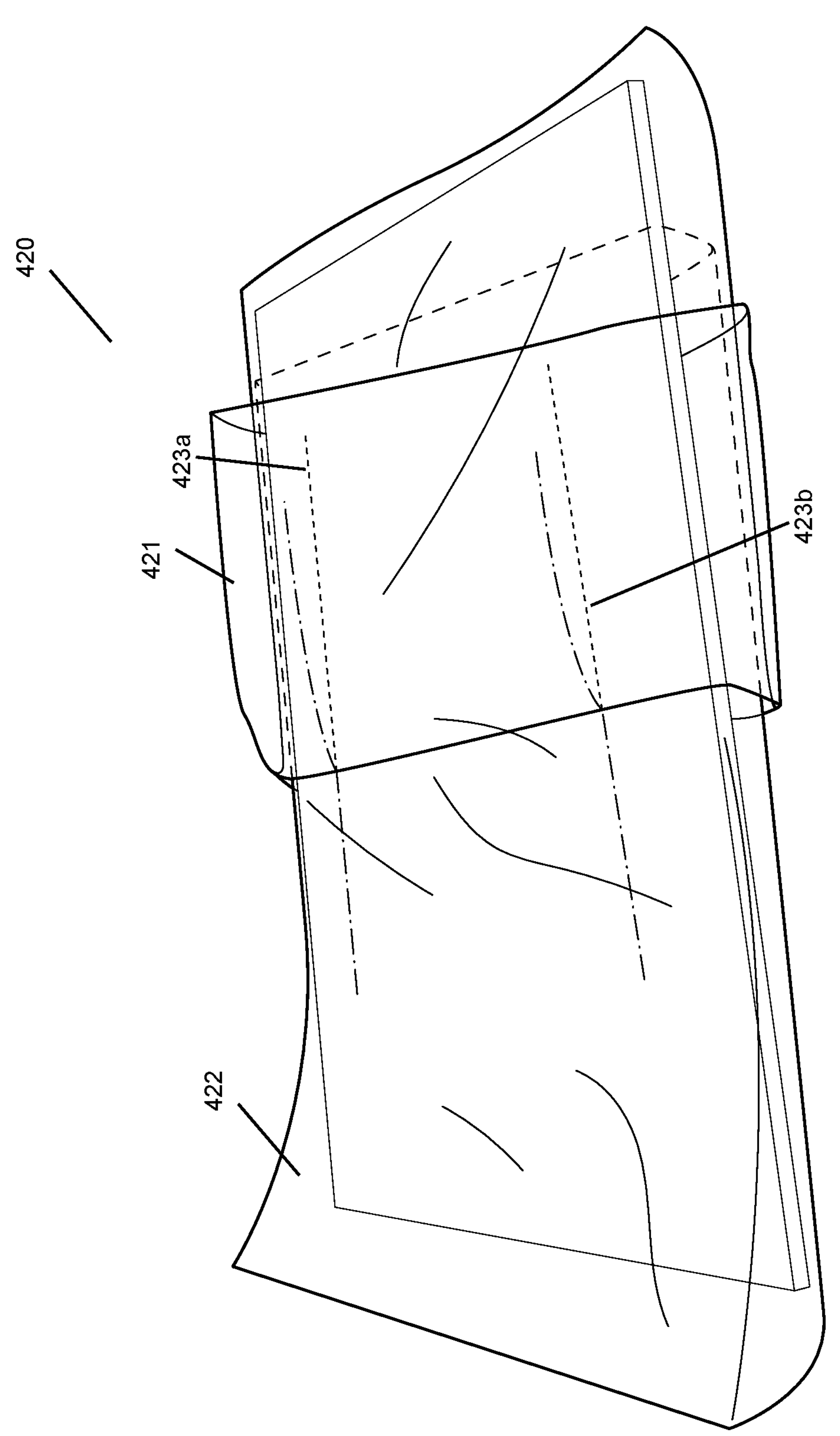
Figure 43C:
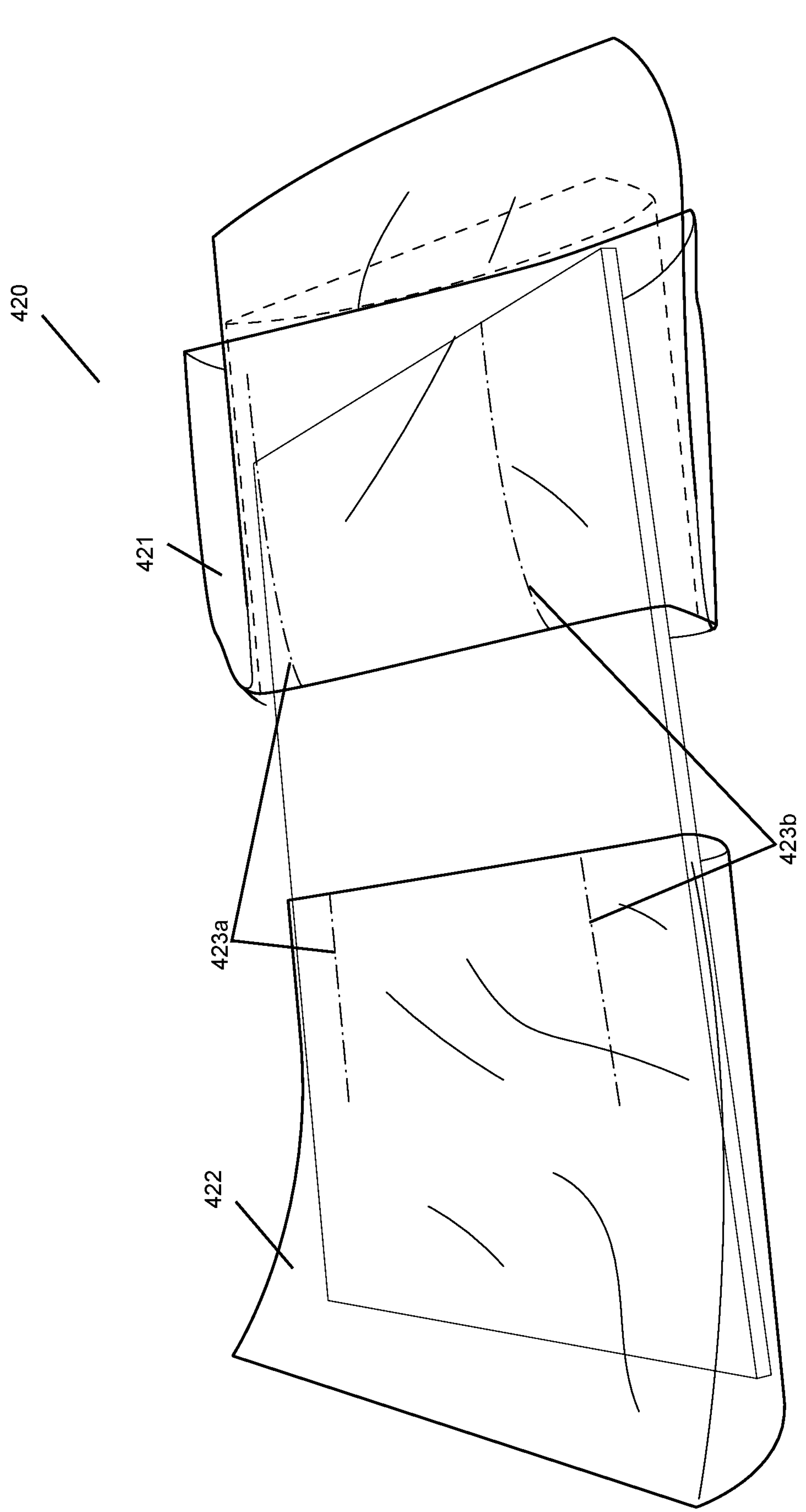

Referring now to FIGS. 43A through 43C, an embodiment of a surgical draping system 420 as illustrated in FIG. 42 is shown. In the embodiment illustrated in FIGS. 43A through 43C, the attachment mechanism 423 takes the form of perforated "rails" 423*a,b*, i.e. perforated linear strips of plastic film that are adhered, heat-sealed, or otherwise securely interconnected to the superior sheet 421 and the inferior sheet 422. As shown in FIGS. 43A through 43C, the perforation of perforated rails 423*a,b* is initially unbroken; when it is desired to separate and remove the surgical draping system 420, operating room personnel can break or open the perforations of perforated rails 423*a,b*, thus breaking the interconnection of the superior sheet 421 and the inferior sheet 422 and allowing the sheets to be easily separated and removed.

Figures 5A, 5B, 5C:
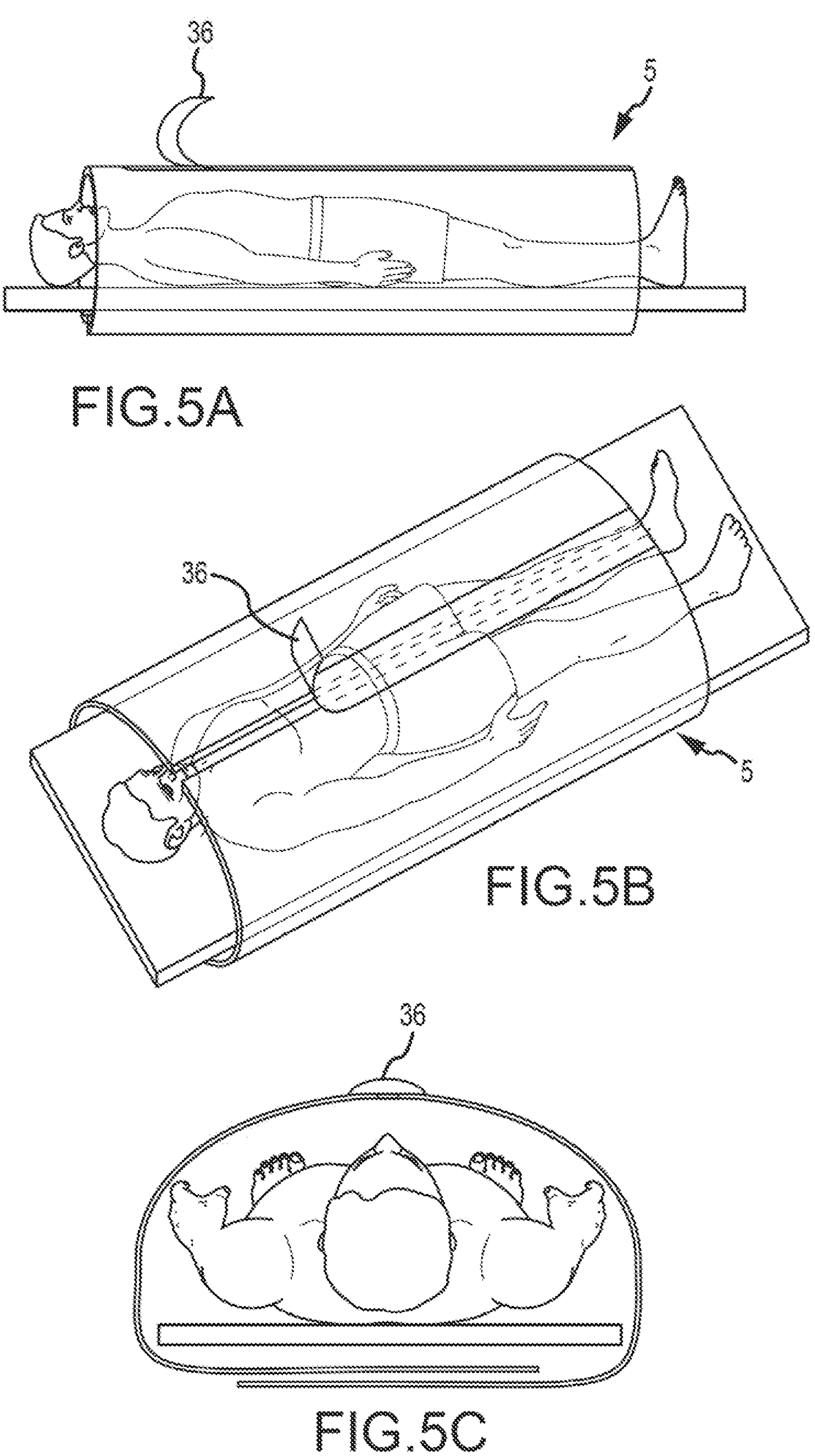
FIG. 5A is a side elevation view of a patient with a draping device according to one embodiment of the present disclosure.
FIG. 5B is a top perspective view of the draping device shown in FIG. 5A.
FIG. 5C is an end view of the draping device shown in FIG. 5A.
Figures 6A, 6B, 6C, 6D:
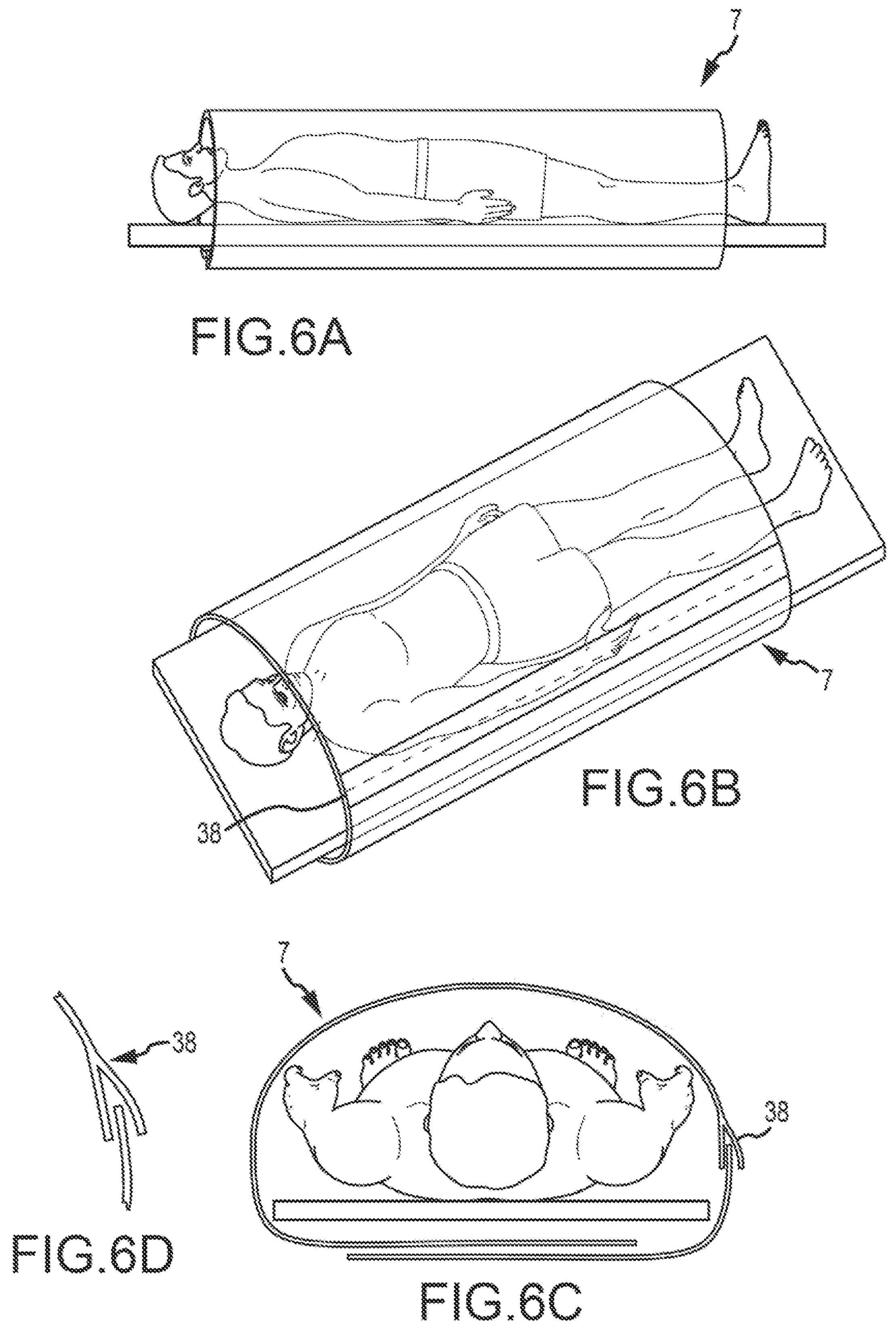
FIG. 6A is a side elevation view of a patient with a draping device according to one embodiment of the present disclosure.
FIG. 6B is a top perspective view of the draping device shown in FIG. 6A.
FIG. 6C is an end view of the draping device shown in FIG. 6A.
FIG. 6D is a detailed sectional view of the draping device shown in FIG. 6A.
Figures 7A, 7B, 7C, 7D:
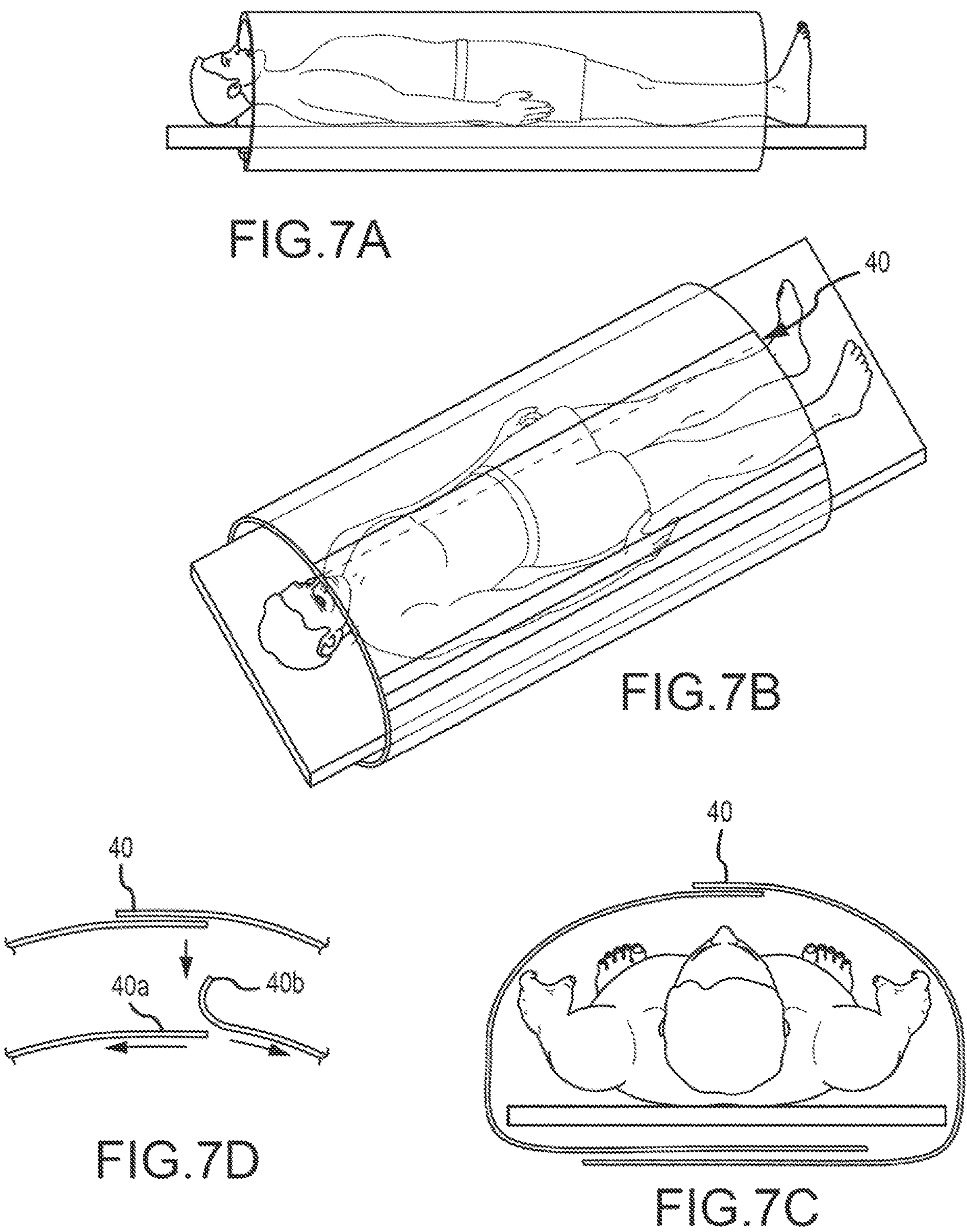
FIG. 7A is a side elevation view of a patient with a draping device according to one embodiment of the present disclosure.
FIG. 7B is a top perspective view of the draping device shown in FIG. 7A.
FIG. 7C is an end view of the draping device shown in FIG. 7A.
FIG. 7D is a sectional view of the longitudinal sterile separation for the draping device shown in FIG. 7A.
Figures 44A, 44B:
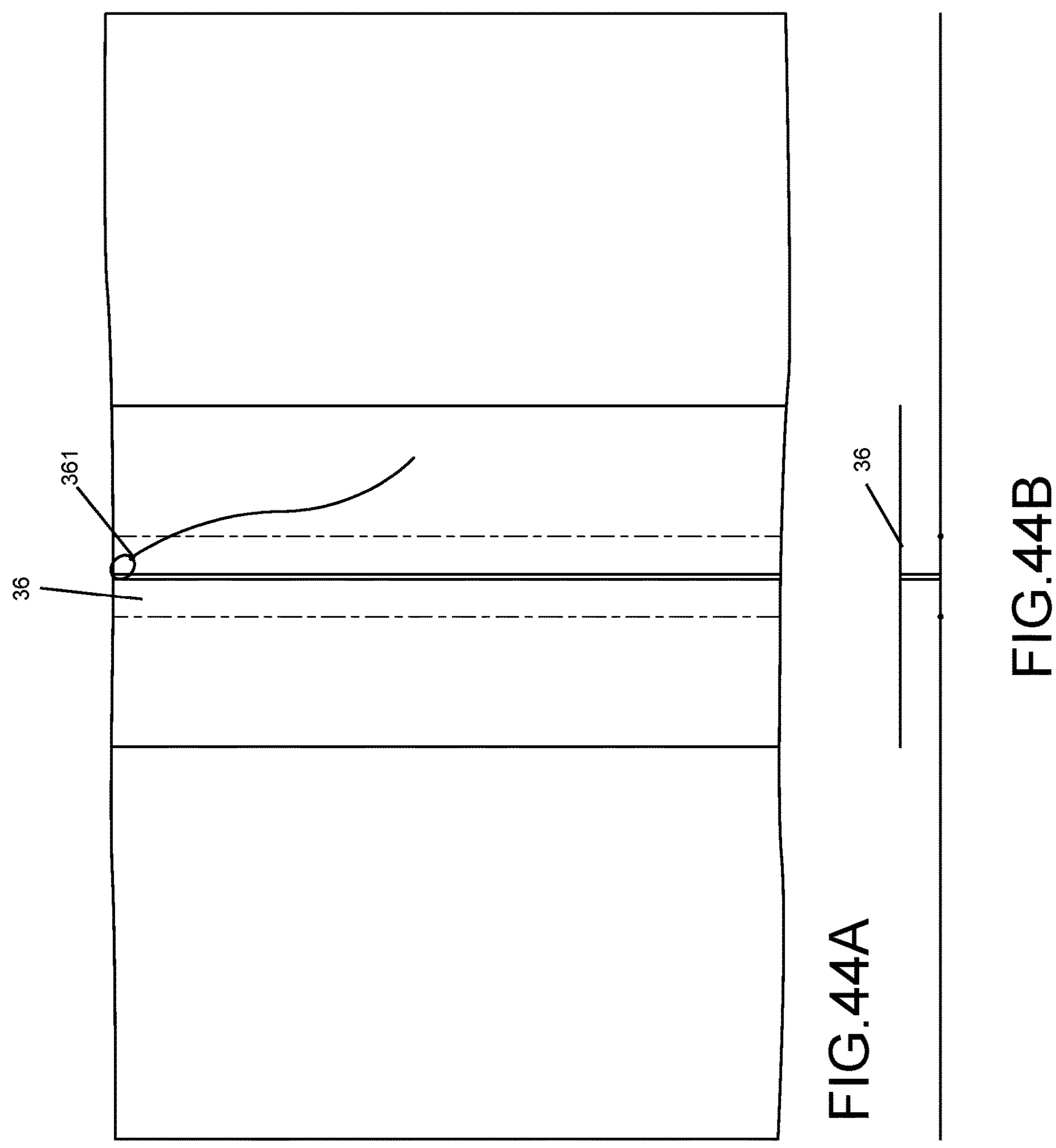
FIGS. 44A and 44B are illustrations of a surgical drape having a peel-away flap cover, according to embodiments of the present disclosure.

Referring now to FIGS. 44A and 44B, an embodiment of a surgical drape as illustrated in FIGS. 5A through 5C is shown in top and side views, respectively. Specifically, a peel-away flap cover 36 allows effacing edges of both parts of the drape to be maintained sterile before being torn or "zipped" away. In particular, the peel-away flap cover 36 takes the form of a strip of polymeric or similar material that acts as a seal connecting the top and bottom layers and may be torn from a central portion of the drape, thereby allowing one or more perforations or other separating attachments to be exposed. In the embodiment illustrated in FIGS. 44A and 44B, the peel-away flap cover 36 is provided with a cord 361, enabling operating room personnel to pull the peel-away flap cover 36 from only one side of the drape. Although the drape shown in FIGS. 5A through 5C is a patient drape, it is to be expressly understood that the peel-away flap cover 36 may be provided on any drape disclosed herein, including but not limited to a back table drape or a Mayo stand drape.

Referring now to FIGS. 45A through 45C, modified embodiments of the Z folds illustrated in, e.g., FIGS. 14A through 16 are shown. In the embodiments illustrated in FIGS. 45A through 45C, an overlap portion of the Z fold is lengthened to between about 12 inches and about 18 inches, which may, in embodiments, enable the surgical drape to be provided without a separate or superior dust cover. FIG. 45A illustrates a simple "single" Z fold. FIG. 45B illustrates a "double" Z fold in which both sub-folds open in the same direction. FIG. 45C illustrates a "double" Z fold in which the sub-folds open in opposing directions.

Surgical drapes of the present invention, including but not limited to patient drapes, back table drapes, and Mayo stand drapes, may include any one or more features that "tamper-proof" the drape, i.e. prevent drapes from being disturbed or tampered with after setup and/or provide evidence of such disturbance or tampering, and/or that enable a single user to separate the drape, e.g. by affixing a portion of the drape to a table or wall and holding that portion of the drape in place while the user applies a force to the drape. Such tamper-proofing and/or single user removal features may provide the drapes of the present invention with any of several advantages and benefits relative to surgical drapes of the prior art. One such advantage and benefit is that persons, areas, or items that must be maintained as sterile (e.g. a patient, a surface of a back table or Mayo stand or instruments thereon) can be left unattended by operating room personnel for a period before or during a surgical procedure while still guaranteeing the sterility of the underlying person, area, or item. Another such advantage and benefit is that surgical drapes of the present invention may provide more robust and complete coverage of a person, area, or item that must be maintained as sterile than surgical drapes of the prior art and thus may be useful in more challenging use cases, such as when the person, area, or item to be maintained as sterile, e.g. a sterile back table carrying surgical equipment, must be transported (e.g. an interior of an ambulance or air ambulance, a hallway or operating room transport, or instruments, equipment, or persons transported therein or thereon). Still another such advantage and benefit is that surgical drapes of the present invention may be less likely to compromise the sterility of the underlying person(s), area(s), or item(s) because, as a result of being securely affixed in place at one or more points, nonsterile edges of the drape are less likely to be brought over the person(s), area(s), or item(s) to be maintained as sterile. Tamperproof and/or single user removal features of the present invention include, as a first non-limiting example, stickers or other adhesive elements that affix a portion of the drape to a leg of a surgical stand or table (which may, in embodiments, bear sterile markings indicating the time and/or date of affixation) and, as a second non-limiting example, segments of paper or foil adapted to be placed on or around legs of a surgical table and are easily torn or wrinkled if disturbed. Other non-limiting examples of tamperproof and/or single user removal features of the present invention include straps or other elements that wrap and/or interconnect below a surface of the table (i.e. in a void space between the upper table surface and a lower shelf or support bar), a strap or similar element that secures a top (above-table) portion of the drape to the floor or an underside of the table, and/or clips or hooks incorporated into the drape that are adapted to secure the drape tightly to the legs of the table.

Single-use disposable outer surgical drapes of the present invention may incorporate various features that provide important advantages and benefits relative to surgical drapes as currently known and described in the art. Among these is that the drapes of the present invention are easy for one user (usually, a “scrubbed,” i.e. sterile, member of operating room personnel or staff) to position and place. Drapes of the present invention may be provided with an elastic feature, e.g. an elastic band, at an open end or mouth of the drape to hold the drape in place while the user position the drape, in incremental fashion, over the apparatus, device, machine, or other equipment to be protected; it is thus possible, in many embodiments of the present invention, for the user to advance the drape about a surface of the apparatus, device, machine or other equipment with one hand, while supporting an opposite portion (for bag-shaped drapes, a closed portion) with the other hand. These and other features make it possible for the user to place and/or position the drape without allowing the opposite portion to touch the operating room floor or another non-sterile surface, which is highly desirable in most (though not all) applications of drapes of the present invention.

Another advantage of surgical drapes of the present invention is that they may be made of relatively inexpensive materials, so long as these materials are highly impervious (i.e. puncture- and tear-resistant). In particular, drapes of the present invention may be made from low-cost polymers and similar materials, which need not be transparent (although this may be desired in some applications) and may in many applications be light-weight to allow removal by a single individual, preferably with only one hand.

Still another advantage of surgical drapes of the present invention is that, in applications in which they are utilized in combination with a separate inner drape (e.g. inner drapes purpose-made to drape a particular surgical apparatus, device, or machine), it is easy for a user to ensure that the inner drape and any selectively removable portions thereof remain intact and correctly positioned during placement of the outer drape of the present invention. This advantage is crucial in applications in which pieces of material of an inner drape must remain in place until immediately before the apparatus, device, or machine is used, as is the case (by way of non-limiting example) for surgical microscopes and the like.

Yet another advantage of surgical drapes of the present invention is that in most applications, they may be removed by either one or two personnel or staff who are not “scrubbed,” i.e. are not sterile. Because the outer drapes of the present invention, as a result of their novel and unique design, do not (and in fact cannot) threaten the sterility of an underlying inner drape or item of surgical equipment during removal, the outer drape may be safely, quickly, and easily removed by non-sterile personnel. In some applications a single non-sterile user may be able to remove the outer drape, while in other applications it may be advantageous for a first non-sterile user to stabilize an open end or mouth of the outer drape while a second non-sterile user separates the separable portions of the drape at the portion, e.g. by pulling an inner portion away from an outer portion.

Yet another advantage of surgical drapes of the present invention is that they may be quickly and easily removed during a surgical procedure without the possibility that an inner drape may be accidentally removed or displaced at the same time. This advantage may, in embodiments, be most fully realized by the inclusion of handles, e.g. loop handles or the like, that permit an individual who is removing the outer drape to lift the outer drape away from an inner drape (as opposed to pulling or dragging the outer drape).

Yet another advantage of surgical drapes of the present invention is that they need not be purpose-manufactured for each of many different surgical apparatuses, devices, or machines. Instead, drapes of the present invention may simply be provided in a range of sizes to allow surgical staff to select an appropriate size for a particular apparatus, device, or machine (or inner drape associated therewith).

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A surgical drape for maintaining the sterility of a sterile surface, comprising:

an outer portion, comprising an open end or mouth at an end of the predetermined length;

an inner portion, secured to the outer portion by a perforation, wherein the perforation is disposed about an entirety of a circumference of the surgical drape and circumferentially surrounds at least a portion of the sterile surface; and a Z-fold pleat, formed by the outer and inner portions and disposed about the entirety of the circumference of the surgical drape, overlying the perforation, wherein the surgical drape is configured to separate along the perforation, thereby separating the outer and inner portions, when a pulling force is applied to an end of the inner portion opposite the perforation, such that edges and surfaces of the outer portion proximate the perforation move toward the open end or mouth and edges and surfaces of the inner portion proximate the perforation move away from the open end or mouth.

2. The surgical drape of claim 1, further comprising a selectively breakable tab further securing the outer and inner portions to each other.

3. The surgical drape of claim 1, further comprising at least one handle configured to aid a user in applying the pulling force.

4. The surgical drape of claim 3, wherein the at least one handle comprises at least one inner portion handle and at least one outer portion handle.

5. The surgical drape of claim 1, wherein the end of the inner portion opposite the perforation is closed and the surgical drape thus takes the shape of a bag.

6. The surgical drape of claim 1, wherein the end of the inner portion opposite the perforation is open and the surgical drape thus takes the shape of a tube.

7. The surgical drape of claim 1, further comprising a cuff or pocket disposed at the open end or mouth.

8. The surgical drape of claim 1, wherein the sterile surface is the top surface of a Mayo stand.

9. The surgical drape of claim 8, further comprising a cinch, configured to allow a user to tighten the surgical drape about one or more legs of the Mayo stand.

10. The surgical drape of claim 1, wherein the surgical drape has a cylindrical shape and defines an interior volume having a circular or elliptical cross-section.

11. The surgical drape of claim 1, further comprising an elastic element in association with the open end or mouth, configured to assist a user in positioning the surgical drape.

12. The surgical drape of claim 11, further comprising a tightening mechanism, configured to allow the user to selectively tighten the open end or mouth.

13. The surgical drape of claim 1, further comprising a peel-away adhesive mechanism, configured to permit the open end or mouth to roll away from the perforation when the pulling force is applied.

14. The surgical drape of claim 1, further comprising a second perforation, configured to prevent premature disengagement of the Z-fold pleat when the open end or mouth is spread or widened by a user.

15. The surgical drape of claim 1, further comprising an adhesive element disposed on an underside of the Z-fold pleat.

16. The surgical drape of claim 1, further comprising one or more selectively breakable tabs, arranged in a pattern and configured to be broken in a sequence that allows a non-sterile edge of the Z-fold pleat to roll away from the edges and surfaces of the outer and inner portions proximate the perforation when the pulling force is applied.

17. The surgical drape of claim 1, further comprising a longitudinal perforation, configured to allow the outer portion of the surgical drape to be pulled or torn apart after the outer and inner portions are separated.

18. The surgical drape of claim 17, wherein the longitudinal perforation comprises a portion of the surgical drape that is weakened, or made of a material having a lower tear strength, relative to a remainder of the surgical drape.

19. The surgical drape of claim 17, wherein the longitudinal perforation comprises a score line.

20. The surgical drape of claim 17, further comprising a visual indicator of the location of the longitudinal perforation.

* * * * *